(12) United States Patent
Carey et al.

(10) Patent No.: US 11,617,684 B2
(45) Date of Patent: Apr. 4, 2023

(54) WOUND CLOSURE DEVICES

(71) Applicants: Smith & Nephew, Inc., Memphis, TN (US); University of Massachusetts, Boston, MA (US)

(72) Inventors: Jeremy Nicholas Carey, Papworth Everard (GB); Raymond M. Dunn, Shrewsbury, MA (US); Victoria Jody Hammond, Hull (GB); Edward Yerbury Hartwell, Hull (GB); Sarah Elizabeth Knight, Cambridge (GB); Marcus Damian Phillips, Wakefield (GB); Diego Alfredo Punin-Albarracin, Cambridge (GB); Mark Richardson, Grimsby (GB); Carl Dean Saxby, Brough (GB); Michael Sugrue, Donegal (IE); Iain Webster, York (GB)

(73) Assignees: Smith & Nephew, Inc., Memphis, TN (US); University of Massachusetts, Boston, MA (US)

( * ) Notice: Subject to any disclaimer, the term of this patent is extended or adjusted under 35 U.S.C. 154(b) by 103 days.

(21) Appl. No.: 16/346,786

(22) PCT Filed: Nov. 1, 2017

(86) PCT No.: PCT/US2017/059603
§ 371 (c)(1),
(2) Date: May 1, 2019

(87) PCT Pub. No.: WO2018/085457
PCT Pub. Date: May 11, 2018

(65) Prior Publication Data
US 2020/0046566 A1 Feb. 13, 2020

Related U.S. Application Data

(60) Provisional application No. 62/416,570, filed on Nov. 2, 2016.

(51) Int. Cl.
*A61F 13/00* (2006.01)
*A61M 1/00* (2006.01)

(52) U.S. Cl.
CPC .. *A61F 13/00068* (2013.01); *A61F 13/00021* (2013.01); *A61F 13/00038* (2013.01); *A61M 1/90* (2021.05); *A61F 2013/00357* (2013.01)

(58) Field of Classification Search
CPC .......... A61F 13/00068; A61F 13/00021; A61F 13/00038; A61F 2013/00357; A61M 1/0088
See application file for complete search history.

(56) References Cited

U.S. PATENT DOCUMENTS 3,014,483 A 12/1961 Mccarthy et al.
3,194,239 A 7/1965 Sullivan
(Continued)

FOREIGN PATENT DOCUMENTS

AU 2012261793 B2 11/2014
AU 2013206230 B2 5/2016
(Continued)

OTHER PUBLICATIONS

"Definition of 3D Printer," American Heritage Dictionary of the English Language, Fifth Edition, accessed on Feb. 22, 2018 from URL: https://www.thefreedictionary.co, 2016, 1 page.
(Continued)

*Primary Examiner* — Susan S Su
*Assistant Examiner* — Eric Rassavong
(74) *Attorney, Agent, or Firm* — Knobbe, Martens, Olson & Bear, LLP

(57) ABSTRACT

A negative pressure wound closure devices, systems and methods. Embodiments of the invention facilitate closure of the wound by preferentially contracting under negative pressure to provide for movement of the surrounding tissues.
(Continued)

Some embodiments may utilize a stabilizing structure with a plurality of cells configured to collapses more in the x-direction than in the y-direction.

23 Claims, 78 Drawing Sheets

(56) References Cited

U.S. PATENT DOCUMENTS

| | | | |
|---|---|---|---|
| 3,578,003 A | 5/1971 | Everett | |
| 3,789,851 A | 2/1974 | Leveen | |
| 3,812,616 A | 5/1974 | Koziol | |
| 4,467,805 A | 8/1984 | Fukuda | |
| 4,608,041 A | 8/1986 | Nielsen | |
| 4,699,134 A | 10/1987 | Samuelsen | |
| 4,815,468 A | 3/1989 | Annand | |
| 5,176,663 A * | 1/1993 | Svedman | A61F 13/0203 128/888 |
| 5,264,218 A | 11/1993 | Rogozinski | |
| 5,376,067 A | 12/1994 | Daneshvar | |
| 5,409,472 A | 4/1995 | Rawlings et al. | |
| 5,415,715 A | 5/1995 | Delage et al. | |
| 5,423,857 A | 6/1995 | Rosenman et al. | |
| 5,512,041 A | 4/1996 | Bogart | |
| 5,562,107 A | 10/1996 | Lavender et al. | |
| 5,584,859 A | 12/1996 | Brotz | |
| 5,636,643 A | 6/1997 | Argenta et al. | |
| 5,695,777 A | 12/1997 | Donovan et al. | |
| 6,176,868 B1 | 1/2001 | Detour | |
| 6,503,208 B1 | 1/2003 | Skovlund | |
| 6,548,727 B1 | 4/2003 | Swenson | |
| 6,566,575 B1 | 5/2003 | Stickels et al. | |
| 6,685,681 B2 | 2/2004 | Lockwood et al. | |
| 6,712,839 B1 | 3/2004 | Lonne | |
| 6,770,794 B2 | 8/2004 | Fleischmann | |
| 6,787,682 B2 * | 9/2004 | Gilman | A61F 13/023 602/42 |
| 6,883,531 B1 | 4/2005 | Perttu | |
| 6,977,323 B1 | 12/2005 | Swenson | |
| 7,004,915 B2 | 2/2006 | Boynton et al. | |
| 7,144,390 B1 | 12/2006 | Hannigan et al. | |
| 7,315,183 B2 | 1/2008 | Hinterscher | |
| 7,351,250 B2 | 4/2008 | Zamierowski | |
| 7,361,184 B2 | 4/2008 | Joshi | |
| 7,438,705 B2 | 10/2008 | Karpowicz et al. | |
| 7,494,482 B2 | 2/2009 | Orgill et al. | |
| 7,615,036 B2 | 11/2009 | Joshi et al. | |
| 7,622,629 B2 | 11/2009 | Aali | |
| 7,625,362 B2 | 12/2009 | Boehringer et al. | |
| 7,683,667 B2 | 3/2010 | Kim et al. | |
| 7,700,819 B2 | 4/2010 | Ambrosio et al. | |
| 7,754,937 B2 | 7/2010 | Boehringer et al. | |
| 7,779,625 B2 | 8/2010 | Joshi et al. | |
| 7,815,616 B2 | 10/2010 | Boehringer et al. | |
| 7,857,806 B2 | 12/2010 | Karpowicz et al. | |
| 7,863,495 B2 | 1/2011 | Aali | |
| 7,892,181 B2 | 2/2011 | Christensen et al. | |
| 7,896,856 B2 | 3/2011 | Petrosenko et al. | |
| 7,909,805 B2 | 3/2011 | Weston et al. | |
| 7,910,789 B2 | 3/2011 | Sinyagin | |
| 7,931,774 B2 | 4/2011 | Hall et al. | |
| 7,942,866 B2 | 5/2011 | Radl et al. | |
| 7,951,124 B2 | 5/2011 | Boehringer et al. | |
| 7,964,766 B2 | 6/2011 | Blott et al. | |
| 7,976,519 B2 | 7/2011 | Bubb et al. | |
| 7,976,524 B2 | 7/2011 | Kudo et al. | |
| 8,030,534 B2 | 10/2011 | Radl et al. | |
| 8,057,447 B2 | 11/2011 | Olson et al. | |
| 8,062,331 B2 | 11/2011 | Zamierowski | |
| 8,067,662 B2 | 11/2011 | Aali et al. | |
| 8,070,773 B2 | 12/2011 | Zamierowski | |
| 8,114,126 B2 | 2/2012 | Heaton et al. | |
| 8,123,781 B2 | 2/2012 | Zamierowski | |
| 8,142,419 B2 | 3/2012 | Heaton et al. | |
| 8,172,816 B2 | 5/2012 | Kazala, Jr. et al. | |
| 8,187,237 B2 | 5/2012 | Seegert | |
| 8,188,331 B2 | 5/2012 | Barta et al. | |
| 8,197,467 B2 | 6/2012 | Heaton et al. | |
| 8,207,392 B2 | 6/2012 | Haggstrom et al. | |
| 8,235,955 B2 | 8/2012 | Blott et al. | |
| 8,246,590 B2 | 8/2012 | Hu et al. | |
| 8,246,606 B2 | 8/2012 | Stevenson et al. | |
| 8,257,328 B2 | 9/2012 | Augustine et al. | |
| 8,273,105 B2 | 9/2012 | Cohen et al. | |
| 8,328,776 B2 | 12/2012 | Kelch et al. | |
| 8,337,411 B2 | 12/2012 | Nishtala et al. | |
| 8,353,931 B2 | 1/2013 | Stopek et al. | |
| 8,357,131 B2 | 1/2013 | Olson | |
| 8,376,972 B2 | 2/2013 | Fleischmann | |
| 8,430,867 B2 | 4/2013 | Robinson et al. | |
| 8,447,375 B2 | 5/2013 | Shuler | |
| 8,454,990 B2 | 6/2013 | Canada et al. | |
| 8,460,257 B2 | 6/2013 | Locke et al. | |
| 8,481,804 B2 | 7/2013 | Timothy | |
| 8,486,032 B2 | 7/2013 | Seegert et al. | |
| 8,500,776 B2 | 8/2013 | Ebner | |
| 8,608,776 B2 | 12/2013 | Coward et al. | |
| 8,632,523 B2 | 1/2014 | Eriksson et al. | |
| 8,673,992 B2 | 3/2014 | Eckstein et al. | |
| 8,679,080 B2 | 3/2014 | Kazala, Jr. et al. | |
| 8,679,153 B2 | 3/2014 | Dennis | |
| 8,680,360 B2 | 3/2014 | Greener et al. | |
| 8,708,984 B2 | 4/2014 | Robinson et al. | |
| 8,721,629 B2 | 5/2014 | Hardman et al. | |
| 8,746,662 B2 | 6/2014 | Poppe | |
| 8,764,732 B2 | 7/2014 | Hartwell | |
| 8,791,315 B2 | 7/2014 | Lattimore et al. | |
| 8,791,316 B2 | 7/2014 | Greener | |
| 8,802,916 B2 | 8/2014 | Griffey et al. | |
| 8,821,535 B2 | 9/2014 | Greener | |
| 8,945,030 B2 | 2/2015 | Weston et al. | |
| 9,044,579 B2 | 6/2015 | Blott et al. | |
| 9,061,095 B2 | 6/2015 | Adie et al. | |
| 9,180,231 B2 | 11/2015 | Greener | |
| 9,408,755 B2 | 8/2016 | Larsson et al. | |
| 9,421,132 B2 | 8/2016 | Dunn et al. | |
| 9,655,807 B2 | 5/2017 | Locke et al. | |
| 9,849,023 B2 | 12/2017 | Hall et al. | |
| 10,143,485 B2 | 12/2018 | Locke et al. | |
| 10,245,185 B2 * | 4/2019 | Hicks | A61M 1/0088 |
| 2001/0034499 A1 | 10/2001 | Sessions et al. | |
| 2002/0077661 A1 | 6/2002 | Saadat | |
| 2002/0161346 A1 | 10/2002 | Lockwood et al. | |
| 2004/0162512 A1 | 8/2004 | Liedtke et al. | |
| 2004/0267312 A1 | 12/2004 | Kanner et al. | |
| 2005/0142331 A1 | 6/2005 | Anderson et al. | |
| 2005/0267424 A1 | 12/2005 | Eriksson et al. | |
| 2006/0020269 A1 | 1/2006 | Cheng | |
| 2006/0058842 A1 | 3/2006 | Wilke et al. | |
| 2006/0069357 A1 | 3/2006 | Marasco | |
| 2006/0155260 A1 | 7/2006 | Blott et al. | |
| 2006/0217795 A1 | 9/2006 | Besselink et al. | |
| 2006/0271018 A1 | 11/2006 | Korf | |
| 2007/0052144 A1 | 3/2007 | Knirck et al. | |
| 2007/0104941 A1 | 5/2007 | Kameda et al. | |
| 2007/0118096 A1 | 5/2007 | Smith et al. | |
| 2007/0123973 A1 | 5/2007 | Roth et al. | |
| 2007/0129660 A1 | 6/2007 | McLeod et al. | |
| 2007/0149910 A1 | 6/2007 | Zocher | |
| 2007/0185463 A1 | 8/2007 | Mulligan | |
| 2007/0213597 A1 | 9/2007 | Wooster | |
| 2007/0282309 A1 | 12/2007 | Bengtson et al. | |
| 2008/0041401 A1 | 2/2008 | Casola et al. | |
| 2008/0108977 A1 | 5/2008 | Heaton et al. | |
| 2008/0243096 A1 | 10/2008 | Svedman et al. | |
| 2008/0275409 A1 | 11/2008 | Kane et al. | |
| 2008/0306456 A1 | 12/2008 | Riesinger | |
| 2009/0005716 A1 | 1/2009 | Abuzaina et al. | |
| 2009/0099519 A1 | 4/2009 | Kaplan | |
| 2009/0105670 A1 | 4/2009 | Bentley et al. | |
| 2009/0204423 A1 | 8/2009 | Degheest et al. | |
| 2009/0312685 A1 | 12/2009 | Olsen et al. | |
| 2010/0022990 A1 | 1/2010 | Karpowicz et al. | |

(56) References Cited

U.S. PATENT DOCUMENTS

| | | |
|---|---|---|
| 2010/0047324 A1 | 2/2010 | Fritz et al. |
| 2010/0081983 A1 | 4/2010 | Zocher et al. |
| 2010/0106184 A1* | 4/2010 | Coward .............. A61M 1/0088 |
| | | 606/213 |
| 2010/0137775 A1 | 6/2010 | Hu et al. |
| 2010/0150991 A1 | 6/2010 | Bernstein |
| 2010/0160874 A1 | 6/2010 | Robinson et al. |
| 2010/0179493 A1 | 7/2010 | Heagle et al. |
| 2010/0179515 A1 | 7/2010 | Swain et al. |
| 2010/0198128 A1 | 8/2010 | Turnlund et al. |
| 2010/0262106 A1 | 10/2010 | Hartwell |
| 2010/0280468 A1 | 11/2010 | Haggstrom et al. |
| 2010/0312159 A1 | 12/2010 | Aali et al. |
| 2011/0021965 A1 | 1/2011 | Karp et al. |
| 2011/0022082 A1 | 1/2011 | Burke et al. |
| 2011/0059291 A1 | 3/2011 | Boyce et al. |
| 2011/0066096 A1 | 3/2011 | Svedman |
| 2011/0082480 A1 | 4/2011 | Viola |
| 2011/0110996 A1 | 5/2011 | Schoenberger et al. |
| 2011/0112458 A1 | 5/2011 | Holm et al. |
| 2011/0178451 A1 | 7/2011 | Robinson et al. |
| 2011/0213319 A1 | 9/2011 | Blott et al. |
| 2011/0224631 A1 | 9/2011 | Simmons et al. |
| 2011/0224632 A1 | 9/2011 | Zimnitsky et al. |
| 2011/0224634 A1 | 9/2011 | Locke et al. |
| 2011/0264138 A1 | 10/2011 | Avelar et al. |
| 2011/0270301 A1 | 11/2011 | Cornet et al. |
| 2011/0305736 A1 | 12/2011 | Wieland et al. |
| 2012/0016321 A1 | 1/2012 | Wu et al. |
| 2012/0029455 A1 | 2/2012 | Perez-Foullerat et al. |
| 2012/0059412 A1 | 3/2012 | Fleischmann |
| 2012/0130327 A1 | 5/2012 | Marquez |
| 2012/0136326 A1 | 5/2012 | Croizat et al. |
| 2012/0136328 A1 | 5/2012 | Johannsson et al. |
| 2012/0143113 A1 | 6/2012 | Robinson et al. |
| 2012/0172926 A1 | 7/2012 | Hotter |
| 2012/0191132 A1 | 7/2012 | Sargeant |
| 2012/0209226 A1 | 8/2012 | Simmons et al. |
| 2012/0209227 A1 | 8/2012 | Dunn et al. |
| 2012/0238931 A1 | 9/2012 | Rastegar et al. |
| 2012/0253302 A1 | 10/2012 | Corley |
| 2013/0012891 A1 | 1/2013 | Gross et al. |
| 2013/0023842 A1 | 1/2013 | Song |
| 2013/0066365 A1 | 3/2013 | Belson et al. |
| 2013/0150813 A1 | 6/2013 | Gordon et al. |
| 2013/0190705 A1 | 7/2013 | Vess et al. |
| 2013/0197457 A1 | 8/2013 | Kazala, Jr. et al. |
| 2013/0204213 A1 | 8/2013 | Heagle et al. |
| 2013/0245527 A1 | 9/2013 | Croizat et al. |
| 2013/0325142 A1 | 12/2013 | Hunter et al. |
| 2013/0331757 A1 | 12/2013 | Belson |
| 2014/0094730 A1* | 4/2014 | Greener ............ A61F 13/00038 |
| | | 602/46 |
| 2014/0163415 A1 | 6/2014 | Zaiken et al. |
| 2014/0249495 A1 | 9/2014 | Mumby et al. |
| 2015/0065968 A1 | 3/2015 | Sealy et al. |
| 2015/0100008 A1* | 4/2015 | Chatterjee ........... A61F 13/0206 |
| | | 602/46 |
| 2015/0119837 A1 | 4/2015 | Thompson, Jr. et al. |
| 2015/0157758 A1 | 6/2015 | Blücher et al. |
| 2015/0190288 A1 | 7/2015 | Dunn et al. |
| 2015/0216732 A1 | 8/2015 | Hartwell et al. |
| 2015/0320434 A1* | 11/2015 | Ingram ................. A61M 27/00 |
| | | 606/131 |
| 2015/0320602 A1* | 11/2015 | Locke ............... A61F 13/00068 |
| | | 606/213 |
| 2015/0320603 A1* | 11/2015 | Locke .................... A61L 31/06 |
| | | 604/543 |
| 2015/0374561 A1 | 12/2015 | Hubbard, Jr. et al. |
| 2016/0144085 A1 | 5/2016 | Melin et al. |
| 2016/0184496 A1 | 6/2016 | Jaecklein et al. |
| 2017/0065751 A1 | 3/2017 | Toth et al. |
| 2017/0281838 A1 | 10/2017 | Dunn |
| 2018/0140465 A1* | 5/2018 | Dunn ................. A61M 1/0088 |

FOREIGN PATENT DOCUMENTS

| | | |
|---|---|---|
| CN | 101112326 A | 1/2008 |
| CN | 101744688 A | 6/2010 |
| CN | 201519362 U | 7/2010 |
| CN | 102038575 A | 5/2011 |
| CN | 202568632 U | 12/2012 |
| CN | 103071197 A | 5/2013 |
| CN | 203408163 U | 1/2014 |
| DE | 2949920 A1 | 3/1981 |
| EP | 1320342 A1 | 6/2003 |
| EP | 2279016 A1 | 2/2011 |
| EP | 2567717 A1 | 3/2013 |
| GB | 2389794 A | 12/2003 |
| GB | 2423019 A | 8/2006 |
| GB | 2489947 A | 10/2012 |
| GB | 2496310 A | 5/2013 |
| JP | S62-57560 A | 3/1987 |
| JP | 2006-528038 A | 12/2006 |
| JP | 2009-525087 A | 7/2009 |
| JP | 2012-105840 A | 6/2012 |
| RU | 62504 U1 | 4/2007 |
| SU | 1818103 A1 | 5/1993 |
| WO | WO 01/85248 A1 | 11/2001 |
| WO | WO 01/89392 A2 | 11/2001 |
| WO | WO 02/05737 A1 | 1/2002 |
| WO | WO 03/003948 A1 | 1/2003 |
| WO | WO 03/049598 A2 | 6/2003 |
| WO | WO 2005/046761 A1 | 5/2005 |
| WO | WO 2005/105174 A1 | 11/2005 |
| WO | WO 2006/046060 A2 | 5/2006 |
| WO | WO 2008/027449 A2 | 3/2008 |
| WO | WO 2008/064502 A1 | 6/2008 |
| WO | WO 2008/104609 A1 | 9/2008 |
| WO | WO 2009/112062 A1 | 9/2009 |
| WO | WO 2010/033725 A2 | 3/2010 |
| WO | WO 2010/097570 A1 | 9/2010 |
| WO | WO-2010097570 A1 * | 9/2010 ........ A61F 13/00068 |
| WO | WO 2011/023384 A1 | 3/2011 |
| WO | WO 2012/082716 A2 | 6/2012 |
| WO | WO 2012/082876 A1 | 6/2012 |
| WO | WO-2012106590 A2 * | 8/2012 ........... A61M 1/0088 |
| WO | WO 2012/136707 A1 | 10/2012 |
| WO | WO 2012/142473 A1 | 10/2012 |
| WO | WO 2013/012381 A1 | 1/2013 |
| WO | WO 2013/043258 A1 | 3/2013 |
| WO | WO 2013/071243 A2 | 5/2013 |
| WO | WO 2013/076450 A1 | 5/2013 |
| WO | WO 2013/079947 A1 | 6/2013 |
| WO | WO 2013/175309 A1 | 11/2013 |
| WO | WO 2013/175310 A2 | 11/2013 |
| WO | WO 2014/013348 A2 | 1/2014 |
| WO | WO 2014/014842 A1 | 1/2014 |
| WO | WO 2014/014871 A1 | 1/2014 |
| WO | WO-2014014922 A1 * | 1/2014 ........ A61F 13/00068 |
| WO | WO 2014/140578 A1 | 9/2014 |
| WO | WO 2014/158526 A1 | 10/2014 |
| WO | WO 2014/165275 A1 | 10/2014 |
| WO | WO 2014/178945 A1 | 11/2014 |
| WO | WO 2014/194786 A1 | 12/2014 |
| WO | WO 2015/008054 A1 | 1/2015 |
| WO | WO-2015026968 A1 * | 2/2015 ......... A61B 17/0206 |
| WO | WO 2015/061352 A2 | 4/2015 |
| WO | WO-2015061352 A2 * | 4/2015 ........ A61F 13/00068 |
| WO | WO 2015/109359 A1 | 7/2015 |
| WO | WO 2015/110409 A1 | 7/2015 |
| WO | WO 2015/110410 A1 | 7/2015 |
| WO | WO 2015/169637 A1 | 11/2015 |
| WO | WO 2015/172108 A1 | 11/2015 |
| WO | WO 2015/193257 A1 | 12/2015 |
| WO | WO 2016/018448 A1 | 2/2016 |
| WO | WO 2016/176513 A1 | 11/2016 |
| WO | WO 2016/179245 A1 | 11/2016 |
| WO | WO-2016176513 A1 * | 11/2016 ........ A61F 13/00068 |
| WO | WO 2018/038665 A1 | 3/2018 |
| WO | WO 2018/041805 A1 | 3/2018 |
| WO | WO 2018/044949 A1 | 3/2018 |

(56) References Cited

FOREIGN PATENT DOCUMENTS

| WO | WO 2018/085457 A1 | 5/2018 |
| WO | WO 2018/140386 | 8/2018 |
| WO | WO 2018/237206 | 12/2018 |

OTHER PUBLICATIONS

"Definition of Adhere," The Free Dictionary, accessed on Mar. 23, 2017 from http://www.thefreedictionary.com/adhere, 6 pages.

"Definition of Oculiform," Webster's Revised Unabridged Dictionary, accessed from The Free Dictionary on May 30, 2018 from URL: https://www.thefreedictionary.com/Oculiform, 1913, 1 page.

"Definition of Throughout," Merriam-Webster Dictionary, accessed on Aug. 29, 2017 from https://www.merriam-webster.com/dictionary/throughout, 11 pages.

Hougaard, et al., "The Open Abdomen: Temporary Closure with a Modified Negative Pressure Therapy Technique," International Wound Journal, ISSN 1742-4801, 2014, pp. 13-16.

Kapischke M., et al., "Self-Fixating Mesh for the Lichtenstein Procedure—a Prestudy," Langenbecks Arch Surg, 2010, vol. 395, pp. 317-322.

International Preliminary Report on Patentability for Application No. PCT/US2017/059603, dated May 7, 2019, 9 pages.

International Search Report and Written Opinion for Application No. PCT/US2017/059603, dated Dec. 22, 2017, 12 pages.

\* cited by examiner

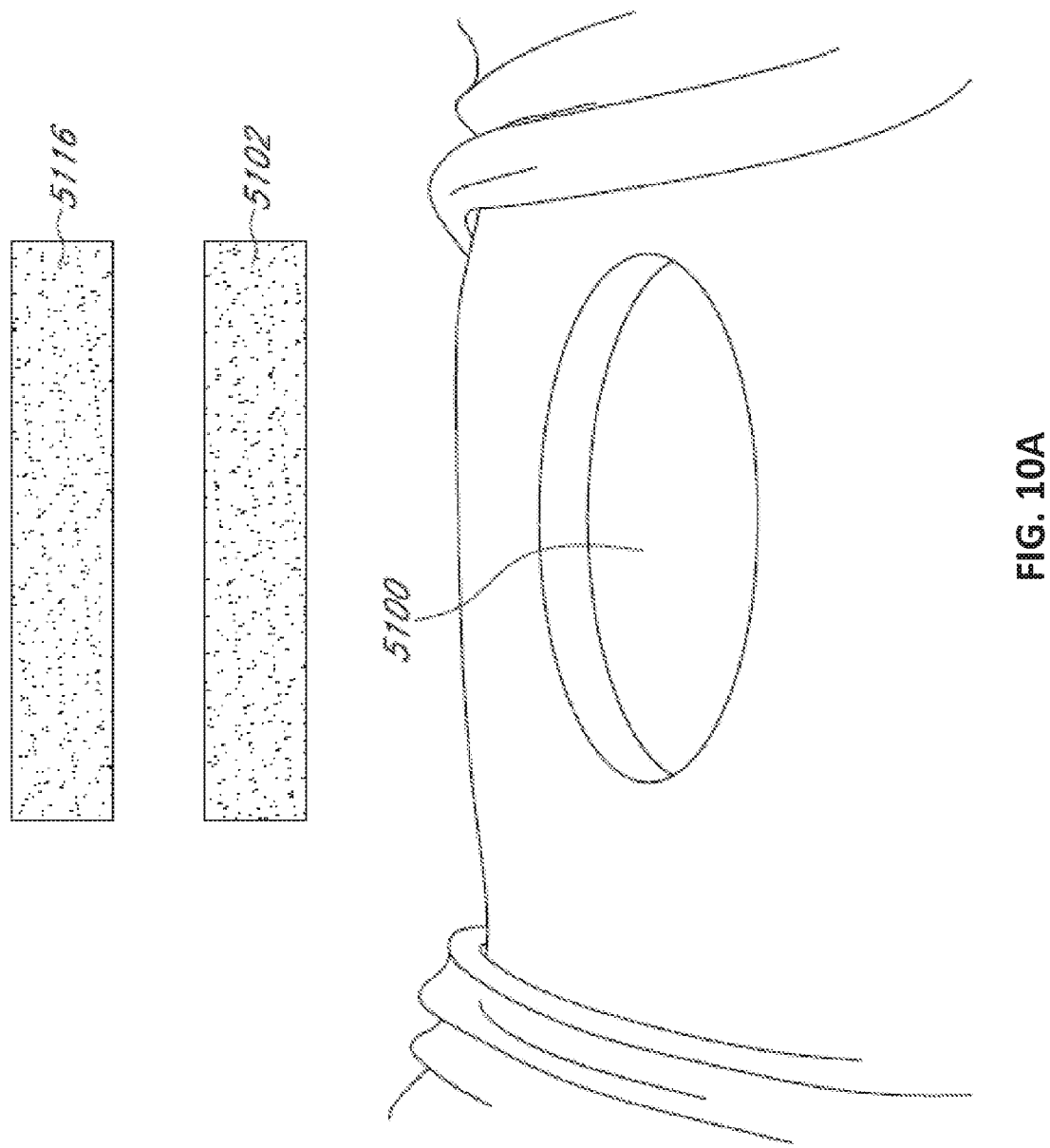

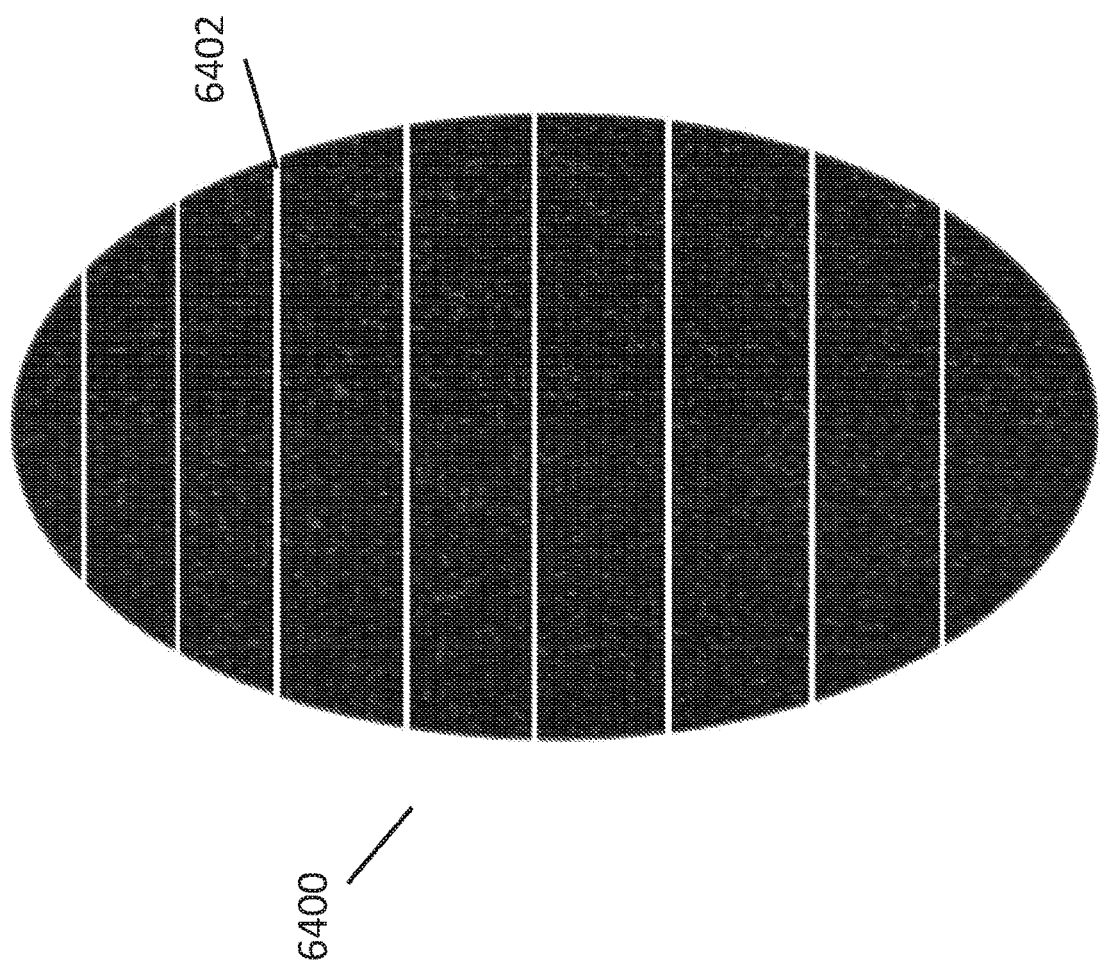

Updated matrix X12_Feb15_03 (15mm Foam Attached to top and bottom, bottom foam under facia) incremental vacuum increase [2]

| Width mm - Pre Vacuum | Width mm - (xx) mmHg | % Change | Actual Change mm |
|---|---|---|---|
| Single Measurement | Single Measurement | | |
| 123.4 | 83.4 (40) | 32.41% | 40.0 |
| 123.4 | 83.4 (50) | 34.85% | 43.0 |
| 123.4 | 83.4 (60) | 36.06% | 44.5 |
| 123.4 | 83.4 (70) | 38.41% | 47.4 |
| 123.4 | 83.4 (80) | 38.82% | 47.9 |
| 123.4 | 83.4 (100) | 42.79% | 52.8 |
| 123.4 | 83.4 (120) | 44.65% | 55.1 |
| 123.4 | 83.4 (140) | 46.76% | 57.7 |
| 123.4 | 83.4 (160) | 48.87% | 60.3 |
| 123.4 | 83.4 (180) | 50.41% | 62.2 |
| 123.4 | 83.4 (200) | 50.89% | 62.8 |
| 123.4 | 83.4 (200) Relax | 52.11% | 64.3 |

FIG. 23A

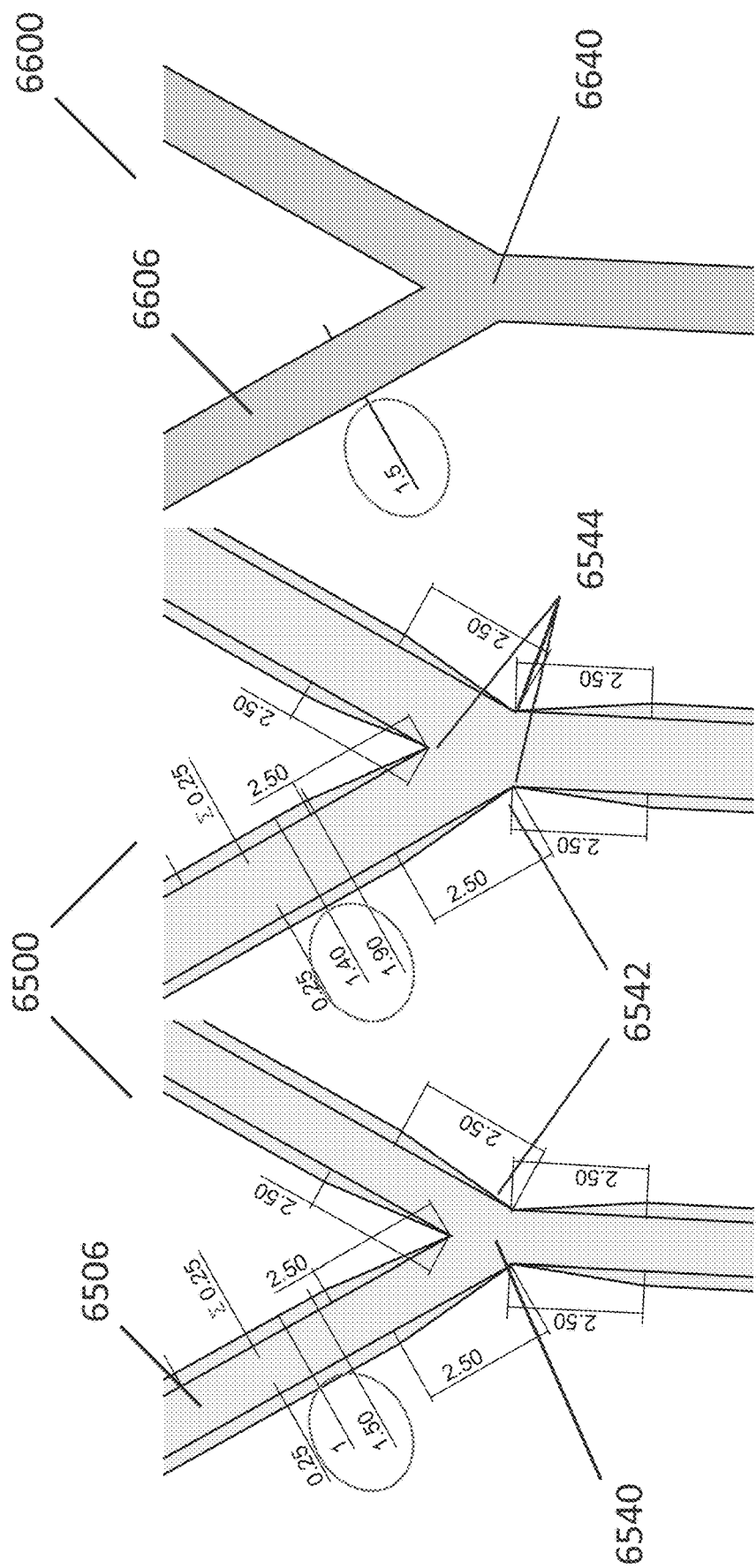

WOUND CLOSURE DEVICES

CROSS-REFERENCE TO RELATED APPLICATIONS

This application is a U.S. national stage application of International Patent Application No. PCT/US2017/059603, filed Nov. 1, 2017, which claims the benefit of U.S. Provisional Application No. 62/416,570, filed Nov. 2, 2016, the disclosure of each of which is hereby incorporated by reference in its entirety.

BACKGROUND OF THE INVENTION

Field of the Invention

This application describes embodiments of apparatuses, methods, and systems for the treatment of wounds, specifically to aid in the closure of large wounds, in conjunction with the administration of negative pressure.

Description of the Related Art

Negative pressure wound therapy has been used in the treatment of wounds, and in many cases can improve the rate of healing while also removing exudates and other deleterious substances from the wound site.

Abdominal compartment syndrome is caused by fluid accumulation in the peritoneal space due to edema and other such causes, and results in greatly increased intra-abdominal pressure that may cause organ failure eventually resulting in death. Causes may include sepsis or severe trauma. Treatment of abdominal compartment syndrome may require an abdominal incision to permit decompression of the abdominal space, and as such, a large wound may be created onto the patient. Closure of this wound, while minimizing the risk of secondary infections and other complications, and after the underlying edema has subsided, then becomes a priority. However, acute open abdominal conditions may be caused by other reasons in addition to compartment syndrome, as described further below.

Other large or incisional wounds, either as a result of surgery, trauma, or other conditions, may also require closure. For example, wounds resulting from sterniotomies, fasciotomies, and other abdominal wounds may require closure. Wound dehiscence of existing wounds is another complication that may arise, possibly due to incomplete underlying fascial closure, or secondary factors such as infection.

Existing negative pressure treatment systems, while permitting eventual wound closure, still require lengthy closure times. Although these may be combined with other tissue securement means, such as sutures, there is also a risk that underlying muscular and fascial tissue is not appropriately reapproximated so as to permit complete wound closure. Further, when foam or other wound fillers are inserted into the wound, the application of negative pressure to the wound and the foam may cause atmospheric pressure to bear down onto the wound, compressing the foam downward and outward against the margins of the wound. This downward compression of the wound filler slows the healing process and slows or prevents the joining of wound margins. Additionally, inflammation of the fascia in the form of certain types of fasciitis can lead to rapid and excessive tissue loss, potentially meriting the need for more advanced negative pressure treatment systems. Accordingly, there is a need to provide for an improved apparatus, method, and system for the treatment and closure of wounds.

SUMMARY OF THE INVENTION

Embodiments of the present invention relate to negative pressure wound closure devices, methods, and systems that facilitate closure of a wound. It will be understood by one of skill in the art that the wounds described herein this specification may encompass any wound, and are not limited to a particular location or type of wound. The devices, methods, and systems may operate to reduce the need for repetitive replacement of wound filler material currently employed and can advance the rate of healing. The devices, methods, and systems may be simultaneously used with negative pressure to remove wound fluids.

In certain embodiments, an apparatus for treating a wound with negative pressure wound therapy is provided, the apparatus comprises a stabilizing structure for insertion into a wound. The stabilizing structure comprises a length corresponding to a y-direction and extending along a central longitudinal axis of the stabilizing structure between a first end and a second end of the stabilizing structure, a width corresponding to an x-direction, the width being transverse to the length and extending along a central transverse axis of the stabilizing structure between a first side and a second side of the stabilizing structure, and a height corresponding to a z-direction, the height being transverse to the length and the width and extending between a top surface and a bottom surface of the stabilizing structure. The length and width of the stabilizing structure may each be greater than the height. The stabilizing structure may further comprise a plurality of cells defined by one or more walls, the cells being provided side-by-side in a horizontal plane parallel to the x-direction and the y-direction, wherein each of the cells has a top end and a bottom end with an opening extending through the top and bottom ends in the z-direction. The stabilizing structure may also be configured such that upon application of negative pressure to the wound when the stabilizing structure is inserted into the wound, the stabilizing structure collapses more in the horizontal plane than in the z-direction, and the stabilizing structure collapses more in the x-direction than in the y-direction.

In certain embodiments, the outer cells located farther away from the central longitudinal axis of the stabilizing structure are sized and configured to collapse before inner cells located closer to the central longitudinal axis of the stabilizing structure.

In certain embodiments, the cells located closer to the central transverse axis of the stabilizing structure are sized and configured to collapse before cells located farther away from the central transverse axis of the stabilizing structure.

In certain embodiments, the cells located closer to the central transverse axis of the stabilizing structure are sized and configured to collapse at a faster rate than cells located farther away from the central transverse axis of the stabilizing structure.

In certain embodiments, the stabilizing structure has an oculiform shape.

In certain embodiments, the stabilizing structure comprises cells of uniform size.

In certain embodiments, the stabilizing structure comprises cells of different sizes. In some embodiments, the cells located closer to the central transverse axis of the stabilizing structure are larger than cells located farther away from the central transverse axis of the stabilizing structure. Additionally, in some embodiments, the cells located closer to the central longitudinal axis of the stabilizing structure are larger than cells located farther away from the central longitudinal axis of the stabilizing structure.

In certain embodiments, the cells are defined by one or more walls having varying stiffness. The one or more walls defining the cells may be made of a material having a Shore hardness of 80 or less, 60 or less, or 40 or less. The one or more walls defining the cells may be made of a material having a Young's modulus of 20 MPa or less, 12 MPa or less, 5 MPa or less, 1 MPa or less.

In certain embodiments, the stabilizing structure comprises walls of uniform wall thickness.

In certain embodiments, the stabilizing structure comprises walls of non-uniform wall thickness. The walls may taper to create a hinge and wherein the hinge is sized and configured to increase rotation at a junction between one or more walls upon application of negative pressure to the wound when the stabilizing structure is inserted into the wound.

In certain embodiments, the internal radius is sized and configured to increase cell sizes and/or collapse of the stabilizing structure upon application of negative pressure to the wound when the stabilizing structure is inserted into the wound.

In certain embodiments, an amount of cells adjacent a center portion of the stabilizing structure are greater than an amount of cells adjacent the first or second ends of the stabilizing structure.

In certain embodiments, the plurality of cells are sized and configured to increase collapse of the first and second end of the stabilizing structure upon application of negative pressure to the wound when the stabilizing structure is inserted into the wound.

In certain embodiments, the apparatus further comprises a foam layer, wherein the foam layer is seized and configured to increase the width of the stabilizing structure upon application of negative pressure to the wound when the stabilizing structure is inserted into the wound.

In certain embodiments, an apparatus for treating a wound with negative pressure wound therapy may comprise a stabilizing structure for insertion into a wound. The stabilizing structure comprises a length corresponding to a y-direction and extending along a central longitudinal axis of the stabilizing structure between a first end and a second end of the stabilizing structure, a width corresponding to an x-direction, the width being transverse to the length and extending along a central transverse axis of the stabilizing structure between a first side and a second side of the stabilizing structure, and a height corresponding to a z-direction, the height being transverse to the length and the width and extending between a top surface and a bottom surface of the stabilizing structure. The length and width of the stabilizing structure may each be greater than the height. The stabilizing structure may further comprise a plurality of cells defined by one or more walls, the cells being provided side-by-side in a horizontal plane parallel to the x-direction and the y-direction, wherein each of the cells has a top end and a bottom end with an opening extending through the top and bottom ends in the z-direction. The stabilizing structure may also be configured such that upon application of negative pressure to the wound when the stabilizing structure is inserted into the wound, the stabilizing structure collapses more in the horizontal plane than in the z-direction, and the stabilizing structure collapses more in the x-direction than in the y-direction. The apparatus may further comprise cells located farther away from the central transverse axis of the stabilizing structure that are sized and configured to cause one or both longitudinal end portions of the stabilizing structure to collapse uniformly with a central portion of the stabilizing structure between the longitudinal end portions upon application of negative pressure.

In certain embodiments, the stabilizing structure has an oculiform shape.

In certain embodiments, the stabilizing structure has cells of varying size.

In certain embodiments, the stabilizing structure has walls of varying thickness.

In certain embodiments, the stabilizing structure has cells of varying internal radius.

In certain embodiments, the stabilizing structure has walls of varying stiffness or hardness.

In certain embodiments, cells located closer to the central transverse axis of the stabilizing structure are larger than cells located farther away from the central transverse axis of the stabilizing structure.

In certain embodiments, cells located closer to the central longitudinal axis of the stabilizing structure are larger than cells located farther away from the central longitudinal axis of the stabilizing structure.

In certain embodiments, a majority of the cells are diamond-shaped.

In certain embodiments, the stabilizing structure is symmetrical about its central longitudinal axis.

In certain embodiments, the stabilizing structure is symmetrical about its central transverse axis.

In certain embodiments, at least some of the cells relatively closer to the longitudinal ends of the stabilizing structure are larger than cells relatively closer to the central longitudinal axis.

In certain embodiments, the stabilizing structure comprises a plurality of closed cells each defined by four internal walls.

In certain embodiments, the stabilizing structure comprises at least some open cells.

In certain embodiments, the open cells are located closer to the longitudinal ends of the stabilizing structure than the central longitudinal axis.

In certain embodiments, the cells of the stabilizing structure are sized and configured so that one or both longitudinal end portions of the stabilizing structure collapse to have about the same width as a width at the central transverse axis upon application of negative pressure.

Other embodiments of wound closure devices, stabilizing structures and associated apparatuses are described below.

BRIEF DESCRIPTION OF THE DRAWINGS

Other features and advantages of the present invention will be apparent from the following detailed description of the invention, taken in conjunction with the accompanying drawings of which:

FIGS. 10A-C illustrate an embodiment of steps of a method of treating a wound.

FIGS. 22A-E illustrate embodiments of a foam layer with printing.

FIGS. 23A-B present experimental data collected using embodiments of stabilizing structures and wound closure devices.

FIGS. 25-27 illustrate enlarged views of different embodiments of a stabilizing structure.

DETAILED DESCRIPTION OF THE PREFERRED EMBODIMENTS

Figure 1:
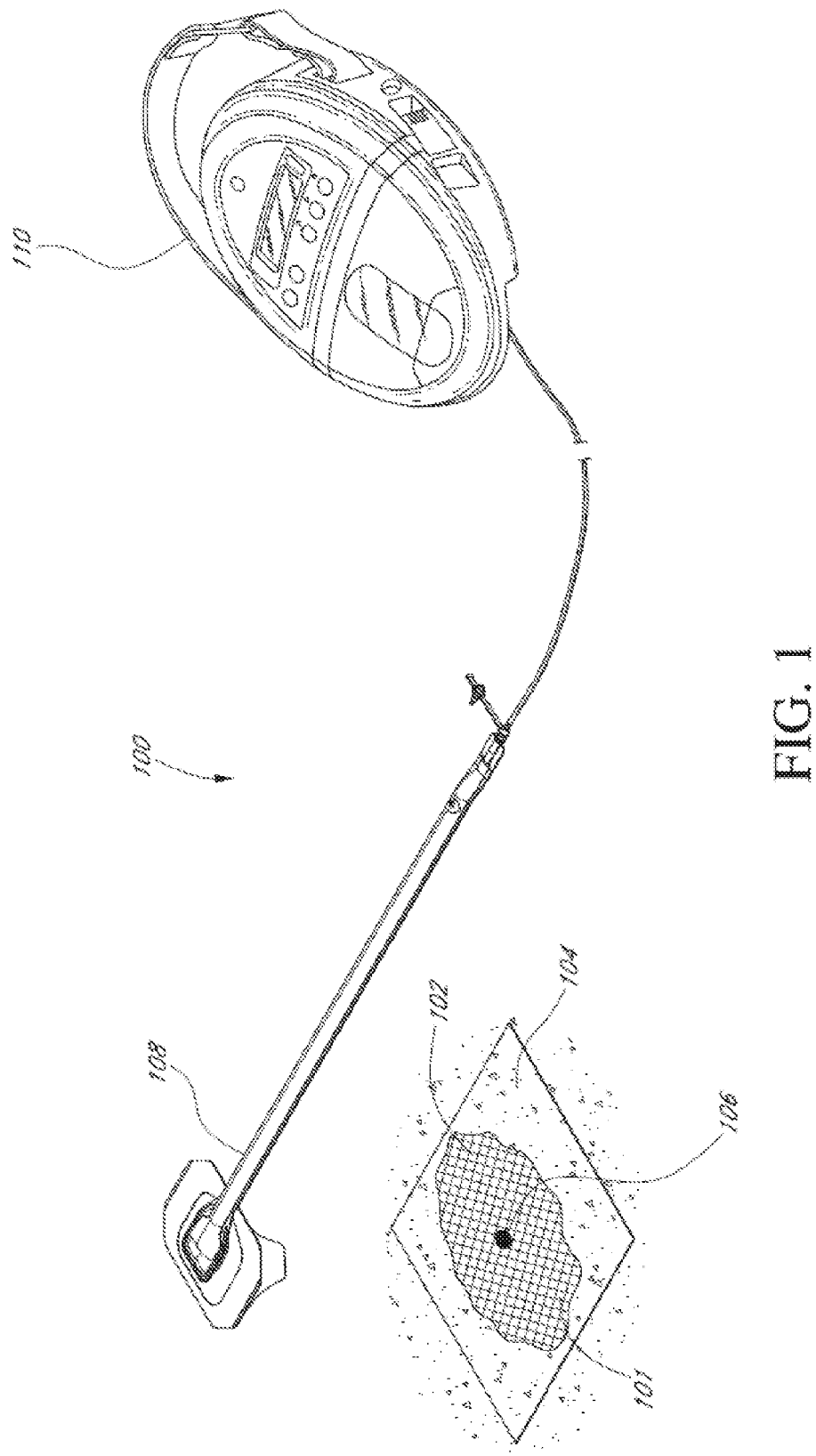
FIG. 1 illustrates an embodiment of a negative pressure treatment system.

Embodiments disclosed in this section or elsewhere in this specification relate to apparatuses and methods of treating a wound with reduced pressure, including pump and wound dressing components and apparatuses. The apparatuses and components comprising the wound overlay and packing materials, if any, are sometimes collectively referred to in this section or elsewhere in this specification as dressings.

It will be appreciated that throughout this specification reference is made to a wound. It is to be understood that the term wound is to be broadly construed and encompasses open and closed wounds in which skin is torn, cut or punctured or where trauma causes a contusion, or any other superficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, abdominal wounds or other large or incisional wounds, either as a result of surgery, trauma, sterniotomies, fasciotomies, or other conditions, dehisced wounds, acute wounds, chronic wounds, subacute and dehisced wounds, traumatic wounds, flaps and skin grafts, lacerations, abrasions, contusions, burns, electrical burns, diabetic ulcers, pressure ulcers, stoma, surgical wounds, trauma and venous ulcers or the like.

As is used in this section or elsewhere in this specification, reduced or negative pressure levels, such as −X mmHg, represent pressure levels that are below standard atmospheric pressure, which corresponds to 760 mmHg (or 1 atm, 29.93 inHg, 101.325 kPa, 14.696 psi, etc.). Accordingly, a negative pressure value of −X mmHg reflects absolute pressure that is X mmHg below 760 mmHg or, in other words, an absolute pressure of (760−X) mmHg. In addition, negative pressure that is "less" or "smaller" than −X mmHg corresponds to pressure that is closer to atmospheric pressure (e.g., −40 mmHg is less than −60 mmHg). Negative pressure that is "more" or "greater" than −X mmHg corresponds to pressure that is further from atmospheric pressure (e.g., −80 mmHg is more than −60 mmHg).

The negative pressure range for some embodiments of the present disclosure can be approximately −80 mmHg, or between about −10 mmHg and −200 mmHg. Note that these pressures are relative to normal ambient atmospheric pressure. Thus, −200 mmHg would be about 560 mmHg in practical terms. In some embodiments, the pressure range can be between about −40 mmHg and −150 mmHg. Alternatively, a pressure range of up to −75 mmHg, up to −80 mmHg or over −80 mmHg can be used. Also in other embodiments a pressure range of below −75 mmHg can be used. Alternatively, a pressure range of over approximately −100 mmHg, or even −150 mmHg, can be supplied by the negative pressure apparatus. In some embodiments, the negative pressure range can be as small as about −20 mmHg or about −25 mmHg, which may be useful to reduce fistulas. In some embodiments of wound closure devices described here, increased wound contraction can lead to increased tissue expansion in the surrounding wound tissue. This effect may be increased by varying the force applied to the tissue, for example by varying the negative pressure applied to the wound over time, possibly in conjunction with increased tensile forces applied to the wound via embodiments of the wound closure devices. In some embodiments, negative pressure may be varied over time for example using a sinusoidal wave, square wave, and/or in synchronization with one or more patient physiological indices (e.g., heartbeat).

Examples of such applications where additional disclosure relating to the preceding descriptions may be found include U.S. Pat. No. 8,235,955, titled "Wound treatment apparatus and method," issued Aug. 7, 2012 and U.S. Pat. No. 7,753,894, titled "Wound cleansing apparatus with stress," issued Jul. 13, 2010. Both applications are hereby incorporated by reference in their entirety. Other applications that may contain teachings relevant for use with the embodiments described in this section or elsewhere in this specification may include application Ser. No. 12/886,088, titled "Systems And Methods For Using Negative Pressure Wound Therapy To Manage Open Abdominal Wounds," filed Sep. 20, 2010, published as US 2011/0213287; application Ser. No. 13/092,042, titled "Wound Dressing And Method Of Use," filed Apr. 21, 2011, published as US 2011/0282309; and application Ser. No. 13/365,615, titled "Negative Pressure Wound Closure Device," filed Feb. 3, 2012, published as US 2012/0209227, the entireties of each of which are hereby incorporated by reference. Still more applications that may contain teachings relevant for use with the embodiments described in this specification are application Ser. No. 13/942,493, titled "Negative Pressure Wound Closure Device," filed Jul. 15, 2013, published as US 2014/0180225; PCT App. No. PCT/US2013/050619, filed Jul. 16, 2013 titled "Negative Pressure Wound Closure Device," published as WO 2014/014871 A1; PCT App. No. PCT/US2013/050698, filed Jul. 16, 2013 titled "Negative Pressure Wound Closure Device," published as WO 2014/014922 A1; PCT App. No. PCT/IB2013/01555, titled "Devices and Methods for Treating and Closing Wounds with Negative Pressure," filed May 5, 2013, published as WO 2013/175309 A1; PCT App. No. PCT/US2014/025059, titled "Negative Pressure Wound Closure Device and Systems and Methods of Use in Treating Wounds with Negative Pressure," filed Mar. 12, 2014, published as WO 2014/165275 A1; and PCT App. No. PCT/GB2014/050746, "Compressible Wound Fillers and Systems and Methods of Use In Treating Wounds With Negative Pressure," filed Mar. 13, 2014, published as WO 2014/140578 A1, and "Negative Pressure Wound Closure Device," filed Oct. 21, 2014, and published as PCT/US2014/061627. The entireties of the aforementioned applications are each hereby incorporated by reference and should be considered part of the present specification.

It will be understood that throughout this specification in some embodiments reference is made to an elongate, elongated or longitudinal strip or strips. It is to be understood that these terms are to be broadly construed and refer in some embodiments to an elongate material having two parallel or substantially parallel faces, where in cross-section a thickness of the material as measured perpendicular to the faces is relatively smaller than a height of the material measured parallel to the faces. While in some embodiments the strips may be constructed from discrete lengths of material, in other embodiments the strips may simply refer to elongate portions of an overall structure having two parallel or substantially parallel faces. The strips in some embodiments have a rectangular or generally rectangular-shaped faces, wherein a length of the face is longer than the height of the face. In some embodiments, the length of the face may be more than 2 times, 4 times, 6 times, 8 times, 10 times, 12 times or more greater than the height of the face.

As used in this section or elsewhere in this specification, the term "horizontal," when referring to a wound, indicates a direction or plane generally parallel to the skin surrounding the wound. The term "vertical," when referring to a wound, generally refers to a direction extending perpendicular to the horizontal plane. The term "longitudinal," when referring to a wound, generally refers to a direction in the horizontal plane taken in a direction along which the wound is longest. The term "lateral," when referring to a wound, generally refers to a direction in the horizontal plane perpendicular to the longitudinal direction. The terms "horizontal," "vertical," "longitudinal," and "lateral" may also be used to describe the stabilizing structures and wound closure devices described throughout this specification. When describing these structures or devices, these terms should not be construed to require that the structures or devices necessarily be placed into a wound in a certain orientation, though in certain embodiments, it may be preferable to do so.

FIG. 1 illustrates an embodiment of a negative pressure treatment system 100 that comprises a wound packer 102 inserted into a wound 101. The wound packer 102 may comprise porous materials such as foam, and in some embodiments may comprise one or more embodiments of wound closure devices described in further detail in this section or elsewhere in this specification. In some embodiments, the perimeter or top of any wound closure device inserted into the wound 101 may also be covered with foam or other porous materials. A single drape 104 or multiple drapes may be placed over the wound 101, and is preferably adhered or sealed to the skin on the periphery of the wound 101 so as to create a fluid-tight seal. An aperture 106 may be made through the drape 104 which can be manually made or preformed into the drape 104 so as to provide a fluidic connection from the wound 101 to a source of negative pressure such as a pump 110. Preferably, the fluidic connection between the aperture 106 and the pump 110 is made via a conduit 108. In some embodiments, the conduit 108 may comprise a RENASYS® Soft Port™, manufactured by Smith & Nephew. Of course, in some embodiments, the drape 104 may not necessarily comprise an aperture 106, and the fluidic connection to the pump 110 may be made by placing the conduit 108 below the drape. In some wounds, particularly larger wounds, multiple conduits 108 may be used, fluidically connected via one or more apertures 106.

In some embodiments, the drape 104 may be provided with one or more corrugations or folds. Preferably, the corrugations are aligned along the longitudinal axis of the wound, and as such may support closure of the wound by preferentially collapsing in a direction perpendicular to the longitudinal axis of the wound. Such corrugations may aid in the application of contractile forces parallel to the wound surface and in the direction of wound closure. Examples of such drapes may be found in application Ser. No. 12/922,118, titled "Vacuum Closure Device," filed Nov. 17, 2010 (published as US 2011/0054365), which is hereby incorporated by reference in its entirety.

In use, the wound 101 is prepared and cleaned. In some cases, such as abdominal wounds, a non- or minimally-adherent organ protection layer (not illustrated) may be applied over any exposed viscera. The wound packer 102 is then inserted into the wound, and is covered with the drape 104 so as to form a fluid-tight seal. A first end of the conduit 108 is then placed in fluidic communication with the wound, for example via the aperture 106. The second end of the conduit 108 is connected to the pump 110. The pump 110 may then be activated so as to supply negative pressure to the wound 101 and evacuate wound exudate from the wound 101. As will be described in additional detail below and in relation to the embodiments of the foregoing wound closure devices, negative pressure may also aid in promoting closure of the wound 101, for example by approximating opposing wound margins.

Any structure or component disclosed herein this section or elsewhere in the specification may comprise a radiopaque material. A radiopaque material advantageously allows a clinician to more easily find pieces of the wound closure device that may have come loose from the structure and become lost in the wound. Some examples of radiopaque materials include barium sulfate, bismuth trioxide, bismuth subcarbonate, bismuth oxychloride, and tungsten.

Stabilizing Structures and Wound Closure Devices of FIG. 2A-3E

Figure 2A:
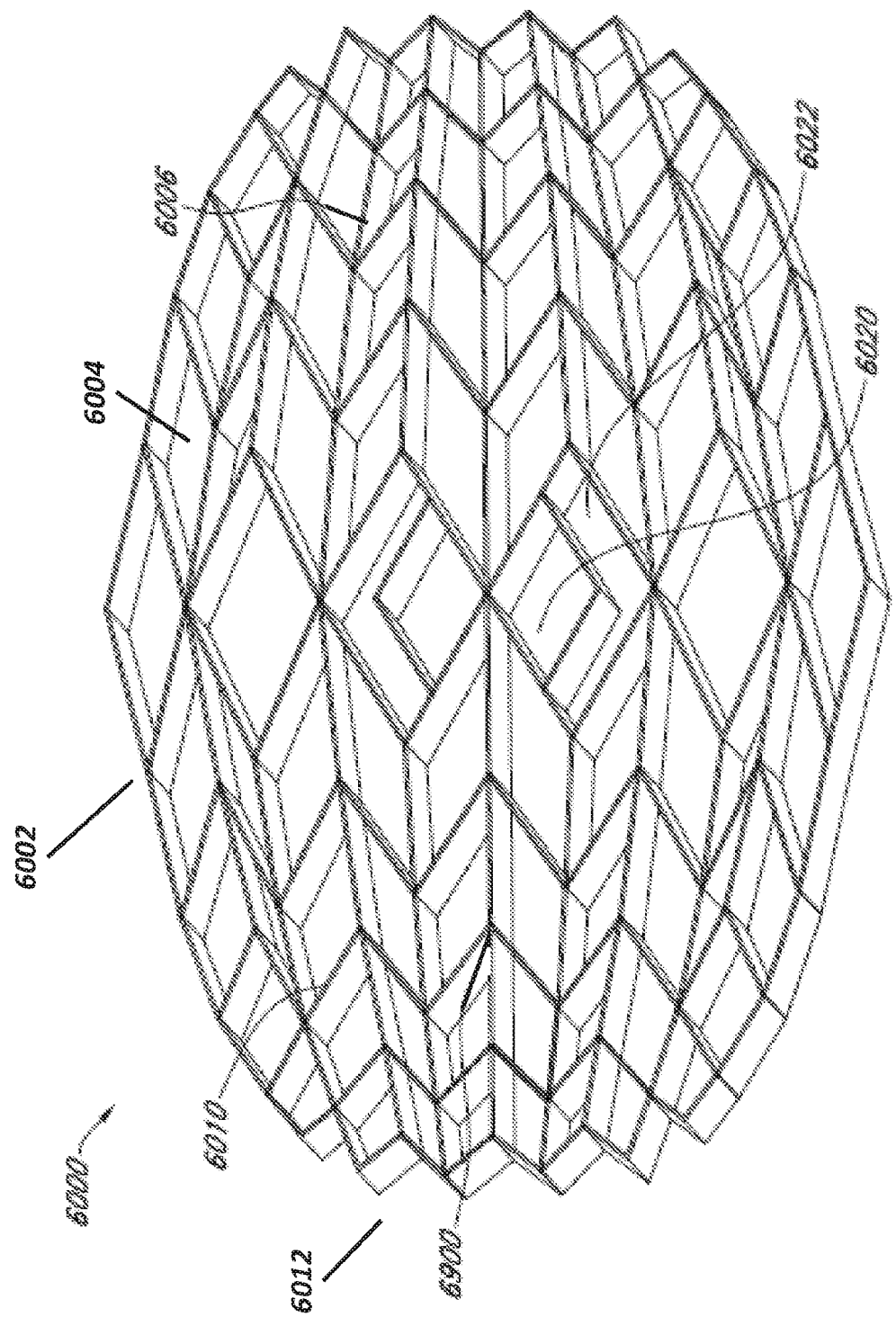
FIGS. 2A-C illustrate multiple views of an embodiment of a stabilizing structure.

FIG. 2A is a drawing of an embodiment of a stabilizing structure 6000 comprising a plurality of elongate strips 6006 arranged in parallel or semi-parallel, whose longitudinal length can be aligned with the longitudinal axis of a wound. In embodiments, the elongate strips 6006 may also be arranged in a non-parallel fashion. The various cells within this stabilizing structure 6000 may have a variety of shapes and sizes. As will be described in greater detail below, the length and shape of the elongate strips 6006, intervening members 6010, and cells 6004 may be designed so as to facilitate greater closure of the stabilizing structure. In certain embodiments, the junctions 6900 between the elongate strips and intervening members may be thinned to better facilitate rotation and closure of the stabilizing structures. In some embodiments, the stabilizing structure is tearable, such that the structure may be shaped into the shape of a wound. As described elsewhere in the specification, tears may be completed at the intersections between intervening members and elongate strips or at any suitable location along the elongate strip or intervening member.

All stabilizing structures described herein this section or elsewhere in the specification may be fashioned to accommodate any size of wound. However, to better accommodate the needs of the clinical environment, in certain embodiments, the stabilizing structures described herein may be provided in a pack of two sizes, one smaller stabilizing structure and one larger stabilizing structure about 1.25 times as larger, about 1.5 times as large, about 1.75 times as large, about 2 times as larger, about 2.5 times as larger, about 3 times as large, about 4 times as large, about 5 times as large, or more than about 5 times as large. In some embodiments, the pack may comprise more than two sizes, such as three sizes, four sizes, five sizes, or more than five sizes. The stabilizing structures within the pack may be of a variety of sizes in relation to one another such as the ratios described above.

In certain embodiments, the stabilizing structure 6000 can collapse in any manner described in this section or elsewhere in this specification with or without the application of negative pressure. For example, the stabilizing structure may collapse significantly more in one plane than in another plane upon application of negative pressure. In some embodiments, the stabilizing structure is configured to collapse more in a horizontal plane parallel to the length and width of the stabilizing structure than in a vertical plane perpendicular to the horizontal plane. In embodiments, particular rows may collapse in a first direction, while another row may collapse in the same or an opposing direction. In certain embodiments, the stabilizing structure may collapse along the width of the stabilizing structure while remaining relatively rigid along the length of the stabilizing structure and in the vertical direction.

The stabilizing structure may be comprised of any materials described in this section or elsewhere in this specification, including: flexible plastics such as silicone, polyurethane, rigid plastics such as polyvinyl chloride, semi-rigid plastics, semi-flexible plastics, biocompatible materials, composite materials, metals, and foam. In certain embodiments, the stabilizing structure may comprise a radio opaque material, to more readily allow a clinician to find pieces of the stabilizing structure within the wound.

Returning to FIG. 2A, stabilizing structure 6000 may have an outer perimeter that defines an at least partially elliptical shape. As described above, stabilizing structure 6000 may comprise a plurality of cells 6004 provided side-by-side, each cell defined by one or more walls, each cell having a top end and a bottom end with an opening extending through the top and bottom ends. As with the other stabilizing structures described herein this section and elsewhere in the specification, the stabilizing structure 6000 is configured to collapse by collapsing one or more cells 6004. In some embodiments, the cells are all of the same approximate shape and size; however, in other embodiments, the cells are of different shapes and sizes. In some embodiments, the stabilizing structures as described herein this section or elsewhere in the specification may be domed, such that the central portion of the stabilizing structure bulges upward. For example, a lower portion of the stabilizing structure may be concave, while an upper portion of the stabilizing structure is convex.

The elongate strips 6006 may be made from one single material, such as those described elsewhere in the specification, or the elongate strips may be made from multiple materials. For example, elongate strips 6006 may comprise sections of more rigid material and sections of more flexible material. The elongate strips 6006 may be curved along their length so as to facilitate the curved outer perimeter of the stabilizing structure 6000. The elongate strips may be curved along their lengths outward away from a center of the stabilizing structure 6000. The arch of the curves of the elongate strips 6006 may vary considerably, with some strips 6006 being highly curved while other are minimally curved or even straight.

Similarly, the stabilizing structure 6000 can further comprise a plurality of intervening members 6010 connected to the elongate strips 6006. The intervening members 6010 may all be of a similar shape and size or they may be of a variety of shapes and sizes. The intervening members may be constructed from any material disclosed herein this section or elsewhere in the specification. Further, the intervening members may be constructed from multiple materials.

Advantageously, the elliptical shape of stabilizing structure 6000 may allow the structure to better accommodate the shape of the wound. Most wounds are in shapes that are rounded, thus, an elliptically shaped stabilizing structure 6000 may better fit into a wound.

In embodiments, the outer perimeter 6002 may have a reduced edge 6012 so as to facilitate collapse of the stabilizing structure. By removing mass of the stabilizing structure at reduced edge 6012, the stabilizing structure can collapse more freely at reduced edge 6012, thus allowing for a better fit within the wound. Further, by reduced the mass at reduced edge 6012, there may be less pinching of the surrounding tissue during and after collapse of the stabilizing structure 6000.

The stabilizing structure 6000 and all stabilizing structures and wound closure devices described in this section or elsewhere in this specification can collapse on a variety of timescales in a dynamic fashion. In certain embodiments, the majority of the collapse may occur within the first few minutes upon application of negative pressure. However, after the initial collapse, the stabilizing structure or wound closure device may continue to collapse at a much slower rate, thereby applying increasing longitudinal tension over a long period of time and drawing the edges of the wound closer together. By slowly drawing the wound edges closer together over time, the stabilizing structure or wound closure device allows the surrounding healing tissue to remodel synergistically with the closure of the device or stabilizing structure. Slow, dynamic wound closure may allow the surrounding tissue to heal at an accelerated rate, because the collapsing structure or device slowly brings the edges of the wound closer together without stressing the newly formed or weakened tissue too quickly.

In some embodiments, the stabilizing structures described in this section or elsewhere in this specification can be placed into a wound for a period of time and then removed or replaced with another stabilizing structure. For example, a stabilizing structure could be inserted into a wound for a period of time, promoting closure of the wound by drawing the edges closer together. After a period of time has passed, the stabilizing structure can be replaced by a stabilizing structure of a different size or collapsibility, for example a stabilizing structure of a smaller size or decreased density. This process could be repeated over and over, thereby continuously drawing the edges of the wound together over time and allowing for continuing repair and remodeling of the surrounding tissue. In certain embodiments, the stabilizing structure is configured to remain in the wound for at least about less than 1 hour, at least about 1 hour, at least about 2 hours, at least about 4 hours, at least about 6 hours, at least about 8 hours, at least about 12 hours, at least about 24 hours, at least about 2 days, at least about 4 days, at least about 6 days, at least about 1 week, at least about 2 weeks, at least about 3 weeks, or more than 3 weeks.

In certain embodiments, up to 90% of the collapse of the stabilizing structure or wound closure device may occur within the first few minutes upon application of negative pressure, while the remaining 10% of the collapse may occur slowly over a period of many minutes, hours, days, weeks, or months. In other embodiments, up to about 80% of the collapse, up to about 70%, up to about 60%, up to about 50%, up to about 40%, up to about 30%, up to about 20%, up to about 10%, or about 0% of the collapse will occur immediately within the first few minutes upon application of negative pressure while the remainder of the collapse occurs at a much slower rate such as over the course of many minutes, hours, days weeks, or months. In other embodiments, the stabilizing structure can collapse at a variable rate. In some embodiments, the entirety of the collapse occurs at a slowed rate, while in other embodiments the entirety of the collapse occurs almost immediately within the first few minutes. In further embodiments, the collapse can occur at any rate and the rate can vary over time. In certain embodiments, the rate of collapse can be altered in a variable fashion by adding and/or removing portions of the structure or by controlling the application of negative pressure and irrigant fluid.

Returning to FIG. 2A, in some embodiments, the pattern of the stabilizing structure 6000 is designed in such a way as to facilitate maximum closure of the stabilizing structure. Preferably, maximum closure is in a direction perpendicular to the length of the elongate members and within the horizontal plane. As will be described in greater detail below, greater closure may be achieved by varying the length of the elongate strips 6006, the length of the intervening members 6010, and the shape of the cells 6004. The shape of the cells 6004 may comprise any shape described herein this section or elsewhere in the specification. For example, as depicted in FIG. 2A, the cells 6004 may be diamond-shaped or parallelepiped with smaller diamond-like shapes 6020 located within larger diamonds 6022. Such a construction may provide greater overall closure of the stabilizing device 6000 to provide for maximum closure of the wound. Additionally, the smaller diamond-like shapes 6020 located within larger diamonds 6022 can spread the load over a greater area reducing the chance of damage to the tissue structures below the matrix. This construction can also reduce the likelihood of the foam or the drape being pulled into the matrix and preventing closure of the wound.

Figure 2B:
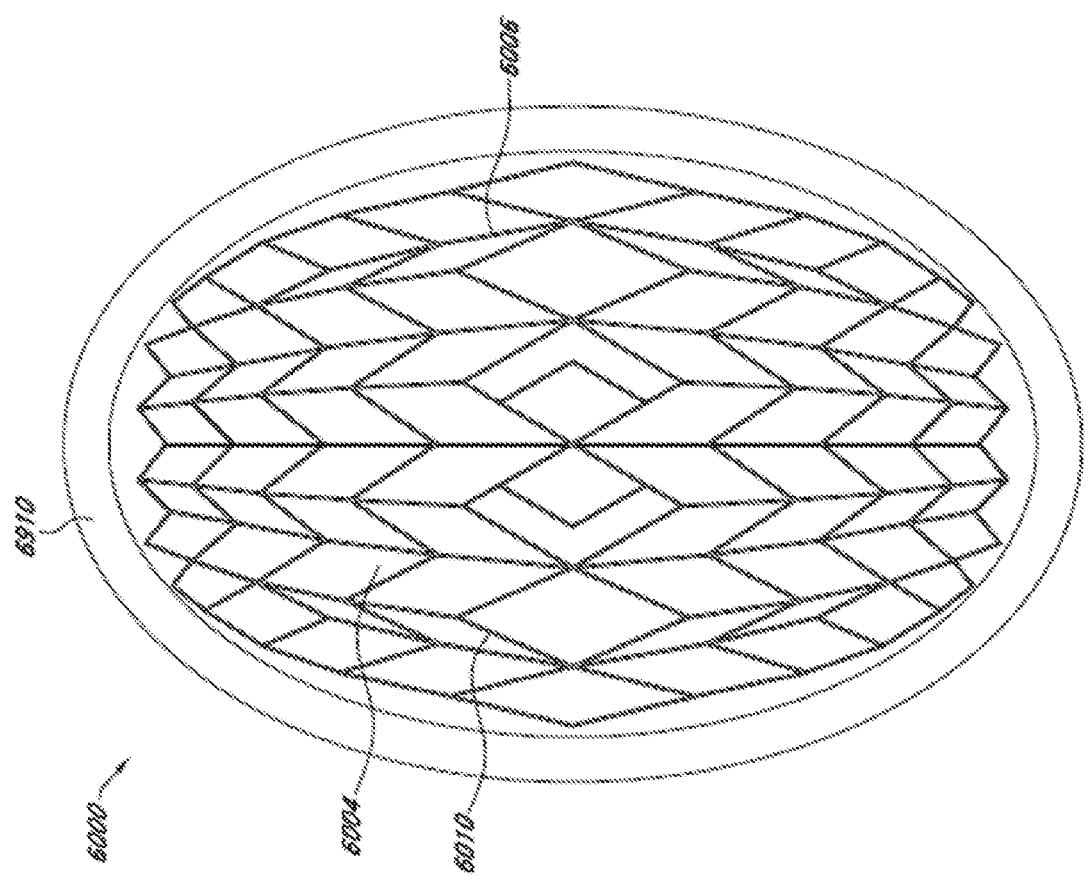
Figure 2C:
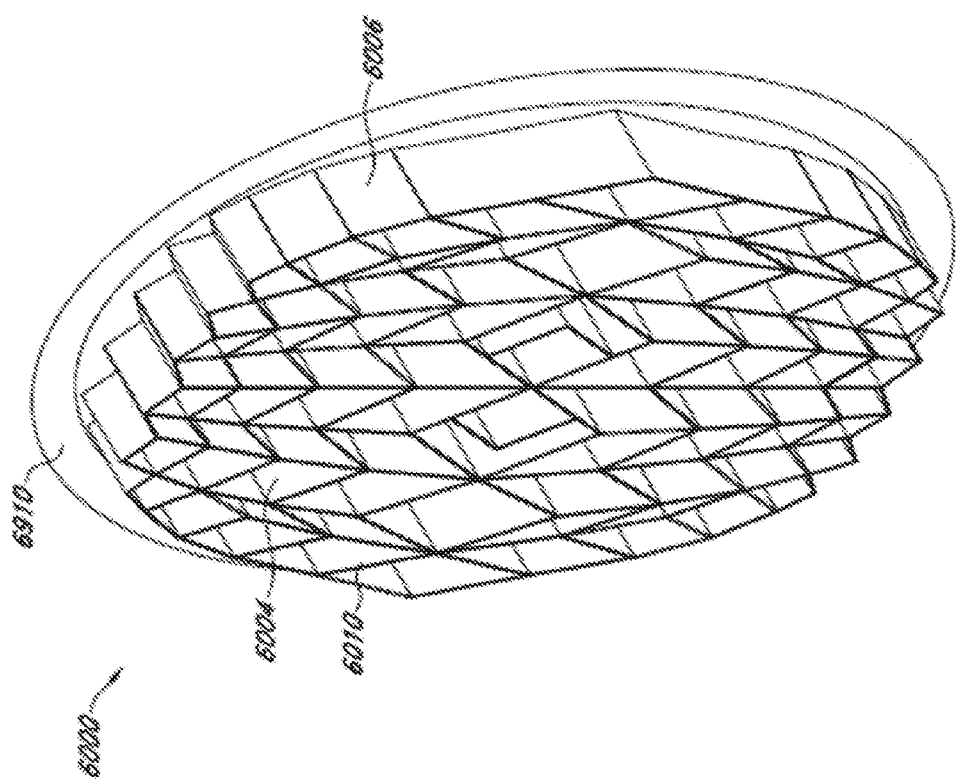

FIGS. 2B-C are illustrations of different views of the stabilizing structure embodiment of FIG. 2A. As described above in relation to FIG. 2A, the stabilizing structure comprises cells 6004, intervening members 6010, and elongate strips 6006; however, here a simulated shape of a wound 6910 is also included for comparison.

Any of the stabilizing structures described herein this section or elsewhere in the specification may be constructed from any suitable means. For example, the stabilizing structures may be constructed via molding or may be printed directly using 3D printing technology. In certain embodiments, the stabilizing structures of FIGS. 2A-C may be constructed from a single polymer via 3D printing. In some embodiments, the stabilizing structures may be constructed from one polymer, two polymers, three polymers, or more than three polymers. The stabilizing structures may be constructed from any material disclosed herein this section or elsewhere in the specification. The stabilizing structure can be made by cutting the structure out of a solid block of material. Methods used for cutting can include, for example, water jet cutting, laser cutting, or die cutting. The stabilizing structures may be cut to size along the walls of the cells 6004. For example, the intervening members along the outside face of elongate strips 6006 can be cut off to appropriately size the stabilizing structure. The stabilizing structure may be cut along the walls, along any portions of the elongate strips, and/or along any portions of the intervening members.

In some embodiments, the stabilizing structure 6000 of FIGS. 2A-C can be configured to include perforations or detachable sections that allow portions of the device to separate from the remainder of the device. For example, perforations may be incorporated into the joints 6900 between various cells 6004 contained within the stabilizing structure 6000, allowing for the removal of individual rows or cells to alter the shape of the stabilizing structure 6000.

Applicable to all stabilizing structures or wound closure devices described in this section or elsewhere in the specification, the stabilizing structure or wound closure device may be tearable such that the stabilizing structure may be shaped into the shape of a wound. In some embodiments, the stabilizing structure may be torn at the intersections between intervening members and elongate strips, while in further embodiments, the elongate strips or intervening members may be torn at any suitable position.

Figure 3A:
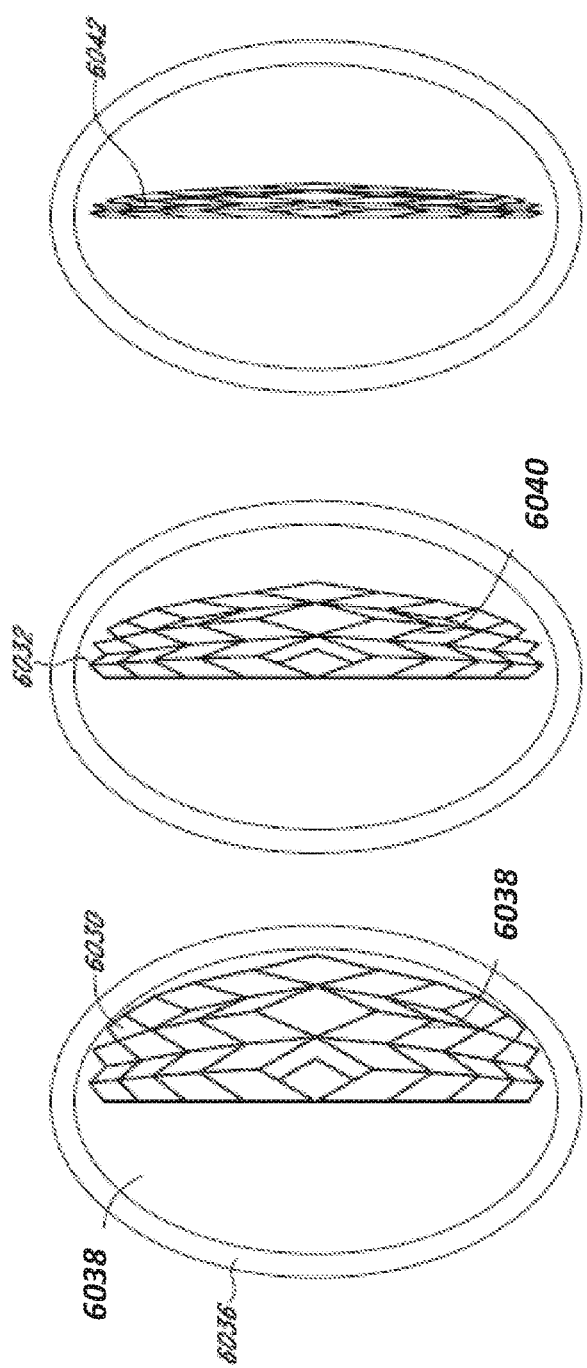
FIGS. 3A-E illustrate multiple views of another embodiment of a stabilizing structure and a method of creating the stabilizing structure.

FIGS. 3A-E depict methodologies for generating the design of a stabilizing structure, such as the stabilizing structures of FIGS. 2A-C. To facilitate various types of closure (for example, maximum closure) the shape, size, and location of the elongate strips, intervening members, and cells may be determined via various methods. For example, as depicted in FIG. 3A, each collapsible cell 6030 has four sides, and each intersection between an intervening member(s) and/or elongated strip(s) may be modeled via pin-joints 6032. Further, the entirety of stabilizing structure 6034 may be modeled inside of an oval wound model 6036. As depicted in FIG. 3A, the stabilizing structure 6034 may be modeled to collapse from an open state 6038 to a semi-collapsed state 6040, to a fully collapsed state 6042. In some clinical scenarios, maximum closure down to a completely flattened stabilizing structure may be desirable to maximize wound closure by drawing the edges of the wound as close together as possible.

Figure 3B:
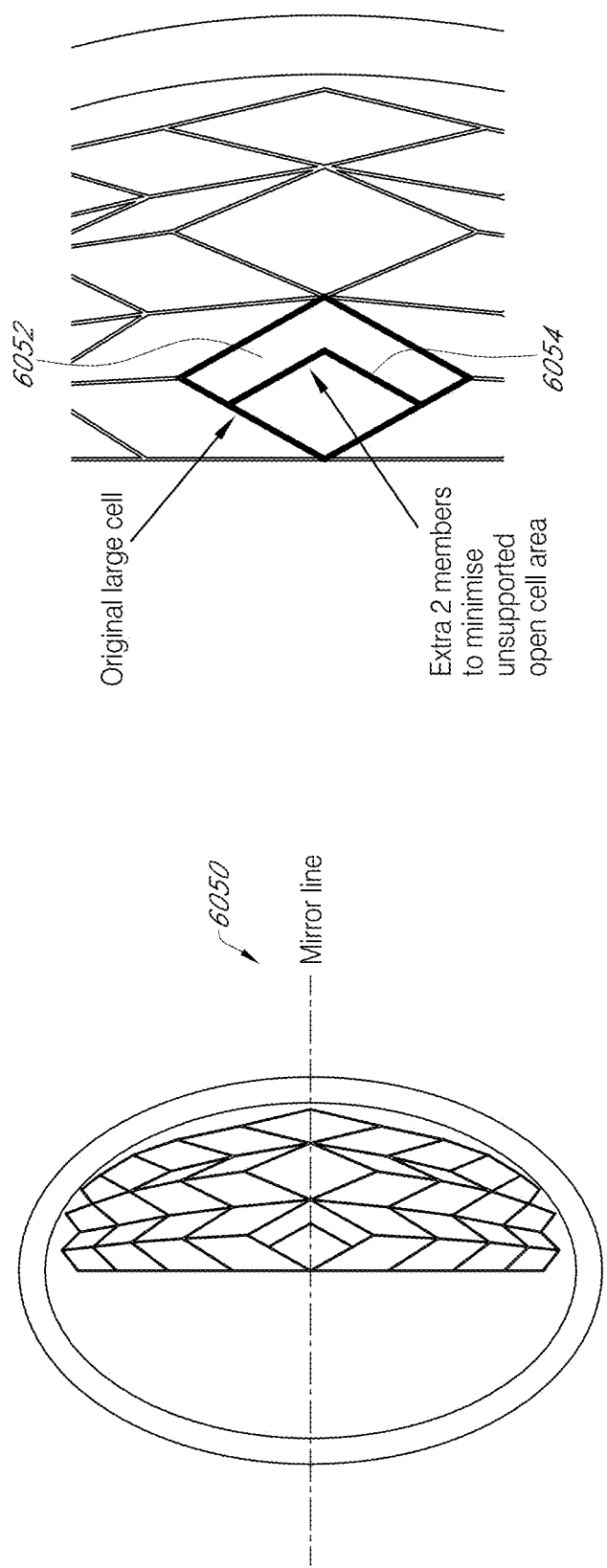

As illustrated in FIG. 3B, in certain embodiments, the process of determining the optimal shape, size, and location of the elongate strips, intervening members, and cells for wound closure may be facilitated by modeling the stabilizing structure as a mirrored pattern on opposite sides of a mirror line 6050 (which may also be referred to as the transverse axis, perpendicular to a longitudinal axis of the stabilizing structure), thereby making the curve and collapse of the stabilizing structure symmetrical. The mirror axis may be along the minor axis or it may be along the major axis of the stabilizing structure. Alternatively, the mirror line may be located in any suitable location within the stabilizing structure, such as diagonally across the stabilizing structure. In certain embodiments, this method may lead to large diamond-shaped cells near the center line. These large diamond-shaped structures 6052 may be further subdivided to further support the stabilizing structure by including smaller diamond shapes 6054 within larger shapes. In some embodiments, these smaller shapes 6054 within a larger shape 6052 may comprise any shape disclosed herein this section or elsewhere in the specification. The larger cells may be further subdivided by two smaller shapes, three smaller shapes, four smaller shapes, or more than four smaller shapes. It will be understood by one of skill in the art that the mirror line need not be confined to a line perpendicular to the longitudinal orientation of the wound. Instead, the mirror line may be located along the longitudinal axis of the wound or at an angle to the longitudinal axis of the wound. In some embodiments, the stabilizing structure may contain multiple mirror lines, thereby having multiple subsections that are symmetrical or different.

Figure 3C:
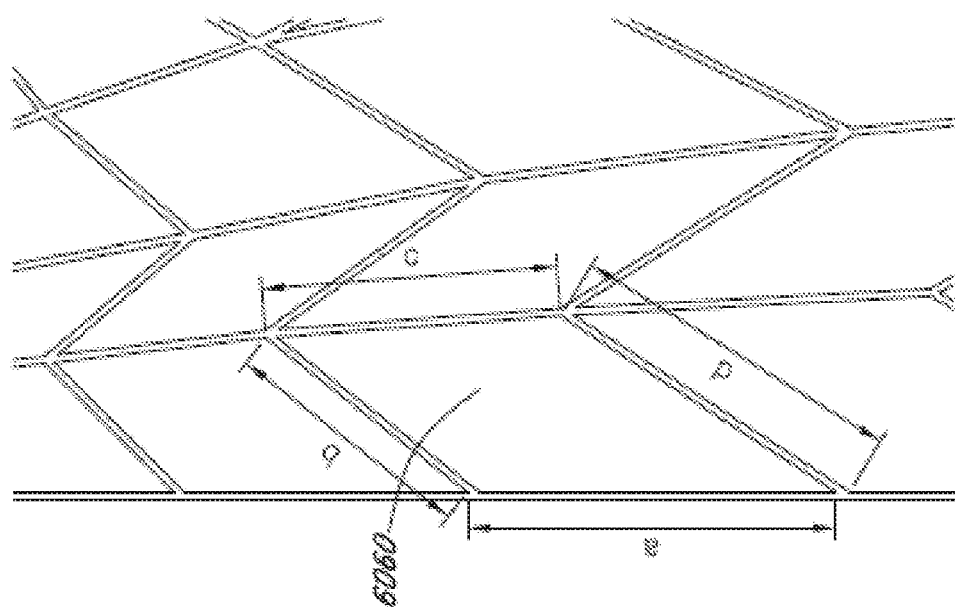

As illustrated in FIG. 3C, for a four-sided cell to collapse, it must follow a simple formula: a+b=c+d, where a, b, c, and d are the lengths of individual sides of a single cell within the stabilizing structure such as the cell 6060 of FIG. 3C. When members c and b collapse together, then d and a collapse together. Such a formula may be the basis for developing a pattern for a stabilizing structure that maximizes collapsibility.

Figure 3D:
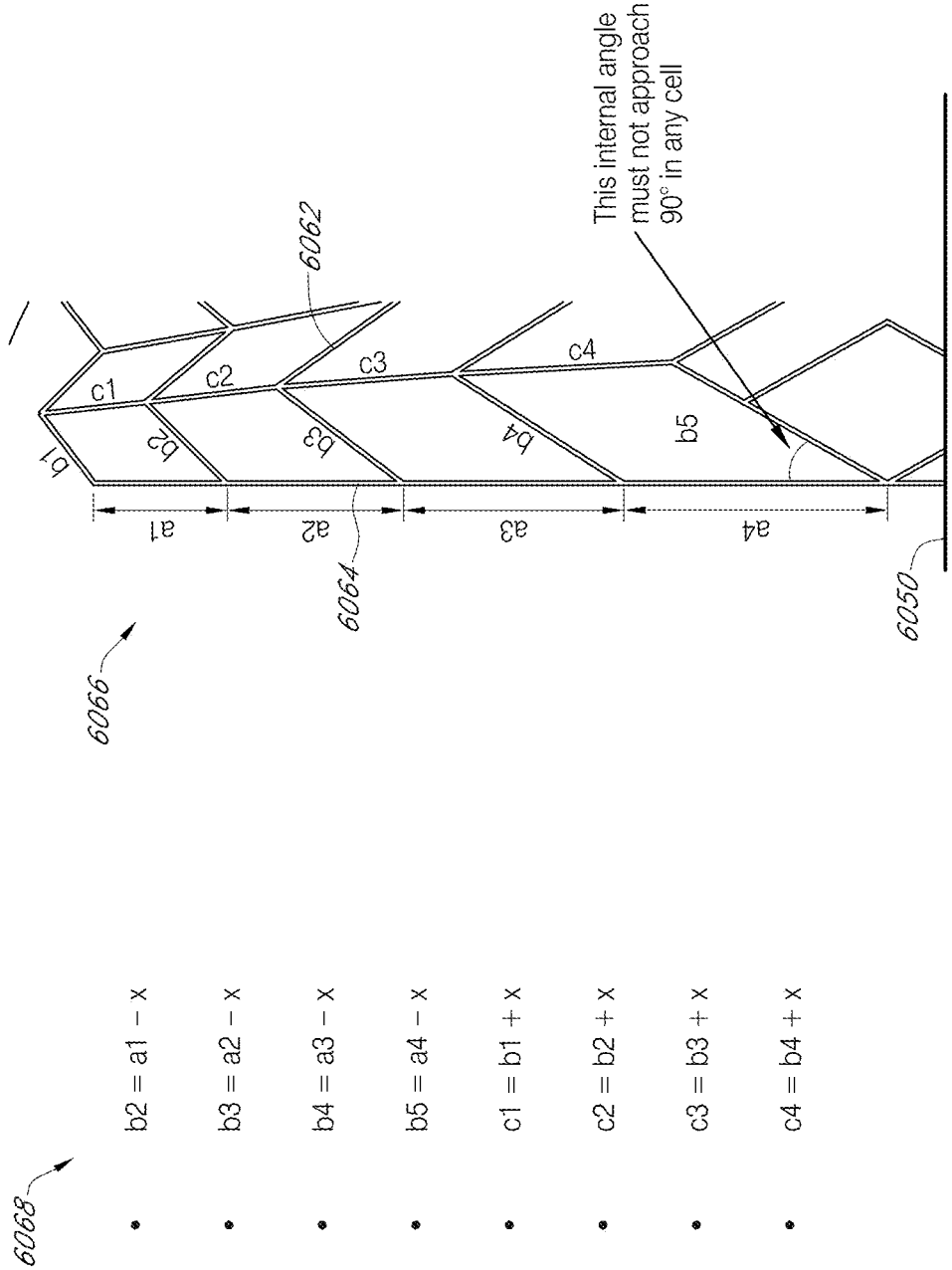
Figure 3E:
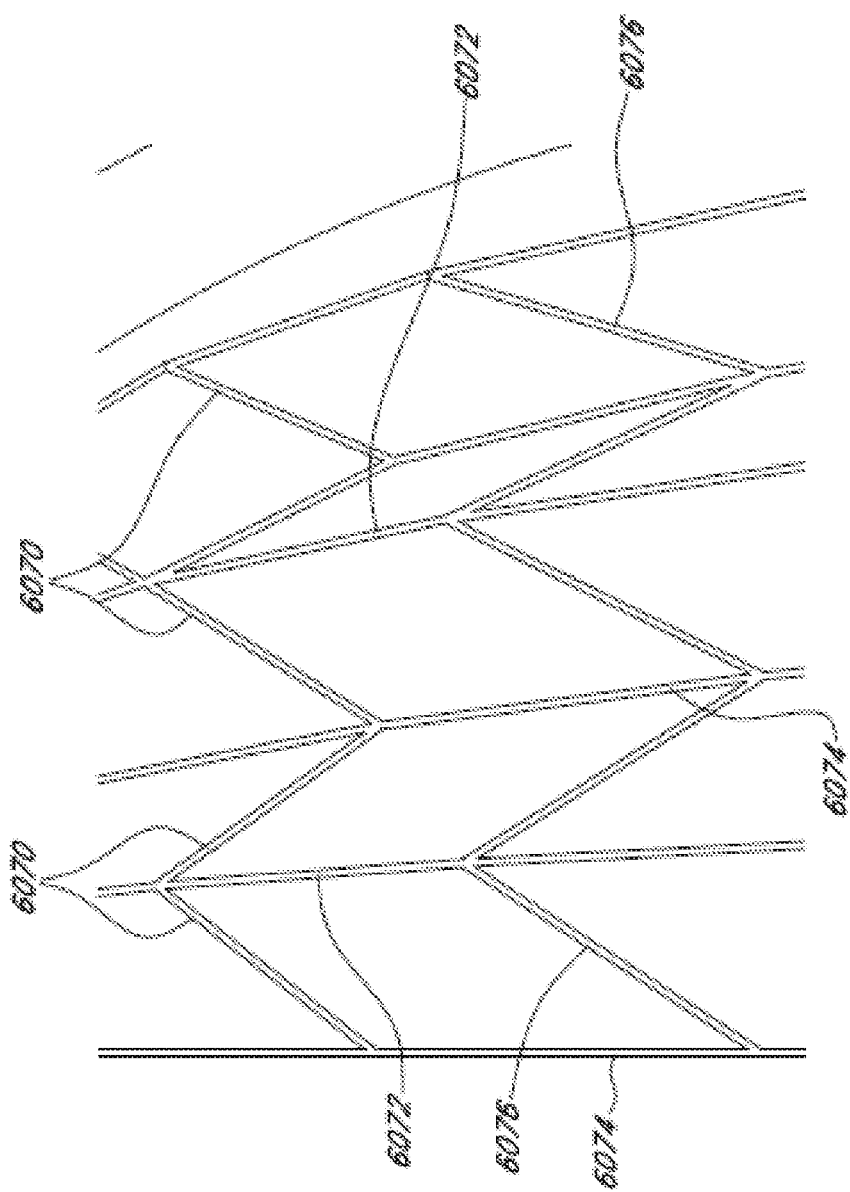

FIG. 3D illustrates an expansion of the concept described in FIG. 3C. By using the base formula a+b=c+d, the elongate strips were progressively lengthened (a4>a3>a2>a1) towards the horizontal mirror line 6050, thereby achieving a curve in the stabilizing structure while preventing any of the intervening members 6062 from becoming perpendicular to the elongate strips 6064 (i.e. having an internal angle of 90 degrees). As illustrated in FIG. 3D, a value for b1 may be chosen, at which point an arbitrary offset value x may also be chosen to ease the construction of the various cell geometries. Using the progressive values for a1 through a4, illustrated visually in FIG. 3D 6066, values for b1-b4 may be calculated 6068. Using calculated values derived from equations 6068 for the various walls of the individual cells allows for the design of a stabilizing structure that collapses completely, such as those depicted in FIGS. 3A-B.

In some embodiments, a method for generating a stabilizing structure design may include steps to speed up the initial geometry construction. For example if all members from left to right in a specific row, as visualized by intervening walls 6070, 6076 in FIG. 3E, a pattern then emerges where alternating vertical members are also the same length. Walls of the same length are indicated by their respective labels 6070, 6072, 6074, and 6076. Once the initial design is generated then individual cells may be modified by lengthening, shortening, removing or inserted according to the formulas of FIG. 3D to achieve the desired shape of the overall stabilizing structure.

The Anchoring Layers of FIGS. 4-6B

Figure 4:
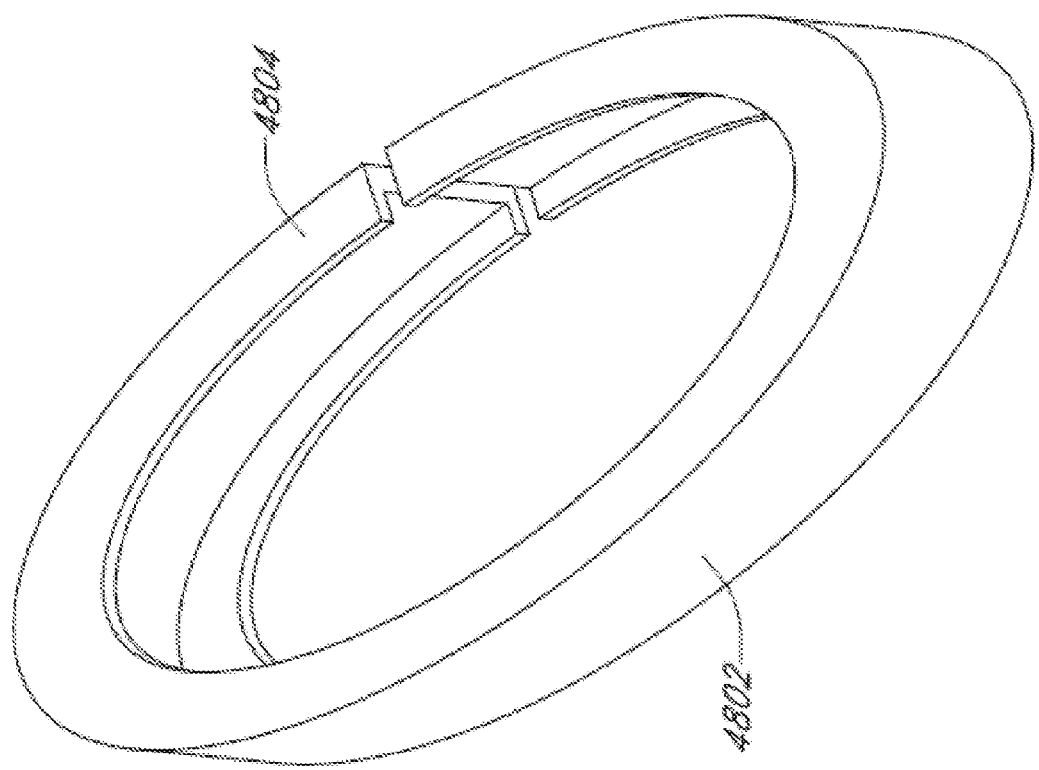
FIG. 4 illustrates an embodiment of a ring that can surround a stabilizing structure.

FIG. 4 illustrates an embodiment of an anchoring layer 4800 that may surround the stabilizing structures as described in this section or elsewhere in this specification. The ring 4800 can comprise a layer of tissue anchors 4802 configured to grip the surrounding edges of a wound. For example, the tissue anchors can be hooks, barbs, prongs, or other structures that serve to attach to the tissue of a wound. In certain embodiments, the tissue anchors comprise hook and loop fasteners such as those used in Velcro technologies. In certain embodiments, the ring 4800 can be comprised of foam, such as those described previously or the ring can be comprised of a combination of a foam layer and a tissue anchor layer 4802. A lip 4804 may extend inward from the ring 4800 and serve to overlap the top and/or the bottom of a stabilizing structure as described in this section or elsewhere in this specification, thereby securing the ring 4800 around the stabilizing structure.

FIGS. 5A-D are photographs of a wound closure device 5000 according to another embodiment. The wound closure device 5000 comprises a stabilizing structure 5002 which may be similar to the structures described in FIGS. 2A-3E, or may comprise any of the stabilizing structures described elsewhere in this specification. The stabilizing structure 5002 may optionally be surrounded by a porous layer 5004 such as a layer of foam, and the porous layer may be surrounded by an anchoring layer 5006 comprising tissue anchors such as those anchors produced by Velcro industries, various barbs and/or various hooks. In certain embodiments, the porous layer may be in the form of a ribbon. The stabilizing structure 5002, porous layer 5004 and anchoring layer 5006 may be provided as separate components to be attached by the practitioner in use, or they may be pre-attached to each other.

Similar to the embodiments illustrated in FIGS. 2A-3E, the stabilizing structure 5002 can collapse in any manner described elsewhere in this specification, for example, horizontally. When the wound closure device 5000 is implanted, the surrounding tissues can be pressed against the tissue anchors to embed them within the tissue and anchor the device. In some embodiments, the wound closure device 5000 may be placed in a wound and sealed with a drape. Although the embodiments further described in this section comprise an anchor layer that surrounds a porous layer, other embodiments may omit the porous layer, such that the anchoring layer directly surrounds or is attached to the stabilizing structure.

In some embodiments, the anchoring layer 5006 comprises an elongate strip of material comprising a plurality of tissue anchors extending from a base layer 5007, wherein the tissue anchors can have different shapes and sizes as described elsewhere in the specification. The tissue anchors may extend from a first planar side of the elongate strip, and the second planar side of the elongate strip may comprise an adhesive covered by an adhesive backing layer. The structure of the anchors can have various forms depending on the tissue they are intended to bind. Longer anchors can be used for loosely bound tissues such as fat or connective tissue, while shorter anchors can be used for denser tissues such as muscle. In other embodiments, depending upon the shape of the anchor, shorter anchors may be more desirable for softer, fatty tissue, while longer anchors are utilized for denser tissues. Anchors with more rigid stems can be utilized to penetrate denser tissues. In some embodiments, anchors can have bilateral prongs that tend to collapse upon insertion in tissue and yet expand when pulled in an opposite direction such that a certain pulling force can be applied to tissue. The characteristics of the anchors or attachment mechanisms, and their resulting force profiles, can vary by a number of parameters, such as the length of the anchor, the shape of the attachment mechanisms, the structure of grasping features, the material(s) used for the attachment mechanisms, the relative flexibility/rigidity of the attachment mechanisms, and the spacing/density of the attachment mechanisms.

The anchors may have various lengths for optimal penetration of the surrounding tissue. For example, the length of the anchors may be at most about 0.01 mm, at most about 0.1 mm, at most about 0.2 mm, at most about 0.5 mm, at most about 1 mm, at most about 2 mm, at most about 3 mm, at most about 5 mm, at most about 10 mm, at most about 20 mm, at most about 30 mm, at most about 40 mm, at most about 50 mm, at most about 75 mm, at most about 100 mm, or more than 100 mm.

Figure 5A:
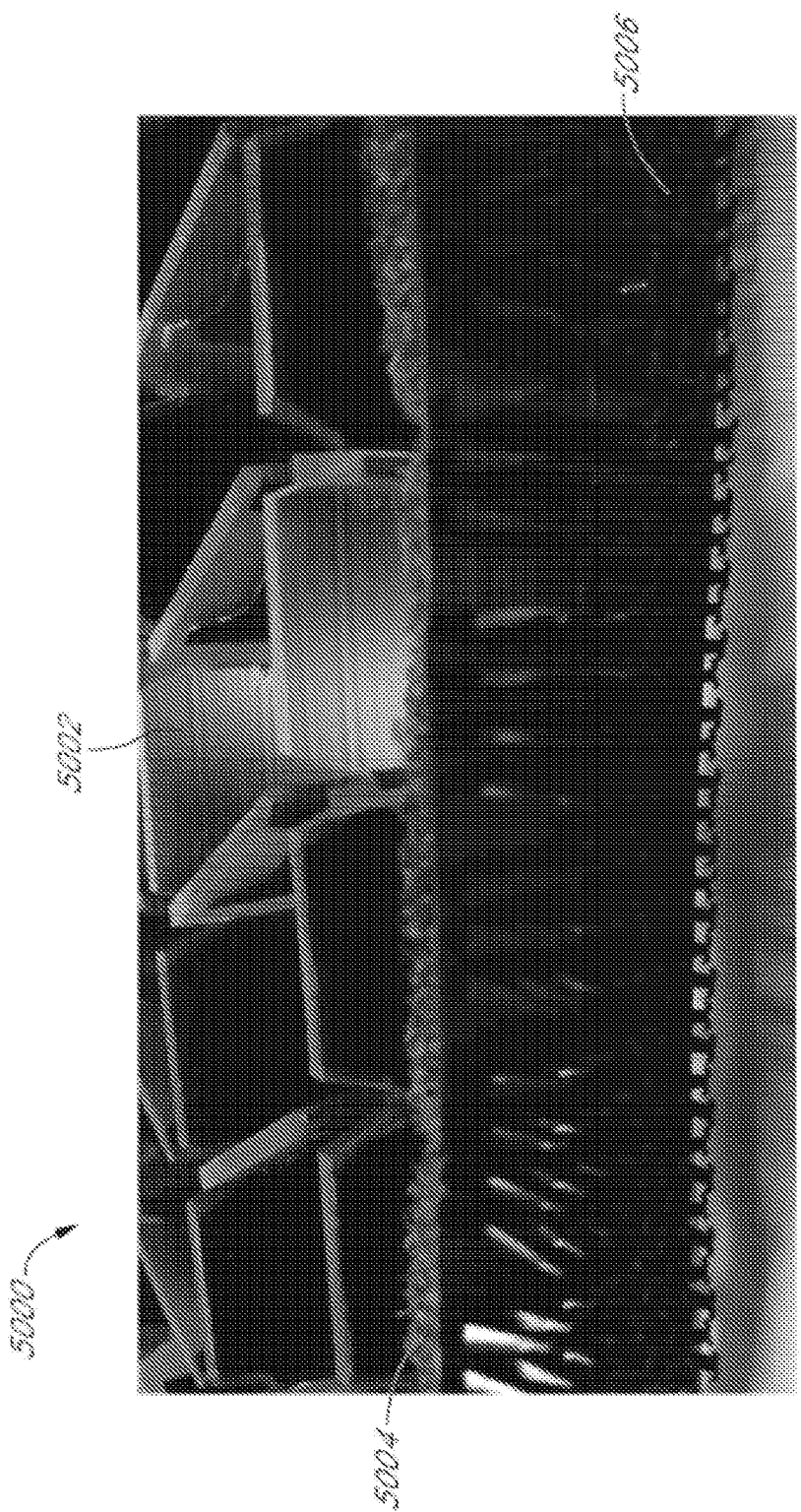
FIGS. 5A-D are photographs of embodiments of stabilizing structures with surrounding anchoring and foam layers.
Figure 5B:
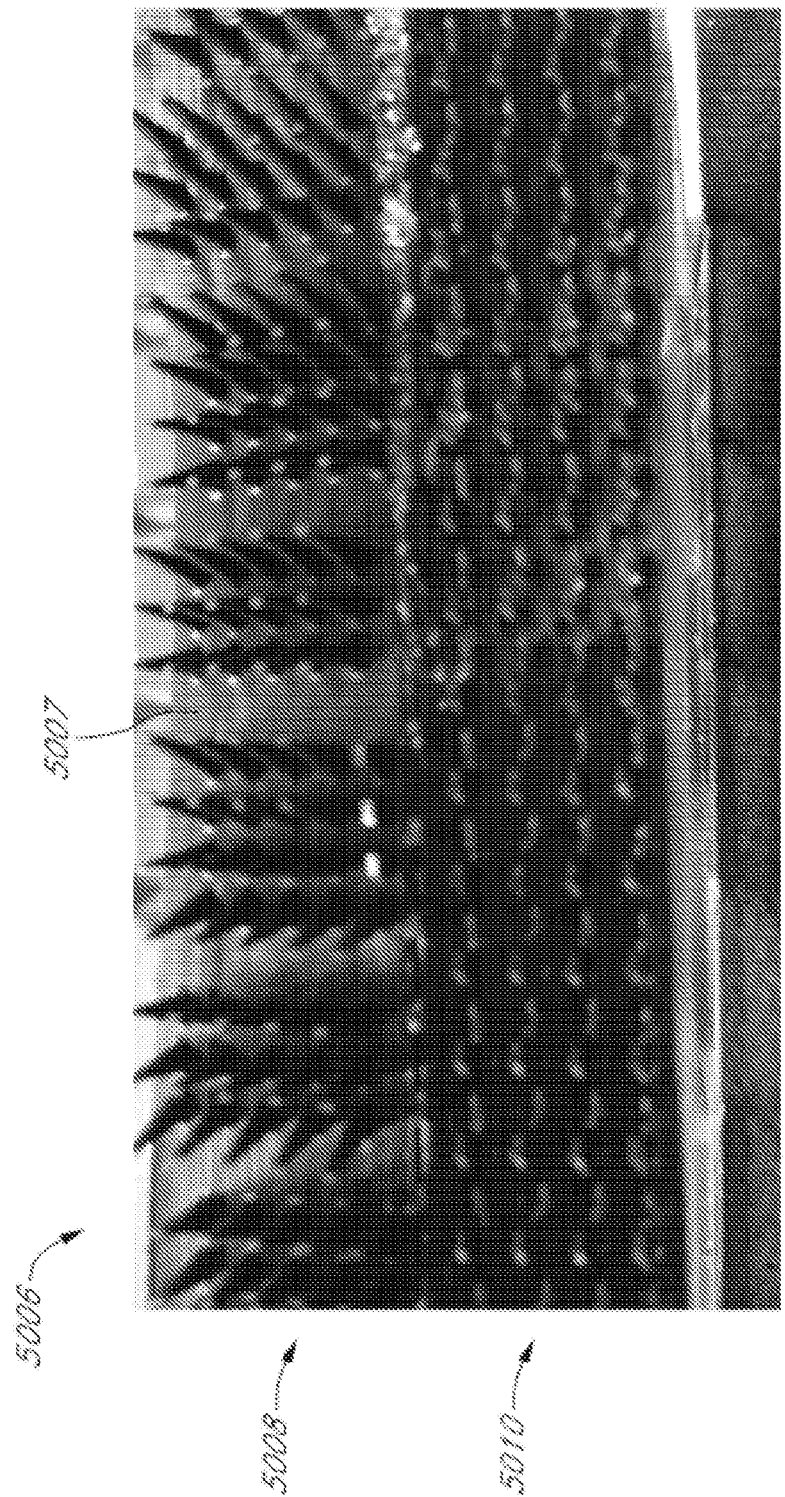

FIG. 5B is a photograph of a closer view of the anchoring layer 5006 of the wound closure device 5002 depicted in FIG. 5A. The anchoring layer may consist of a first band of longer anchors 5008 configured to surround the porous layer 5004 and stabilizing structure 5002, and a second band of shorter anchors 5010 configured to surround the porous layer 5004 and stabilizing structure 5002. As illustrated, the first band 5008 may be disposed above the second band 5010. In some embodiments, there may be additional alternating series of bands vertically relative to each other. In further embodiments, the different bands may have different anchor lengths and shapes, as disclosed herein this section and elsewhere in the specification. For example, instead of 2 types of bands with 2 types of anchors, there may be 3 types of bands with 3 types of anchors or 4 types of bands with 4 types of anchors and so on. Preferably, the anchors are selected for the appropriate tissue types. For example, returning to FIG. 5B, the first band 5008 may comprise longer anchors, desirable for penetration into the denser fascia, and thus may be positioned towards the bottom of the device. Similarly, the second band 5010 comprises shorter double hooks, desirable for penetration into denser tissue. Other suitable tissue anchors, as described elsewhere in this specification, include the hook and loop configuration of Velcro, barbs, hooks, spikes, pegs, arrowheads, or any suitable shape. Further examples of surfaces include textured surfaces, such as roughened sandpaper-like surfaces, or nano-textured surfaces that may facilitate tissue adhesion.

In some embodiments, the use of surface anchors can be used in combination with a surgical adhesive, providing a much stronger bond between tissue layers than the adhesive alone, and providing temporary adhesion while the adhesive sets. In some embodiments, the surgical adhesive can be added to the anchors themselves. In certain embodiments, the surgical adhesive may simply be applied between the anchors to coat at least a portion of the anchoring layer. In further embodiments, the anchors may be replaced with a surgical adhesive, and the surgical adhesive may act to anchor the device to the surrounding wound.

In certain embodiments, the anchors may be constructed from a variety of materials, including any materials disclosed elsewhere in the specification, such as: synthetic or natural polymers, metals, ceramics, or other suitable materials. The anchors may be constructed from biodegradable materials such as biodegradable synthetic or natural polymers. Non-limiting examples of biodegradable synthetic polymers include: polyesters such as polylactic acid or polyglycolic acid, polyanhydrides, and linear polymers with biodegradable linkages. Further, the anchors may be constructed of biodegradable biological materials, such as autografts, allografts, and/or xenografts.

Figure 5C:
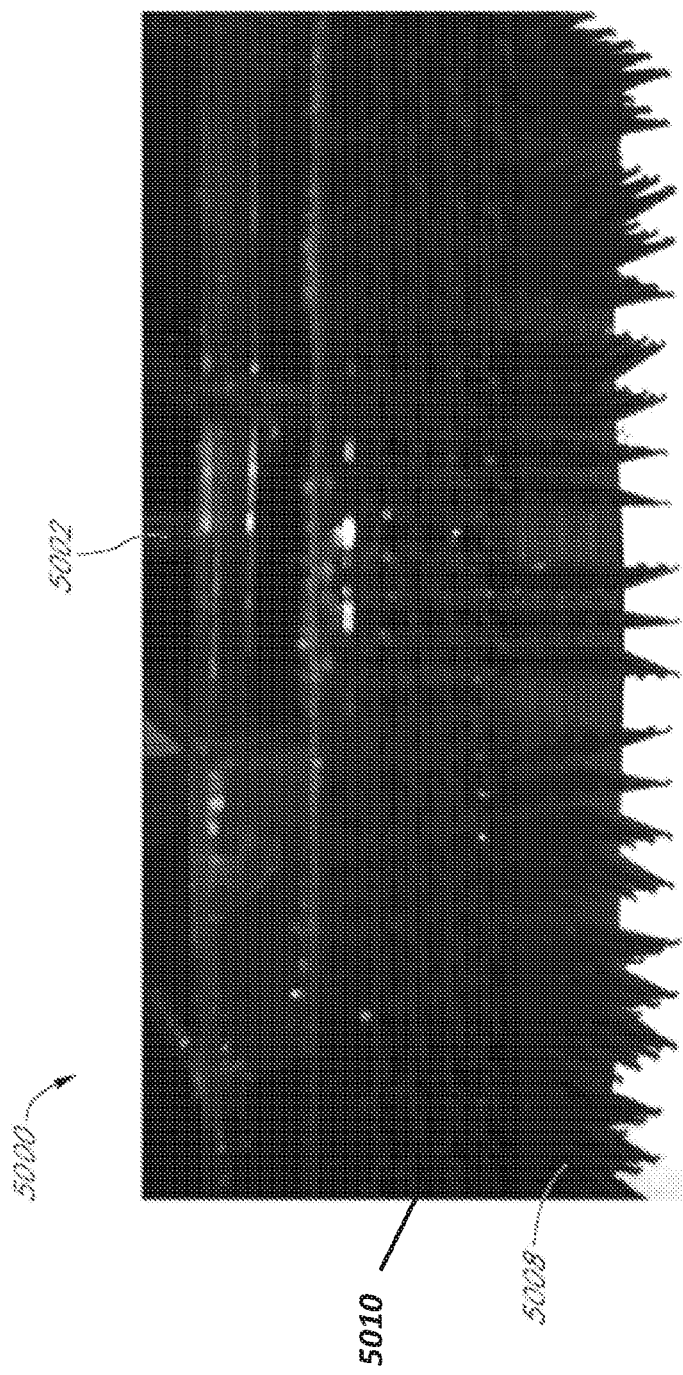
Figure 5D:
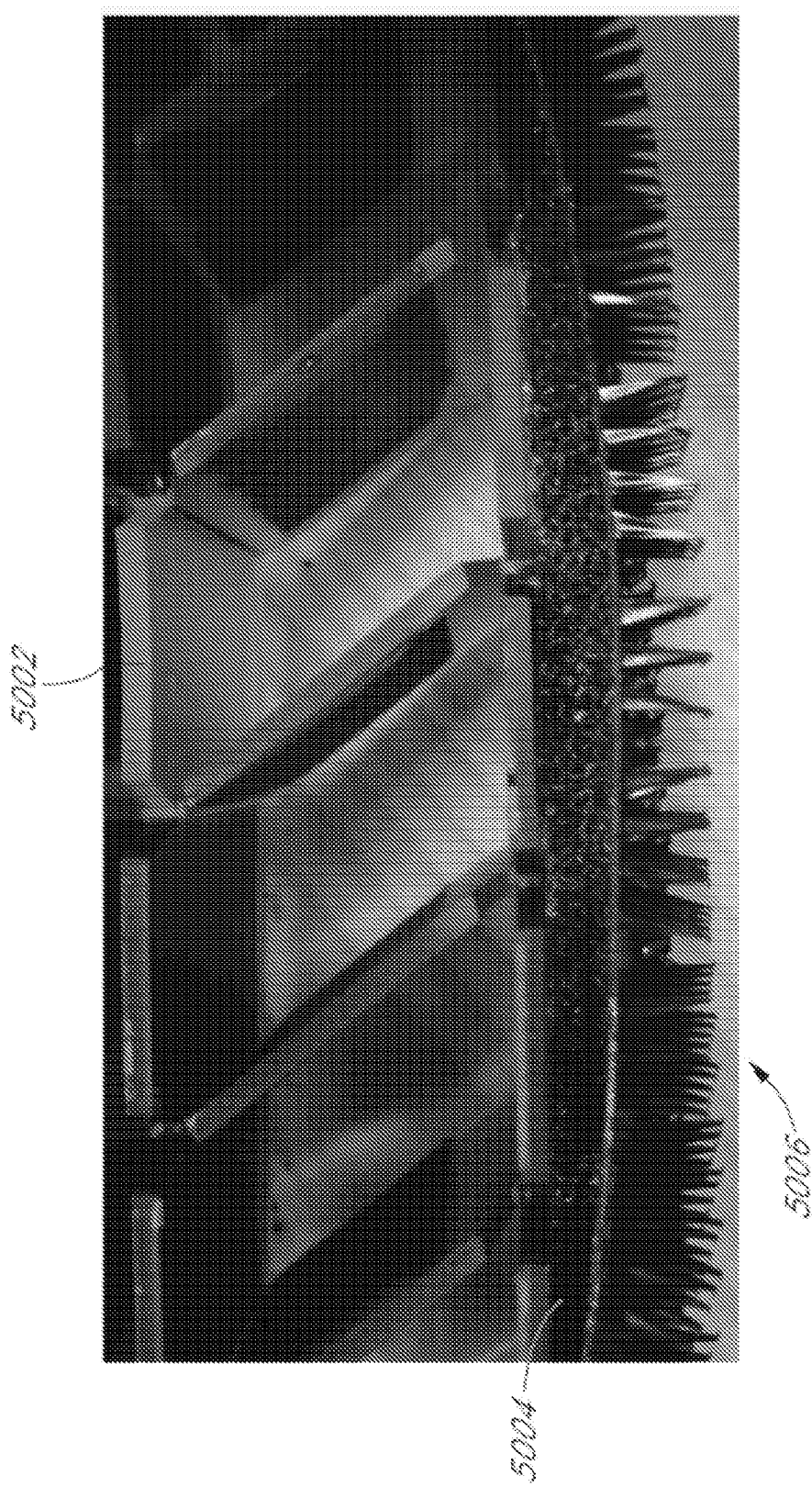

FIG. 5C is a photograph of an embodiment of a wound closure device 5000, similar to the wound closure devices of FIGS. 5A-B. However, in this orientation the first band 5008 of anchors is towards the bottom of the device, while the second band of anchors 5010 is towards the top. As described above, the bands of anchors may be arrayed in any desired manner. FIG. 5D is a top view of an embodiment of a wound closure device 5000, similar to the wound closure devices of FIGS. 5A-C.

Considering the anchoring layer of FIGS. 5A-D, the shape of the anchoring layer is not limited to the ring shape of FIG. 4. In some embodiments, the anchoring layer is wrapped around the entirety of the stabilizing device, i.e. the top, bottom, and sides. In other embodiments, the anchoring layer is only around a portion of the perimeter of the stabilizing structure. In certain embodiments, the anchoring layer is only attached to discrete portions of the stabilizing structure as needed. In some embodiments, the anchoring layer covers at most about 5%, at most about 10%, at most about 20%, at most about 30%, at most about 50%, at most about 75%, and at most about 100% of the outside of the stabilizing structure.

In some embodiments, the bands of different tissue anchors can be organized in a vertical direction, while in other embodiments, they may be organized in a horizontal direction. They may also be organized in either the horizontal and vertical directions when considered in the xy plane, i.e. facing downward into the wound.

In certain embodiments, the different types of anchors may be interspersed with one another, rather than organized into discrete bands of specific types of anchors. For example, the longer anchors may be surrounded by smaller anchors and vice-versa. In some embodiments, the anchors may be organized randomly across the anchoring layer or in other suitable patterns.

In particular embodiments, the anchoring layer may be disposed on the inner faces of the stabilizing structure. For example, the anchoring layer may cover at most about 5%, at most about 10%, at most about 20%, at most about 30%, at most about 50%, at most about 75%, and at most about 100% of the interior surfaces of the stabilizing structure.

In further embodiments, the entire anchoring layer may be comprised of only one type of anchor, for example the entirety of the anchoring layer may be comprised of the longer hooks 5008 or the shorter hooks 5010 as depicted in FIG. 5B. Some embodiments may call for the anchors to be color coded. For example, the anchors on the bottom may be made to be one color while the anchors on the top may be another so as to identify the proper orientation of the stabilizing structure in the wound.

Figure 6A:
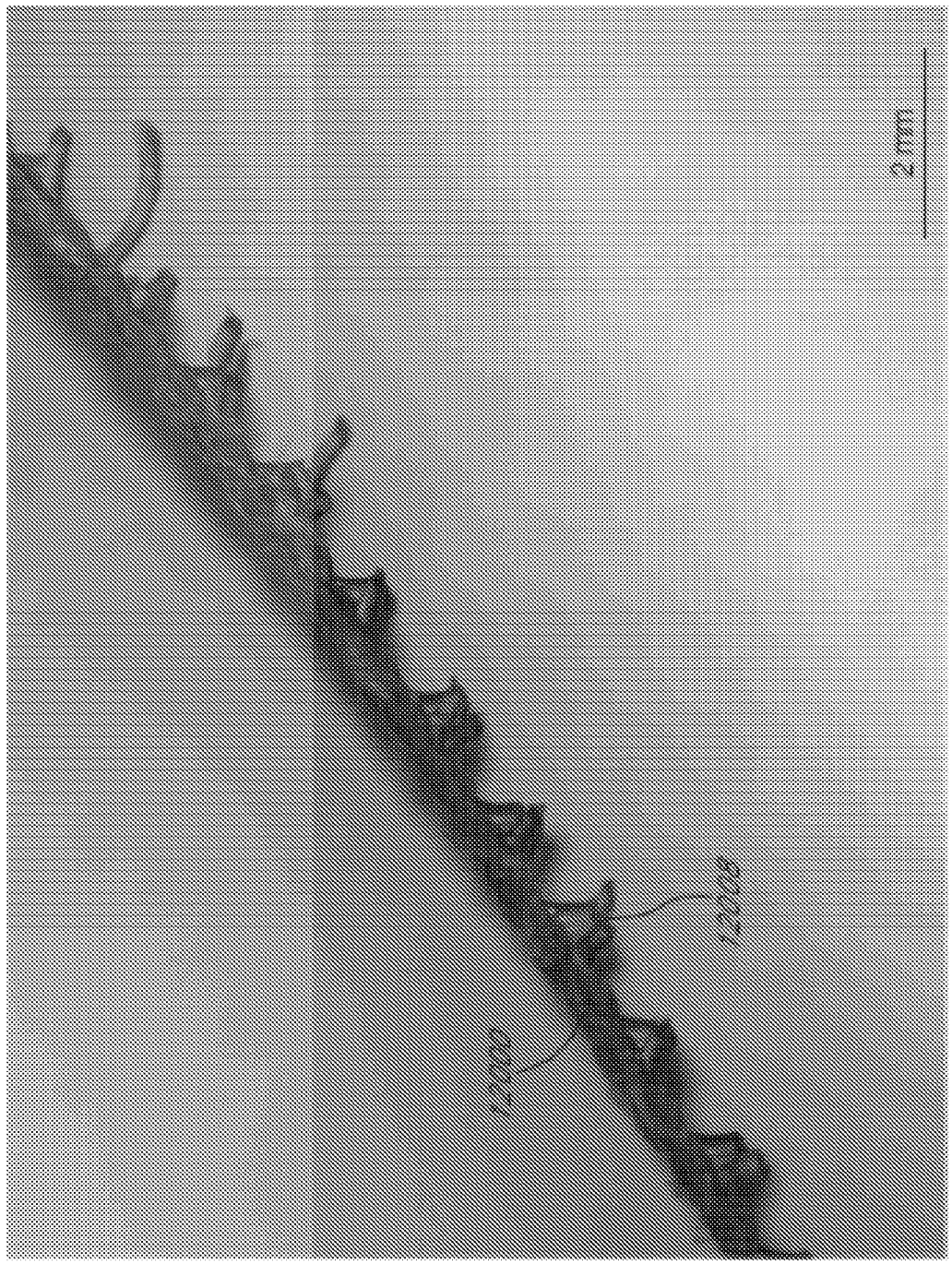
FIGS. 6A-B are photographs of an embodiment of an anchoring layer.
Figure 6B:
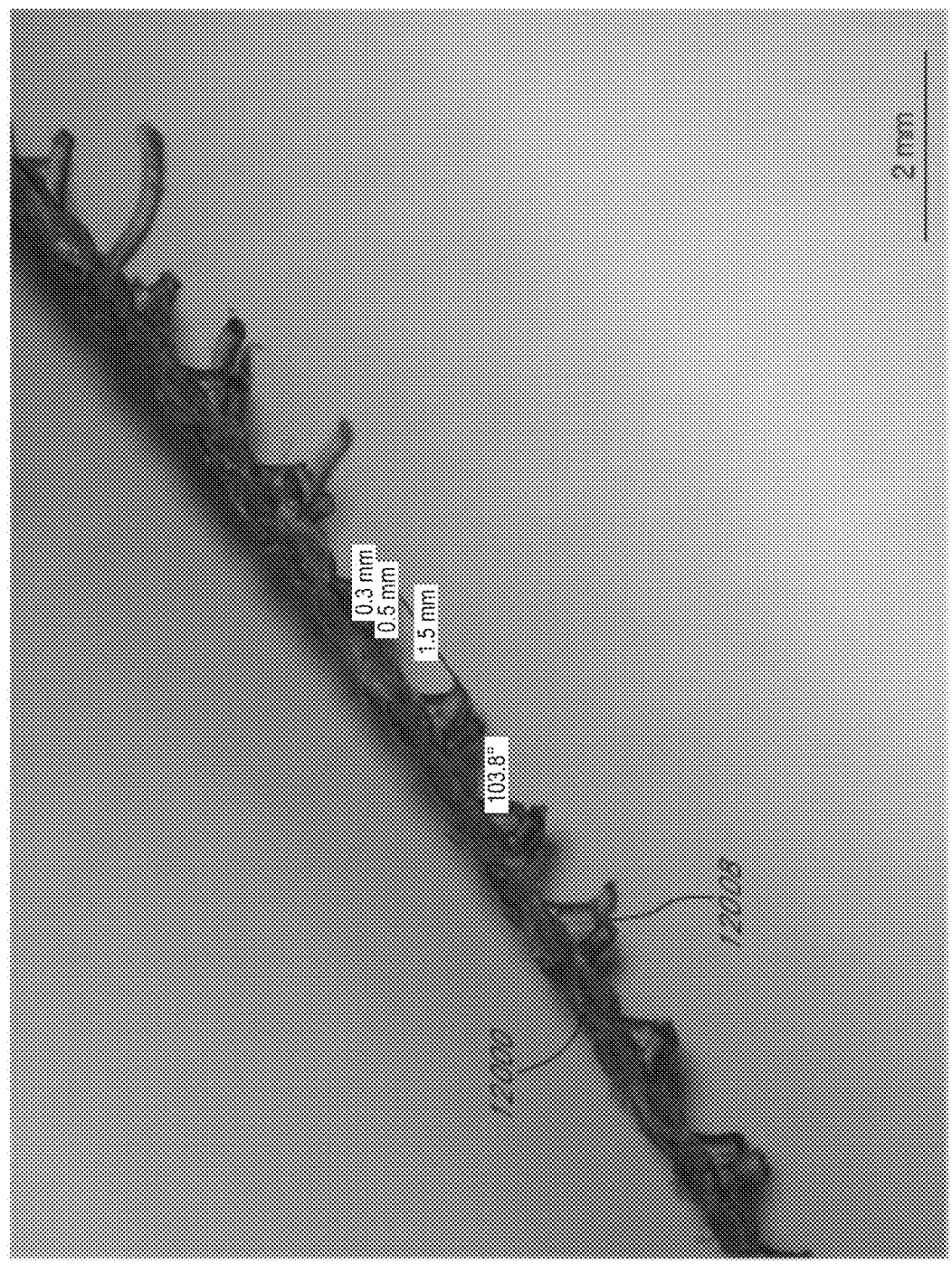

FIGS. 6A-B are pictures of embodiments of an anchoring layer 12000 with anchors 12008, similar to the anchors depicted in FIGS. 5A-D. Examples of such anchors may be available from Alfatex. In one embodiment, an anchoring layer may be provided comprising a 3D fabric material or portion thereof. For example, a 3D fabric may comprise a woven fabric layer provided along a first plane and a plurality of monofilaments extending perpendicularly from or at an angle relative to the woven fabric layer. The woven fabric layer may be configured to be attached to directly or indirectly to the outside of a stabilizing structure as described elsewhere in this specification and in the applications incorporated by reference. Monofilaments may have a mushroom-shaped head or other shapes configured to engage tissue surrounding the stabilizing structure. The head of the monofilaments may be similar to a peened rivet with a flatted head and extended edges that engage the surrounding tissues. If the monofilaments protrude at an angle then the material creates more grip in one direction of shear than another. This directionality means the anchoring layer and monofilaments can be positioned on a stabilizing structure so that the shear acts to stop the device being forced up or out of the wound by the viscera but can be easily released by pushing it down.

Wound Closure and Treatment Methods of FIGS. 7-15E

The stabilizing structures and/or wound closure devices described in this section or elsewhere in this specification may be used in conjunction with methods or systems for the closure of a wound. In some embodiments of methods of use for closure of a wound, one or more of the stabilizing structures or wound closure devices of any of the embodiments described in this section or elsewhere in this specification is placed into a wound. In some embodiments, an organ protection layer may be provided in the wound before placement of the stabilizing structure. In certain embodiments, foam or other porous material may be placed in the wound along with the stabilizing structure or wound closure device, either below, above, or surrounding the stabilizing structure or wound closure device. Foam or other porous material may also surround the perimeter of the stabilizing structure or wound closure device. The stabilizing structure or wound closure device may be configured to collapse in any manner as described in this section or elsewhere in this specification, for example by having a particular size and shape, or by comprising a certain volume of foam or other porous material within the cells of the structure. The stabilizing structure or wound closure device may further be altered in any manner described in this section or elsewhere in this specification so as to better accommodate the shape of the wound. After placement in the wound, the stabilizing structure or wound closure device can be sealed by a fluid-tight drape. The fluid-tight drape can comprise a port configured for the application of negative pressure. A source of negative pressure may then be connected to the port and negative pressure may be applied to the wound. The stabilizing structure or wound closure device may be replaced over time by stabilizing structures or wound closure devices of various shapes and sizes as desired to best promote wound healing.

FIGS. 7-15E are photographs and illustrations depicting embodiments of methods for the treatment of a wound that utilize a wound closure device comprising a stabilizing structure as described herein this section and elsewhere in the specification. To better illustrate non-limiting embodiments of the methods, numbers have been added to the steps of FIG. 13 to allow the reader to more easily follow these steps of the method. However, the steps can be performed in any order, and any numbering system is for clarity only. Further, in some embodiments, different steps of these methods may be excluded. In other embodiments, additional steps may be added to the methods based on methods described herein this section and elsewhere in the specification. The porous layers and structures described in this section may be of any material or structure described elsewhere in the specification, such as foam.

Figure 7:
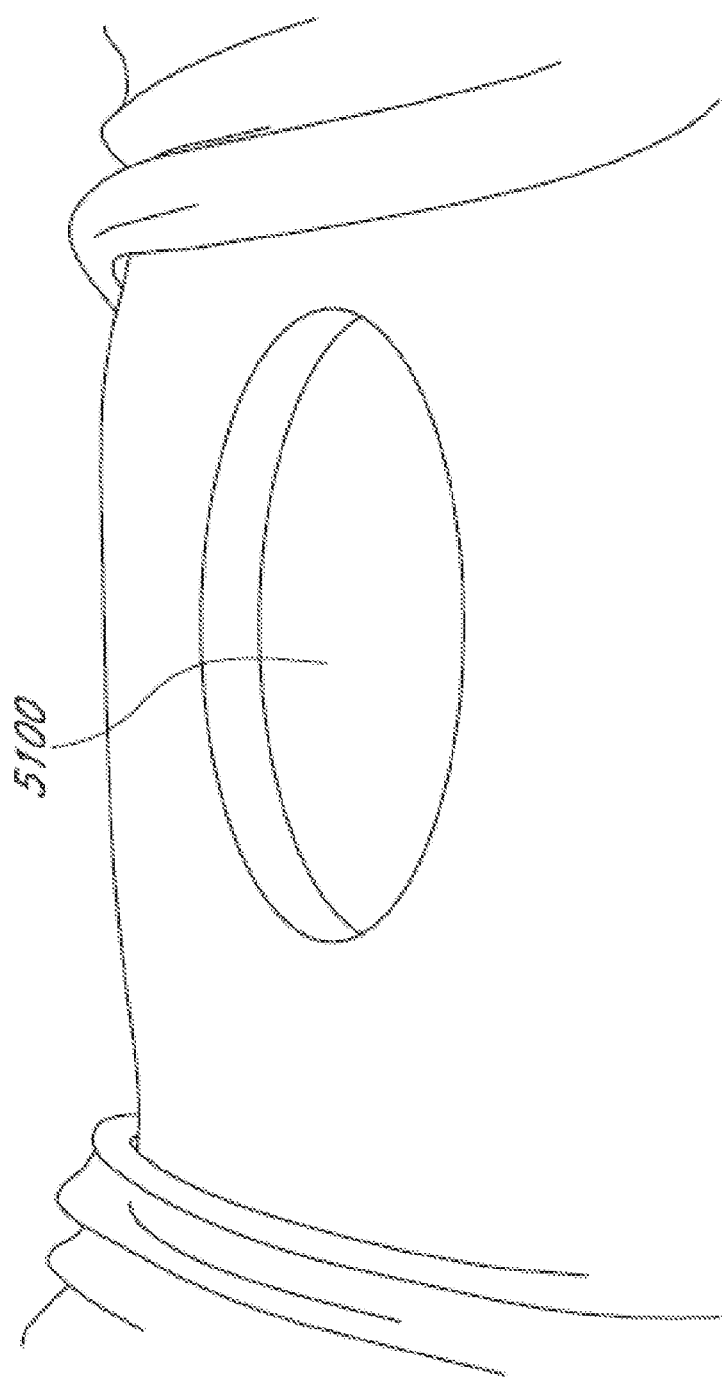
FIG. 7 illustrates an embodiment of an open abdominal wound.

FIG. 7 depicts an embodiment of an open wound 5100 prior to treatment with a wound closure device as will be described in much greater detail below. The open wound of FIG. 7 is similar to the wounds described elsewhere in the specification, particularly as relate to FIG. 1. In some instances, as described elsewhere in the specification, such a wound may be produced via a surgical incision or other means.

Figure 8:
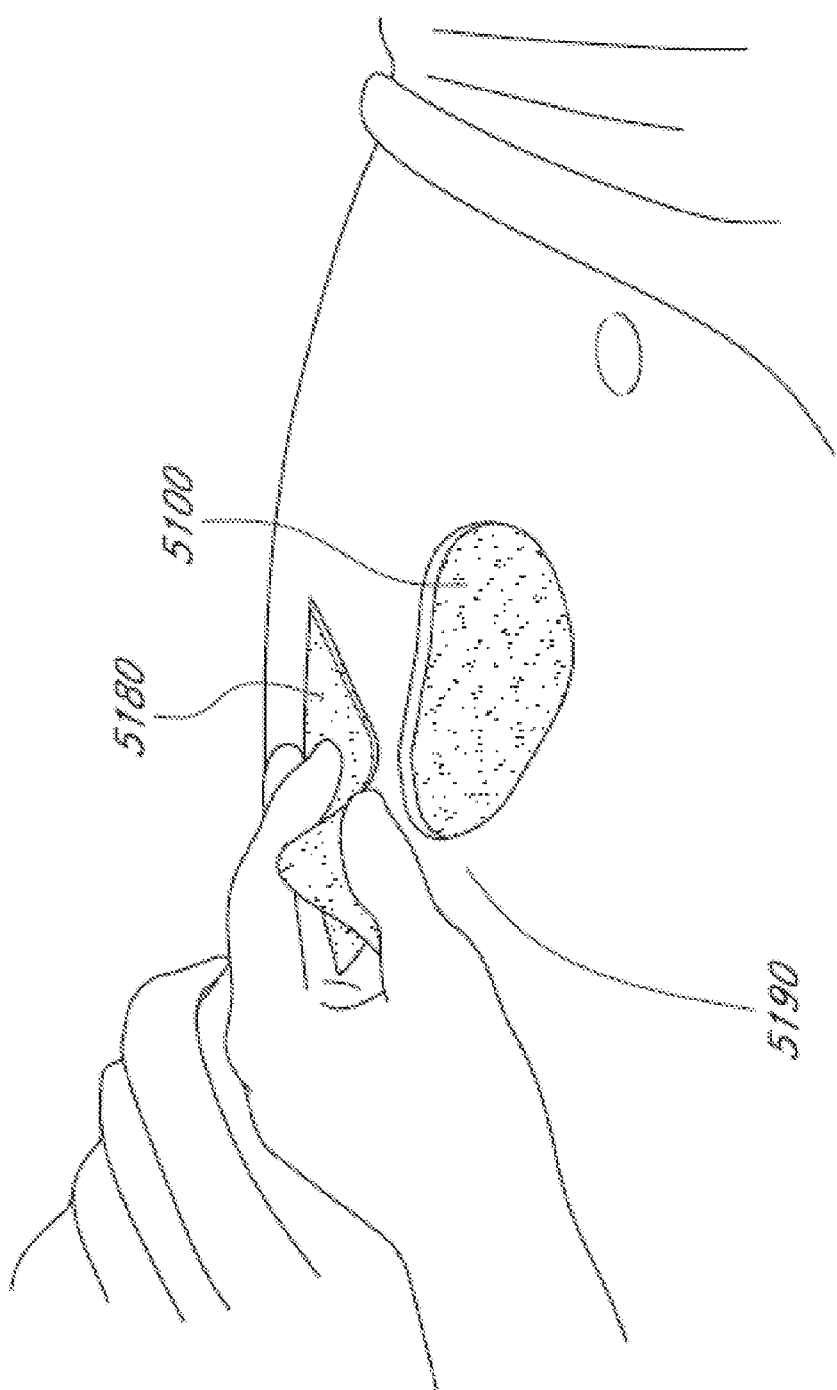
FIG. 8 illustrates an embodiment of a step in a method of treating a wound.

FIG. 8 depicts an embodiment of an initial step in a method for the treatment of an open wound 5100 with a wound closure device. Before treatment, the wound may be cleaned with a pad 5180 and the skin 5190 prepared for application of a wound closure device, such as those described in relation to FIGS. 2A-3E.

Figure 9:
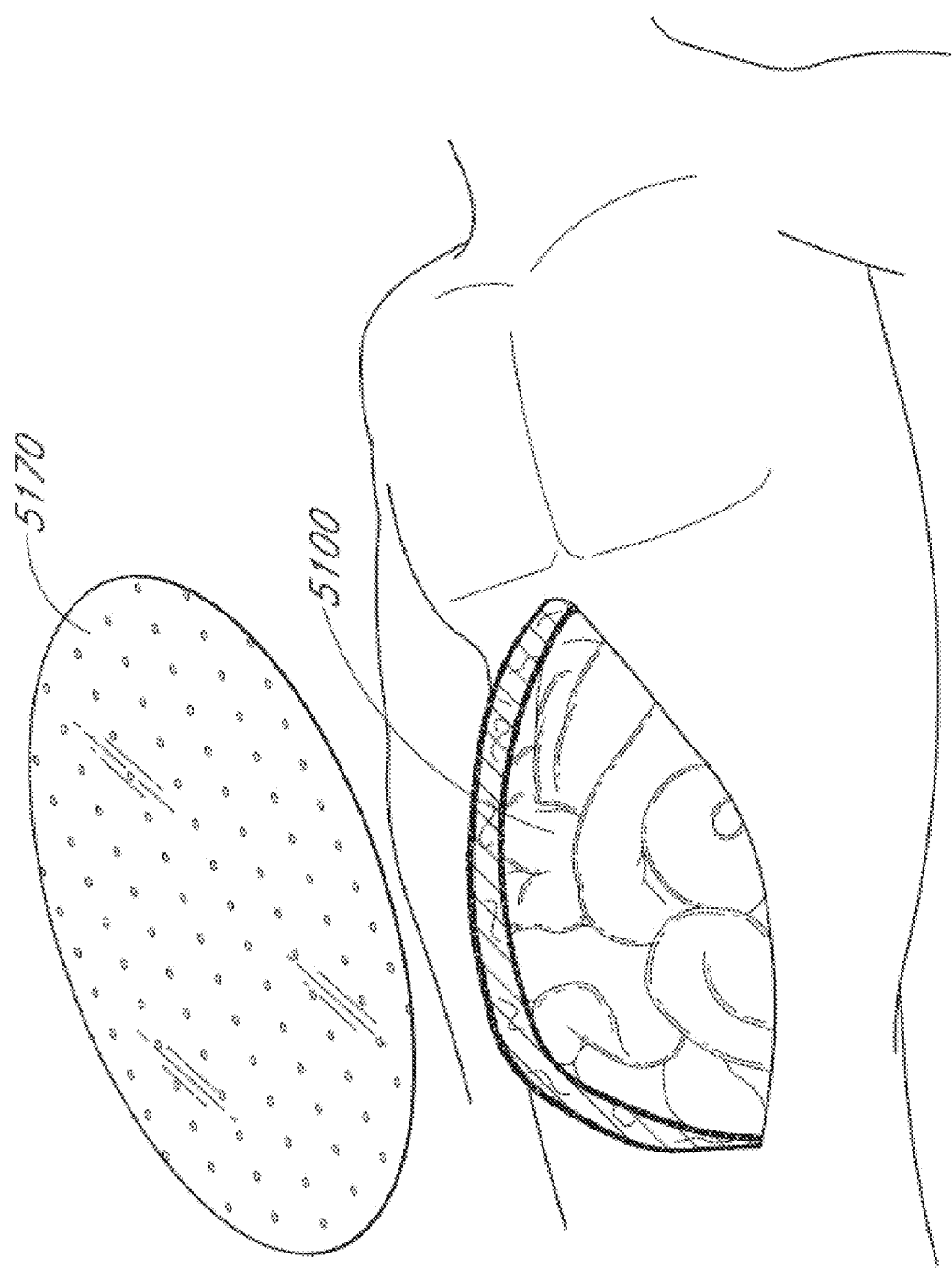
FIG. 9 illustrates an embodiment of a step in a method of treating a wound.

FIG. 9 depicts an embodiment of an early step in a method for the treatment of an open wound 5100. In some embodiments, a tissue protection layer 5170 may be placed over the wound to protect the underlying tissues from the rigors of negative pressure wound therapy or other potential harms. Accordingly, certain embodiments provide for a tissue protection layer 5170 which may be cut to size to be placed over the wound site 5100. The tissue protection layer 5170 can be a material which will not adhere to the wound site or to the exposed viscera in close proximity. Such a tissue protection layer may be constructed from any suitable material such as a biocompatible polymer. For example, organ protection layers manufactured by Smith & Nephew and sold under the brand RENASYS® may act as tissue protection layers and be placed over the abdominal cavity and/or wound bed 5100 and tucked over the peritoneal gutter. In further examples, materials such as the fluoropolymer polytetrafluoroethylene (PTFE) may be applicable as these materials are generally non-adherent and used in surgical grafts. In one embodiment, the tissue protection layer is permeable. For example, the tissue protection layer 5170 can be provided with openings, such as holes, slits, or channels, to allow the removal of fluids from the wound site 5100 or the transmittal of negative pressure to the wound site 5100. In further embodiments, the tissue protection layer may be used over non-abdominal wounds on other areas of the body, such as the leg, arm, shoulder, or back. In certain embodiments, the tissue protection layer may comprise a sensor configured to measure pressures in and around the wound. For example, the sensor may be used to measure the level of negative pressure applied to the wound or to measure the pressure on the underlying organs beneath the abdominal wound.

Figure 10B:
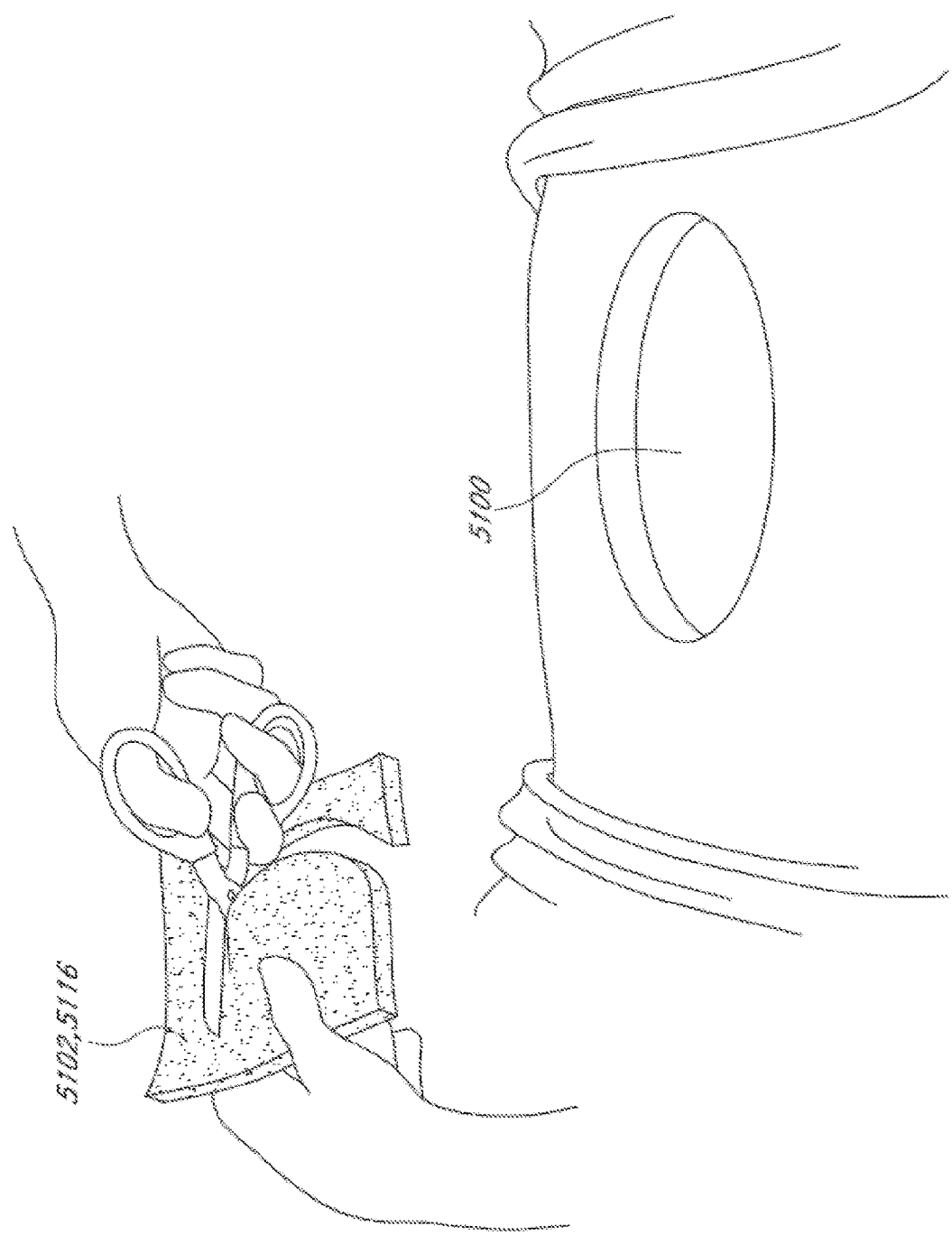
Figure 10C:
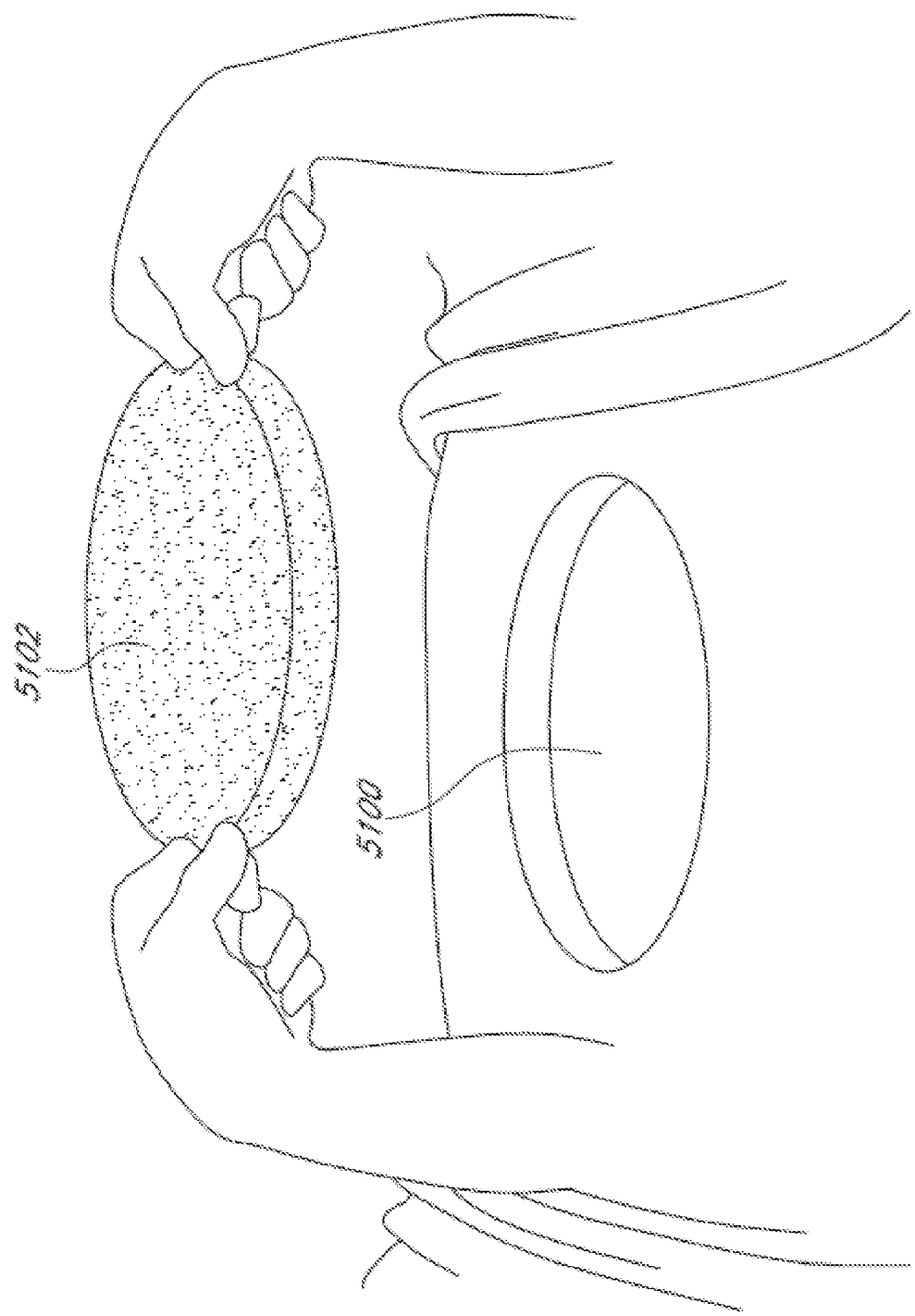

FIGS. 10A-C illustrate embodiments of possible initial steps in a method for the treatment of an open wound. However, as described above, the steps need not be performed in this order and may be performed in any order. In FIG. 10A, two pieces of a porous material such as foam, a bottom piece 5102 and a top piece 5116 are selected so as to approximate the size of the wound 5100. In some embodiments, the top piece and the bottom piece are of identical thickness. However, in certain embodiments, and vice-versa, top piece 5116 may be at least twice as thick, at least four times as thick, at least 10 times as thick or more than ten times as thick as bottom piece 5102. FIG. 10B illustrates an embodiment of additional steps in a method for the treatment of an open wound. Bottom piece 5102 may be shaped via cutting or other suitable means to the shape of the wound and subsequently placed into the wound 5100, as shown in FIG. 10C and depicted further below in FIG. 11A.

Figure 11A:
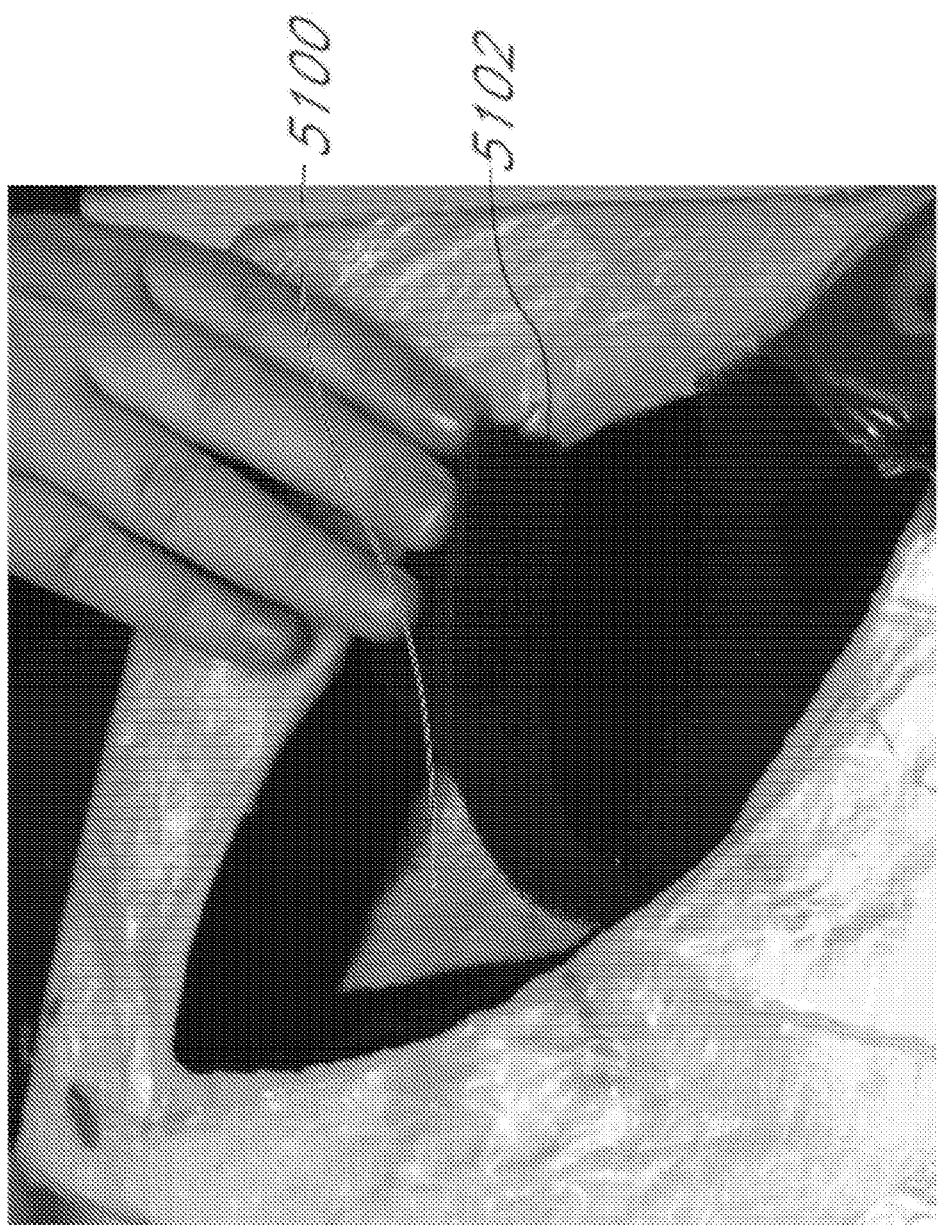
FIGS. 11A-B are photographs of steps of a method of treating a wound.
Figure 11B:
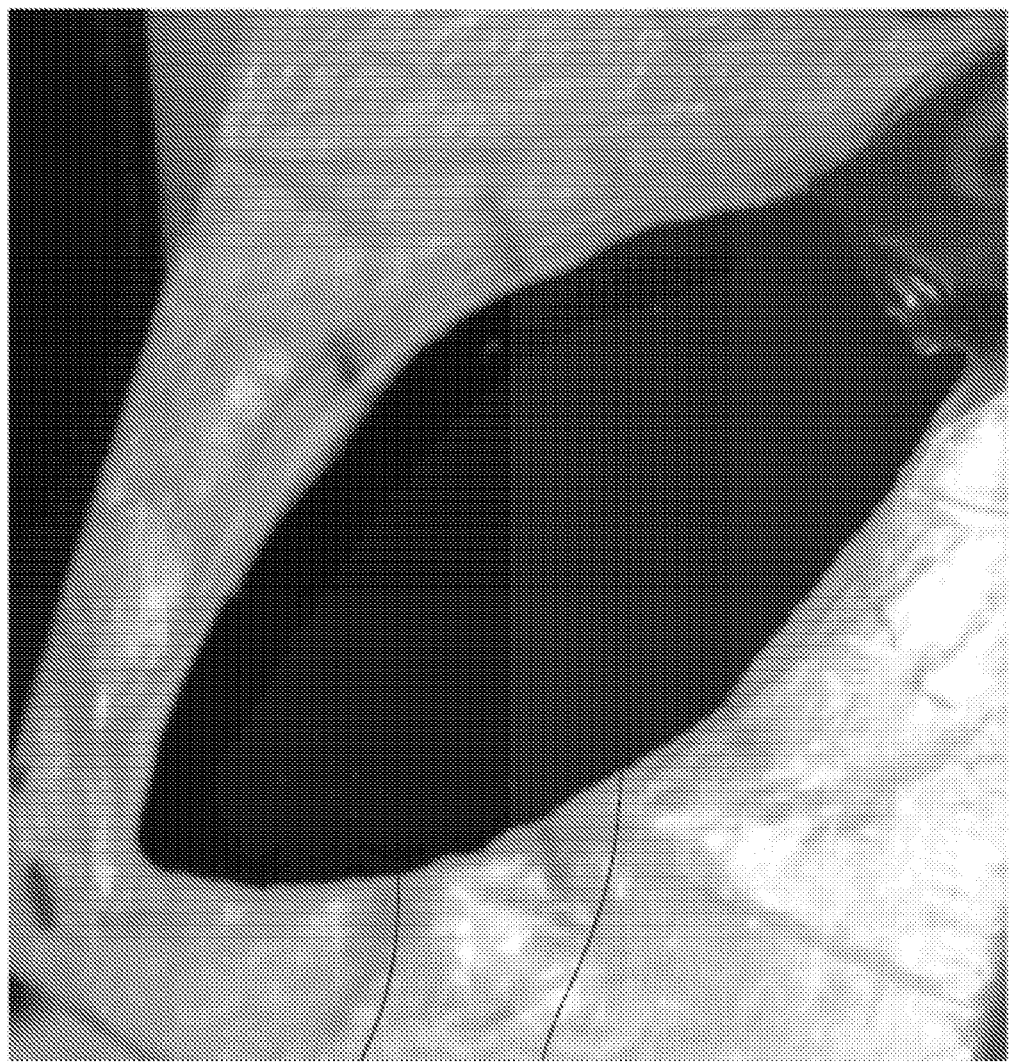
Figure 12A:
FIGS. 12A-C depict an embodiment of steps of a method of treating a wound.
Figure 12B:
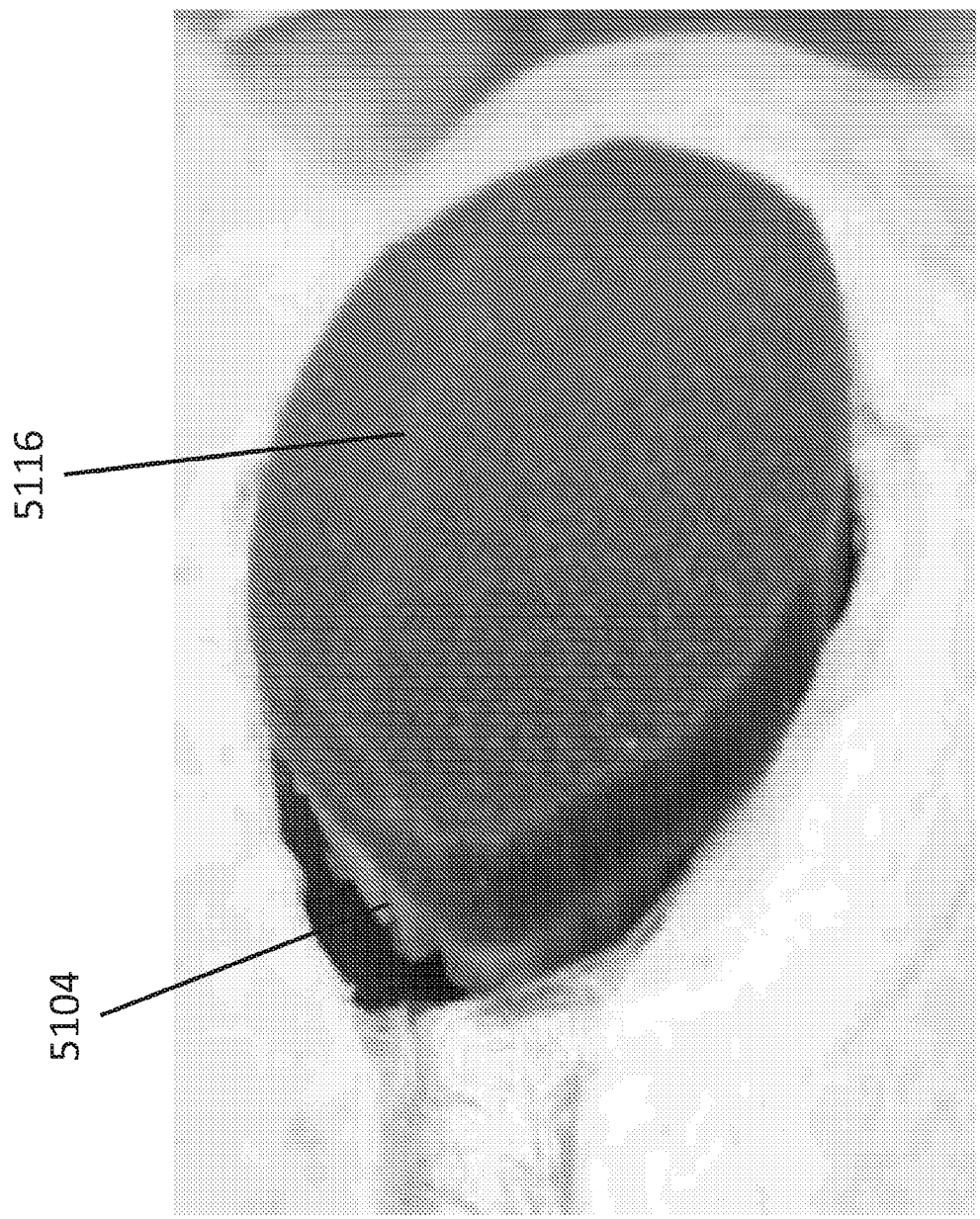
Figure 12C:
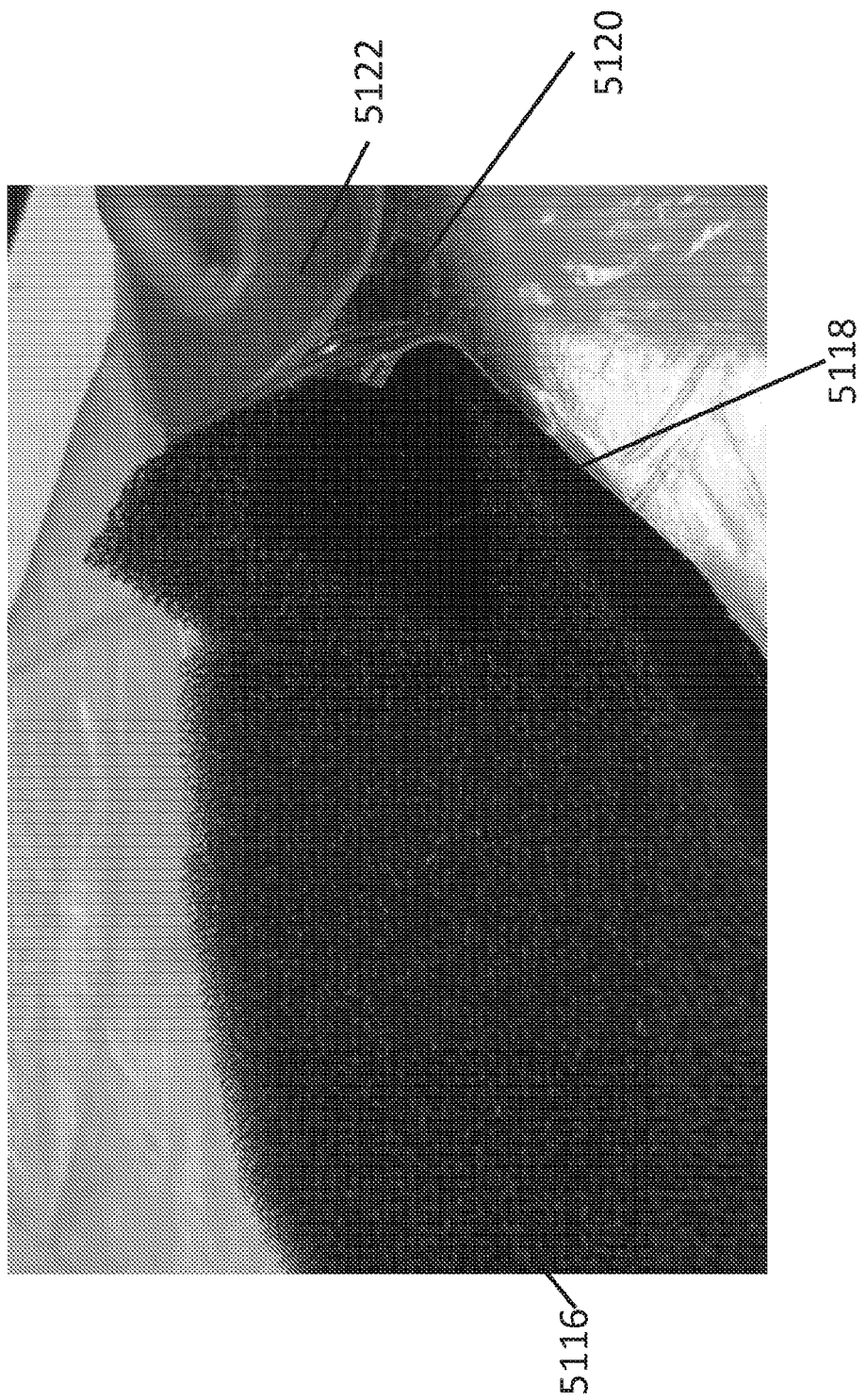

FIGS. 11A-B are photographs of a foam layer 5102 (for example, a 15 mm layer of foam), after shaping, placed into a wound bed 5100. In FIGS. 12A-C, a stabilizing structure 5104 similar to the stabilizing structures disclosed in FIGS. 2A-3E or any other stabilizing structure described elsewhere in the specification, is in the shape of the wound. The stabilizing structure may be shaped into the shape of the wound via cutting or other suitable means or the stabilizing structure may initially be of a size that is readily accommodated by the wound. As displayed in FIG. 12B, the stabilizing structure 5104 may be placed into the wound. To assist with the insertion of the device into the wound bed, the device can be deformed slightly inwardly or horizontally to facilitate entrance into the wound site. In some embodiments, the device may be squeezed slightly during insertion and then release upon contact with the walls of the wound. In certain embodiments, the wound closure device 5104 may be placed such that the longitudinal sides of the matrix align with the longitudinal axis of the wound 5100. Continuing with FIG. 12B, another foam layer 5116 (for example, a 10 mm layer of foam) is placed on top of the wound closure device 5104.

FIG. 12C is a photograph of application of a port 5122 to the stabilizing structure and foam of FIGS. 12A-B. A bridging portion of foam 5118 may be placed in intimate contact with the foam layer 5116 at the edge of the wound. The bridging portion of foam 5118 may extend over intact skin, with a piece of drape 5120 placed between it and the intact skin. Further, a suction port 5122 may be connected to the bridging portion 5118 with a section of drape 5120 between. In alternative embodiments, the bridging portion 5118 and suction port 5122 may be placed on the wound during a different step depicted in FIGS. 11A-12B.

Figure 13:
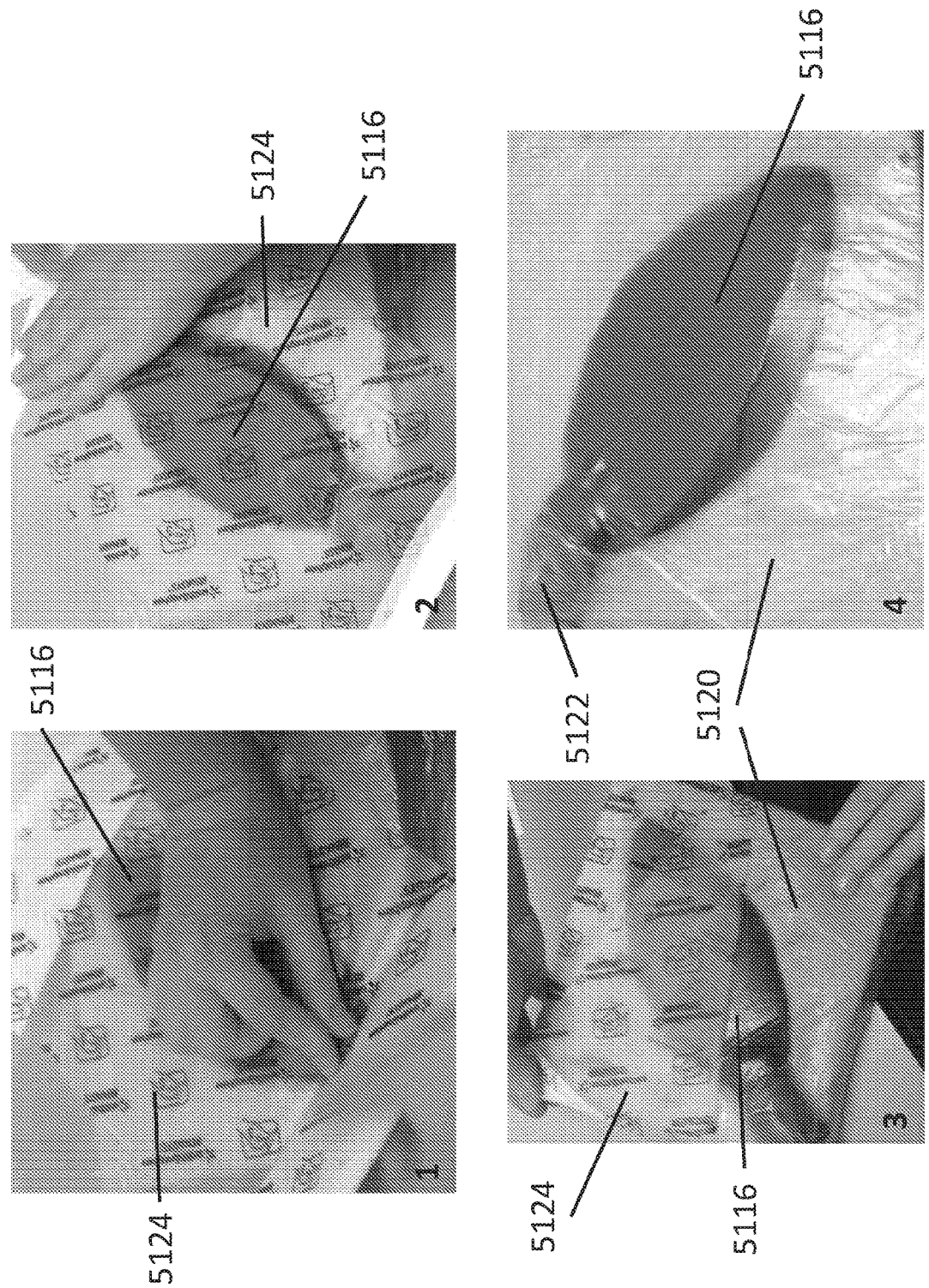
FIG. 13 contains photographs of embodiments of steps of a method of treating a wound.

In FIG. 13, as shown by steps 1-4, the device may be covered by one or more drapes 5120. A hole may be made in the drape covering the bridging portion of foam, and a suction port 5122 may be placed over the hole. A protective layer 5124 on the top surface of the one or more drapes may be removed after the drapes 5120 are applied. Once the drapes 5120 are applied and the port is in place, negative pressure may be applied to the wound through the drape from a vacuum source. The negative pressure can cause the stabilizing structure to collapse horizontally as described elsewhere in this specification. The tissue anchors adhered to the stabilizing structure through the porous layer engage tissue of the wound and may facilitate closure of the wound.

In certain embodiments, the suction port may be placed directly over the central portion of the foam layer 5116. In such embodiments, the foam layer may collapse inward along with the stabilizing structure while under negative pressure, thereby collapsing the suction port. To avoid collapse, the suction port may be rigid in comparison to the foam and resist collapse. A washer may be placed inside, below, or around the suction port to provide rigidity and resist collapse.

In some embodiments, the suction port may be pre-attached to the top foam layer so that drapes can be positioned around the port. A hard port or a soft port may be used, such ports may further be used in combination with a washer such as described above. In further embodiments, the suction port could only partially collapse with the collapsing matrix while still maintaining the port opening for negative pressure.

Figure 14A:
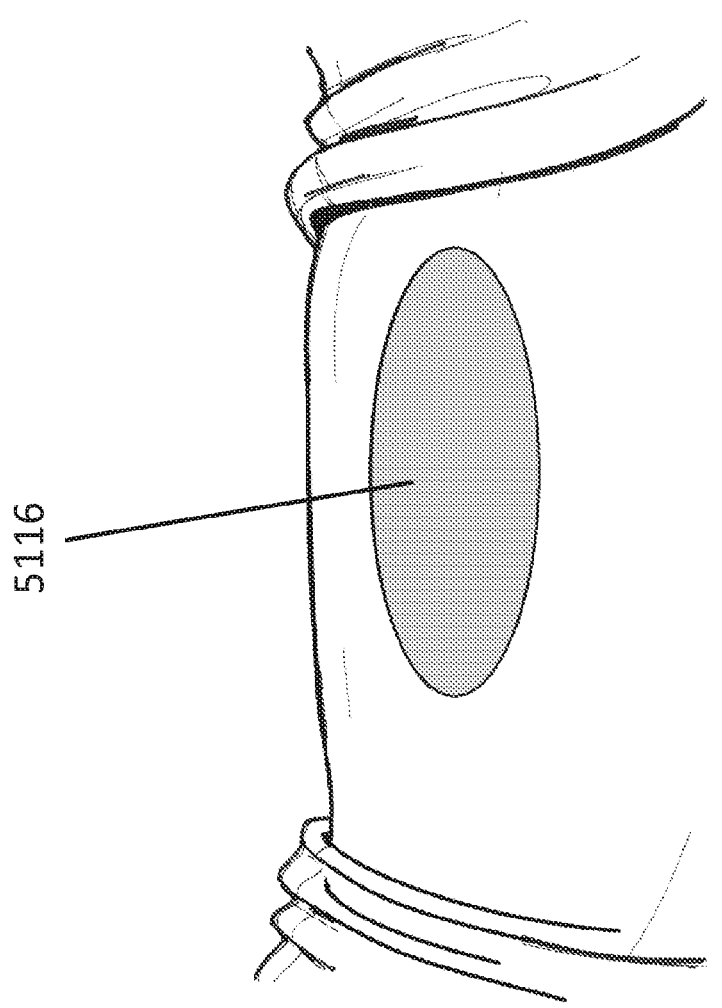
FIGS. 14A-G illustrate an embodiment of a method of treating a wound.
Figure 14B:
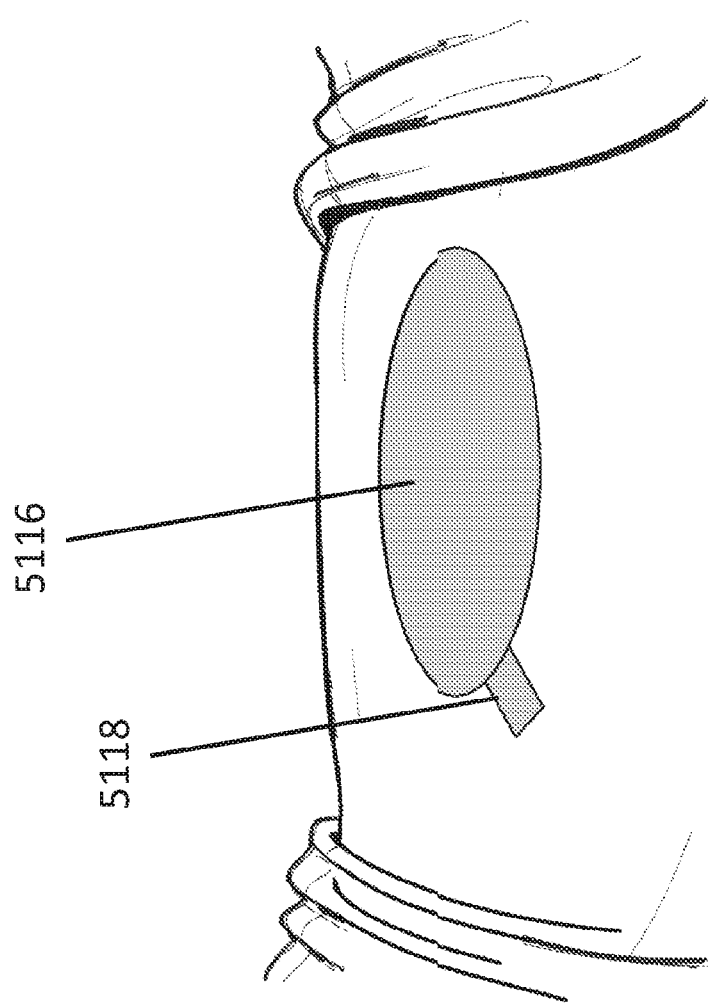
Figure 14C:
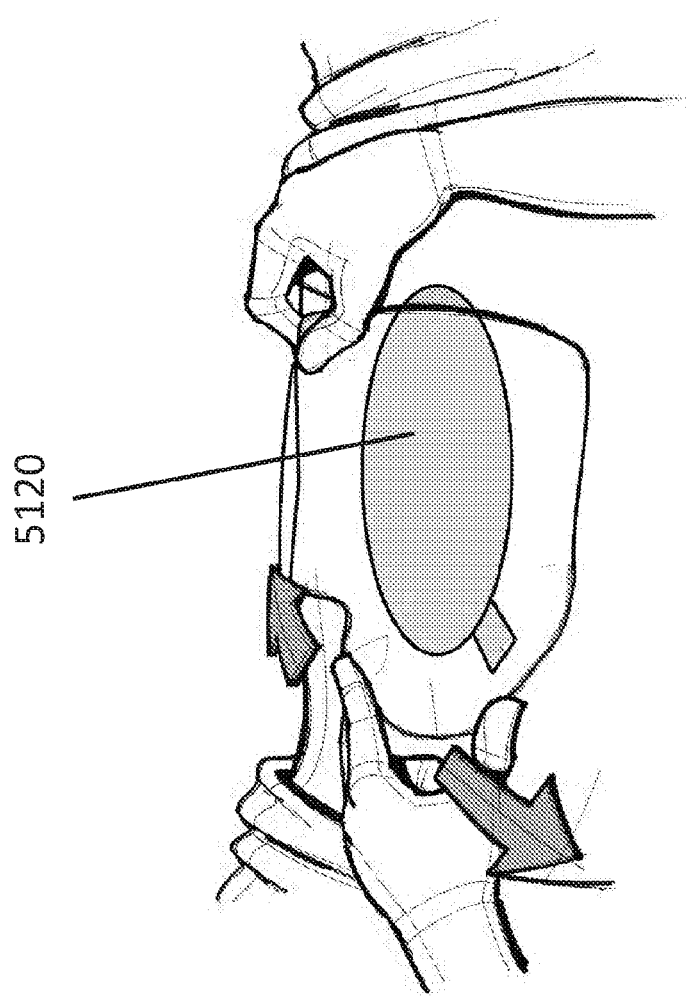
Figure 14D:
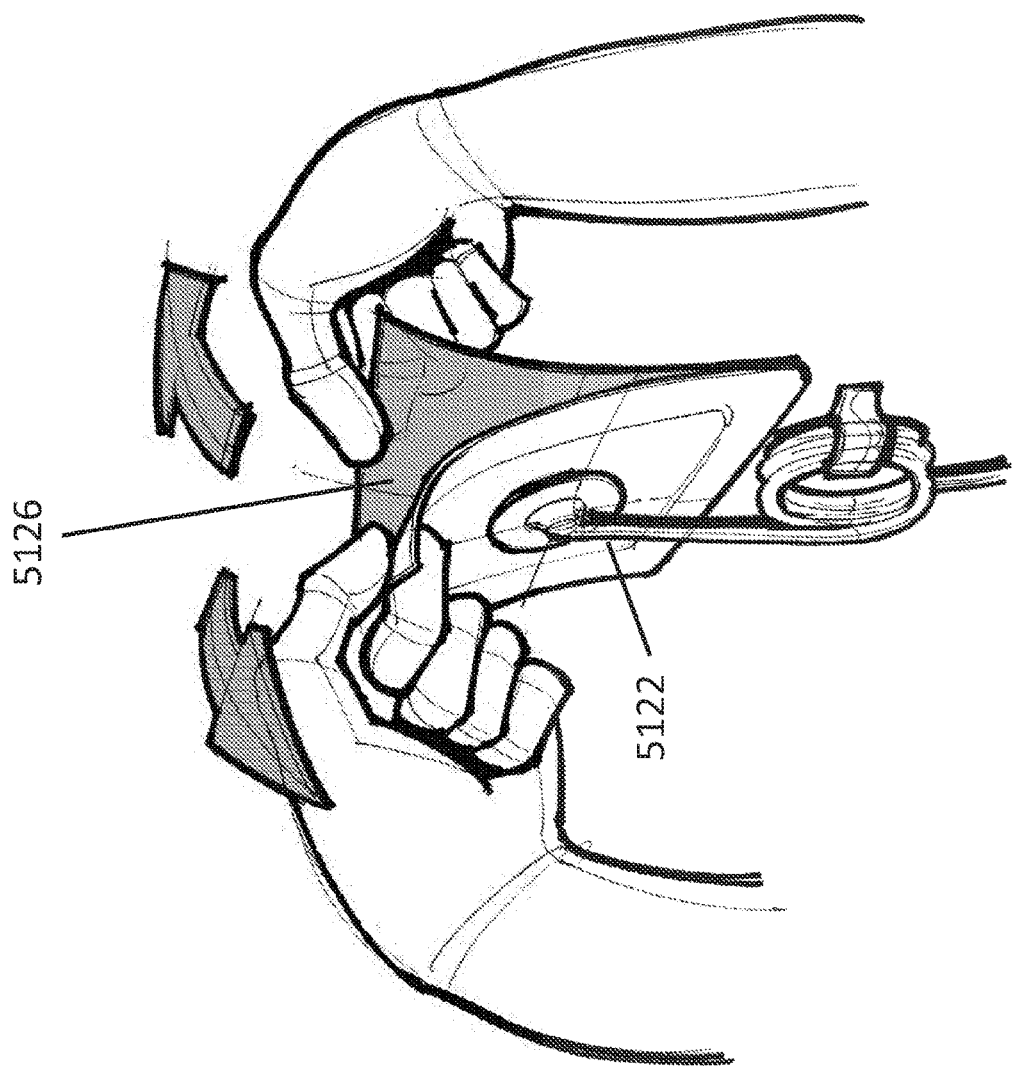
Figure 14E:
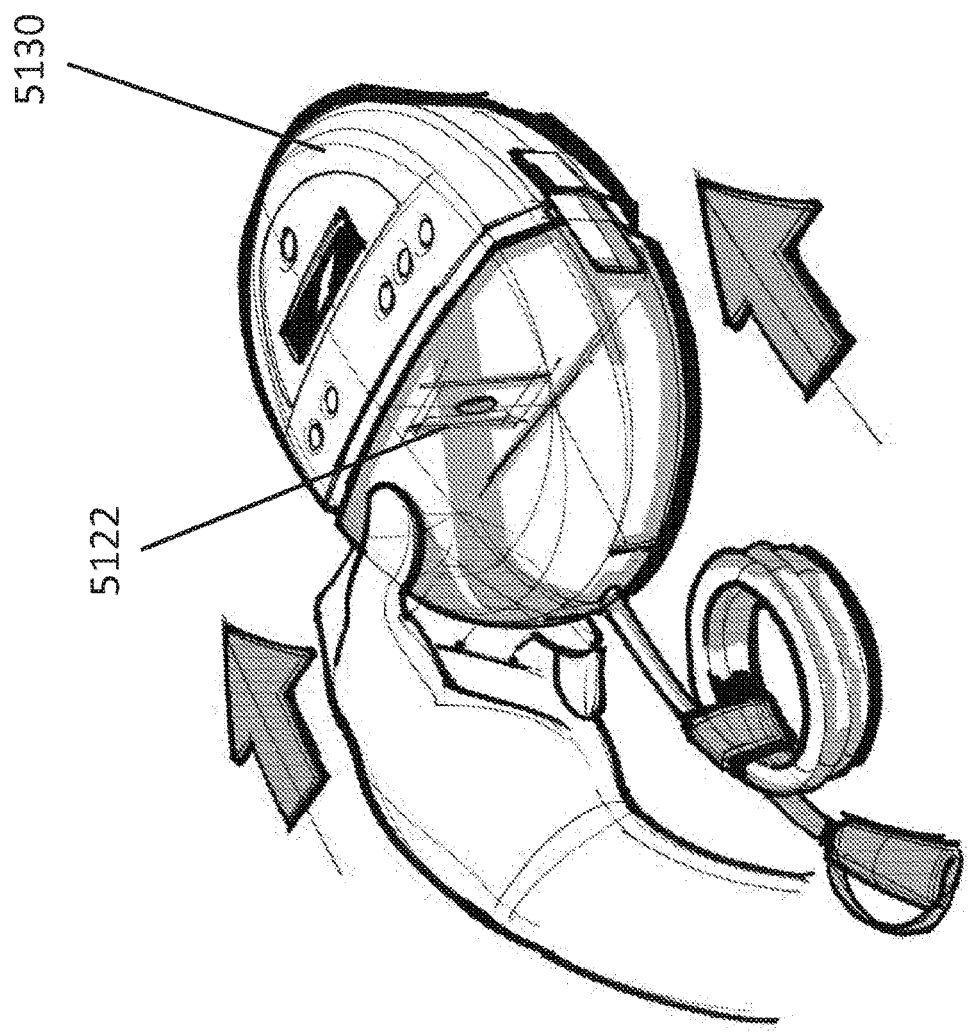
Figure 14F:
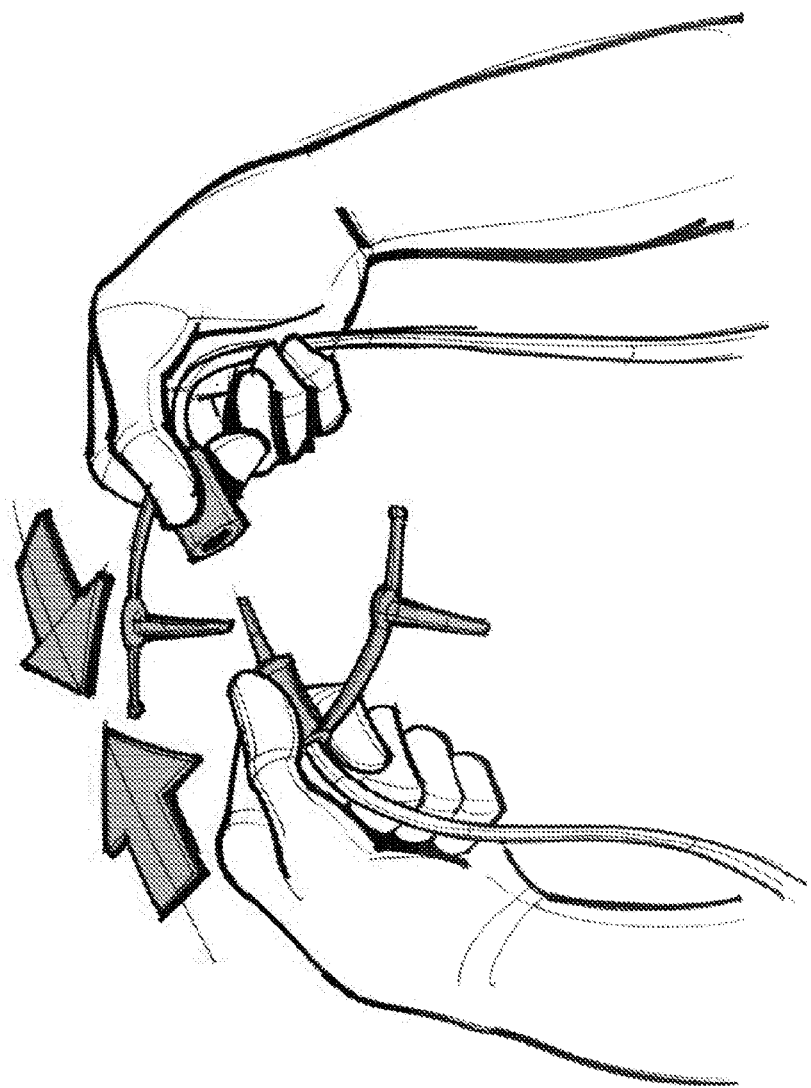
Figure 14G:
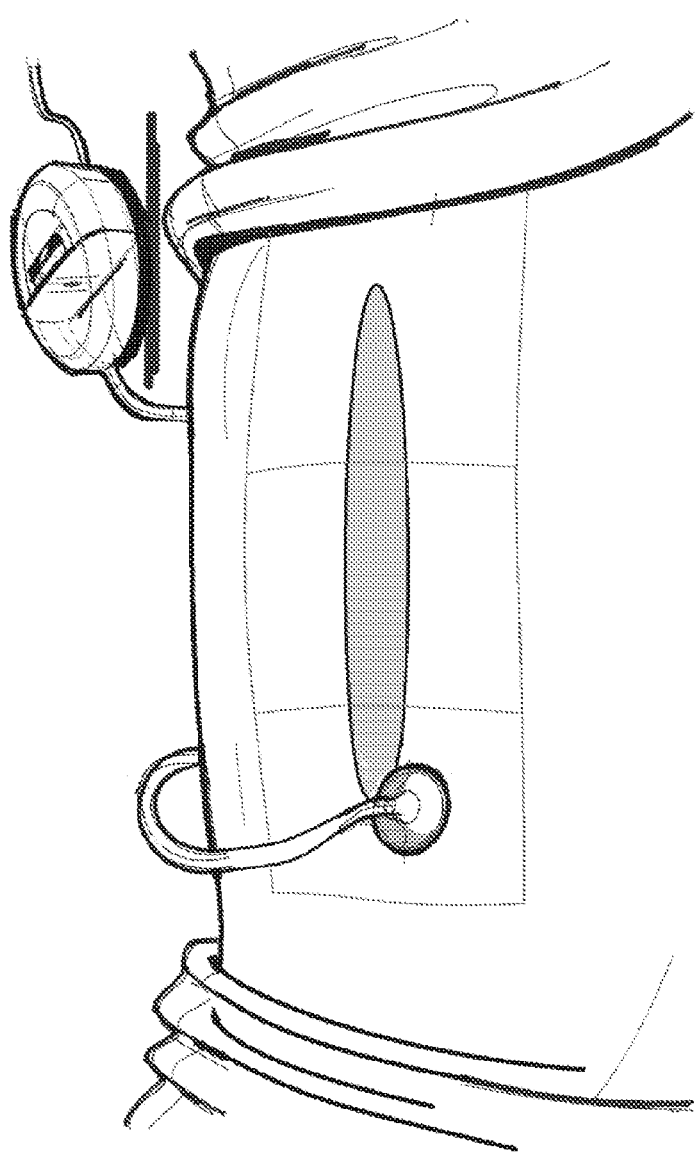

FIGS. 14A-14C provide further illustrations of an upper foam layer 5116 being placed in a wound, followed by placing a bridging portion 5118 and placing one or more drapes or wound covers 5120. FIGS. 14D-14G illustrate an embodiment of several steps in a method for the treatment and closure of a wound. As illustrated in FIG. 14D, a suction port 5122 is separated from a release liner 5126 and later applied to a wound as depicted in FIGS. 11A-13. FIG. 14E illustrates a canister being inserted into a negative pressure wound therapy device 5130 in preparation for the collection of wound exudate. FIG. 14F illustrates the snap connection between the tubing connected to the suction port and the tubing connected to the negative pressure wound therapy device 5130. Once the connection has been made, negative pressure wound treatment may begin as depicted in FIG. 14G.

Figure 15A:
FIG. 15A-E are photographs of an embodiment of a method of treating a wound.
Figure 15B:
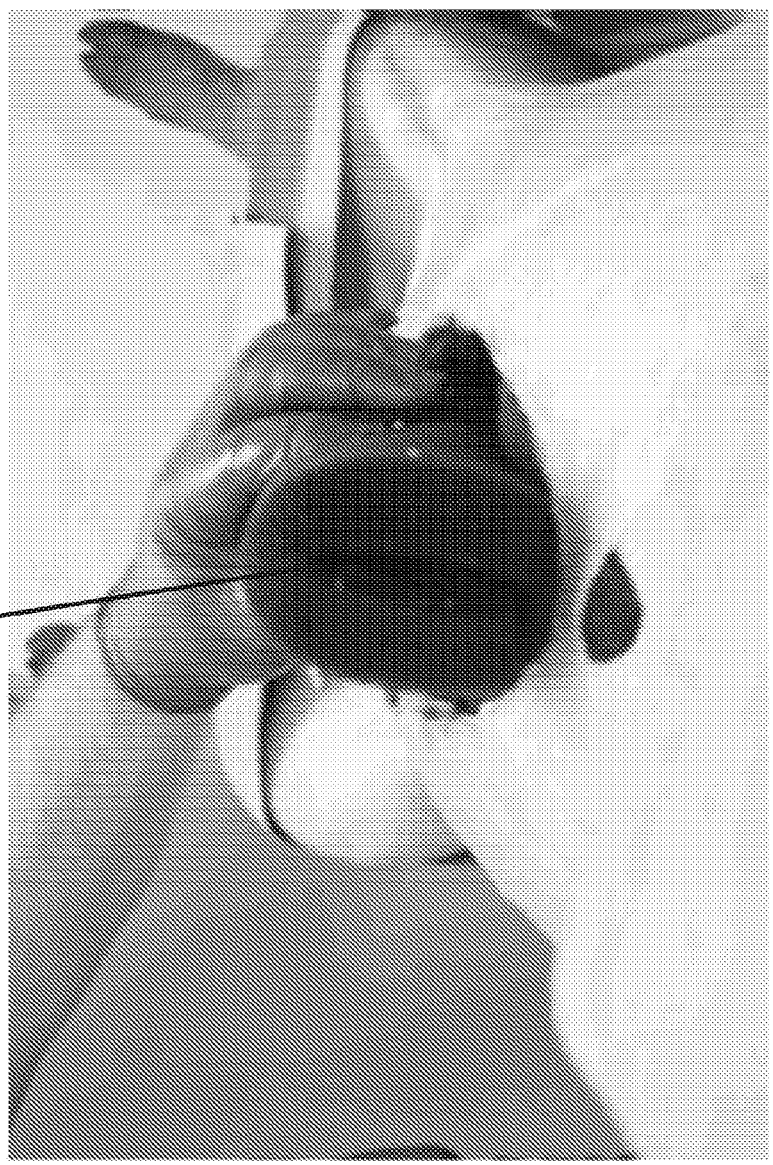
Figure 15C:
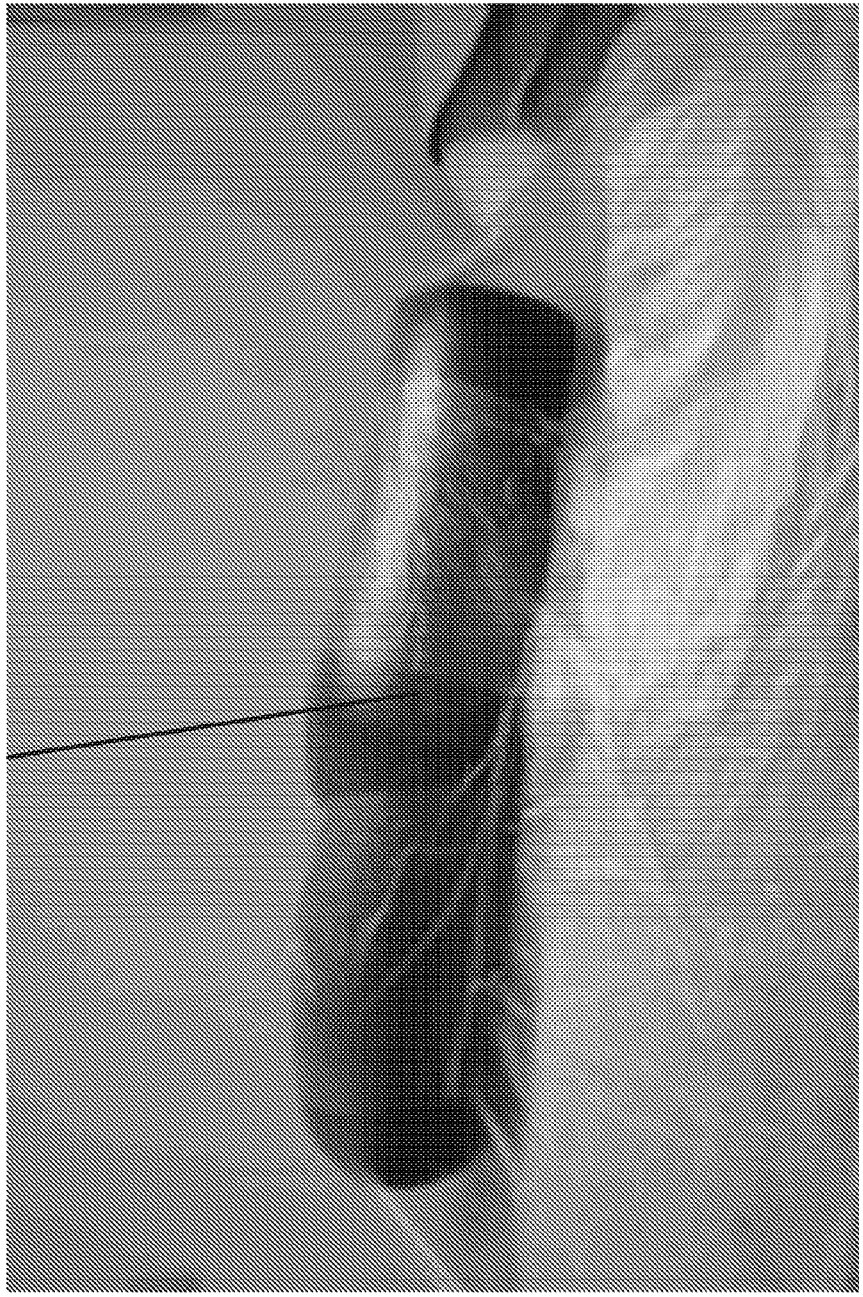
Figure 15D:
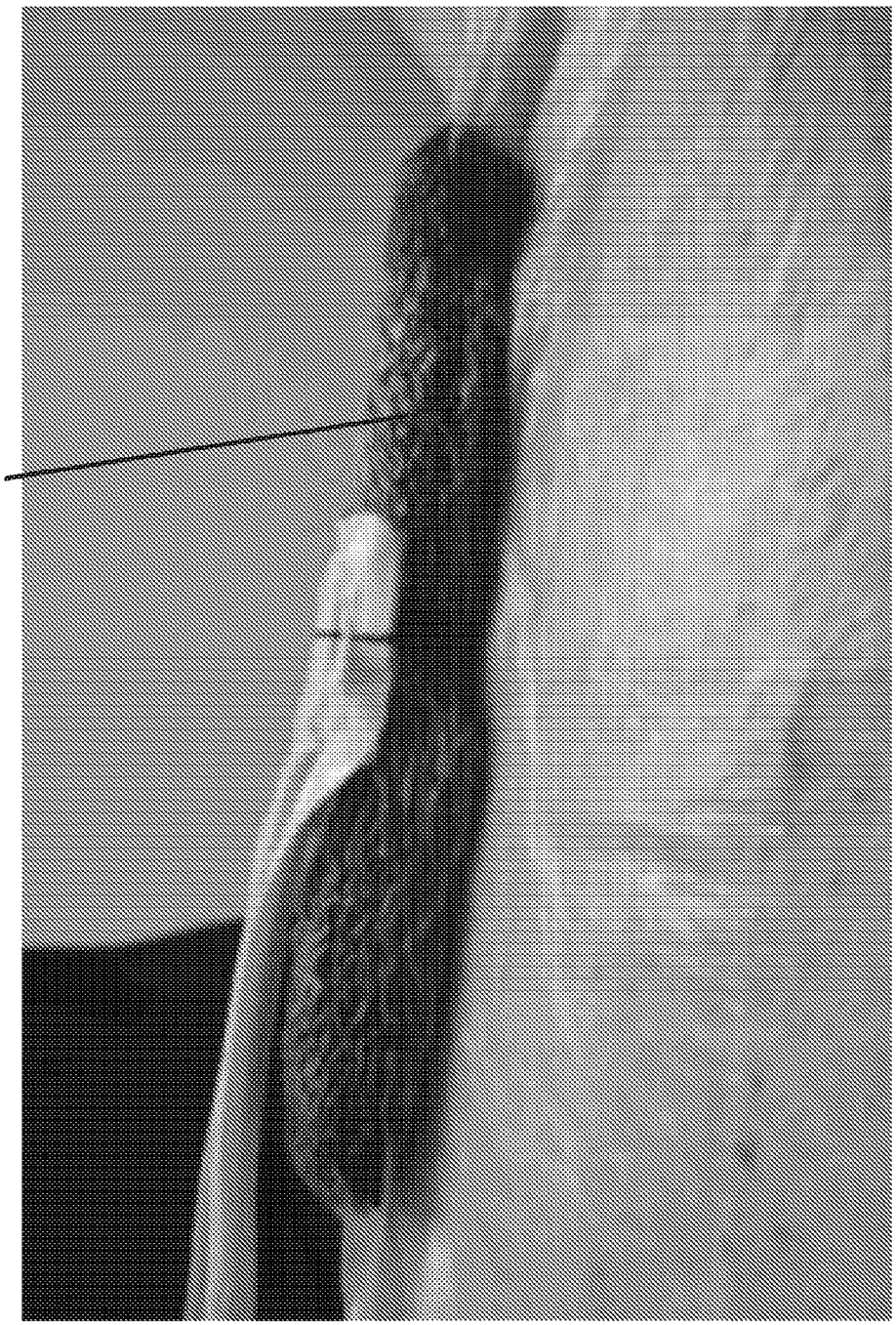
Figure 15E:
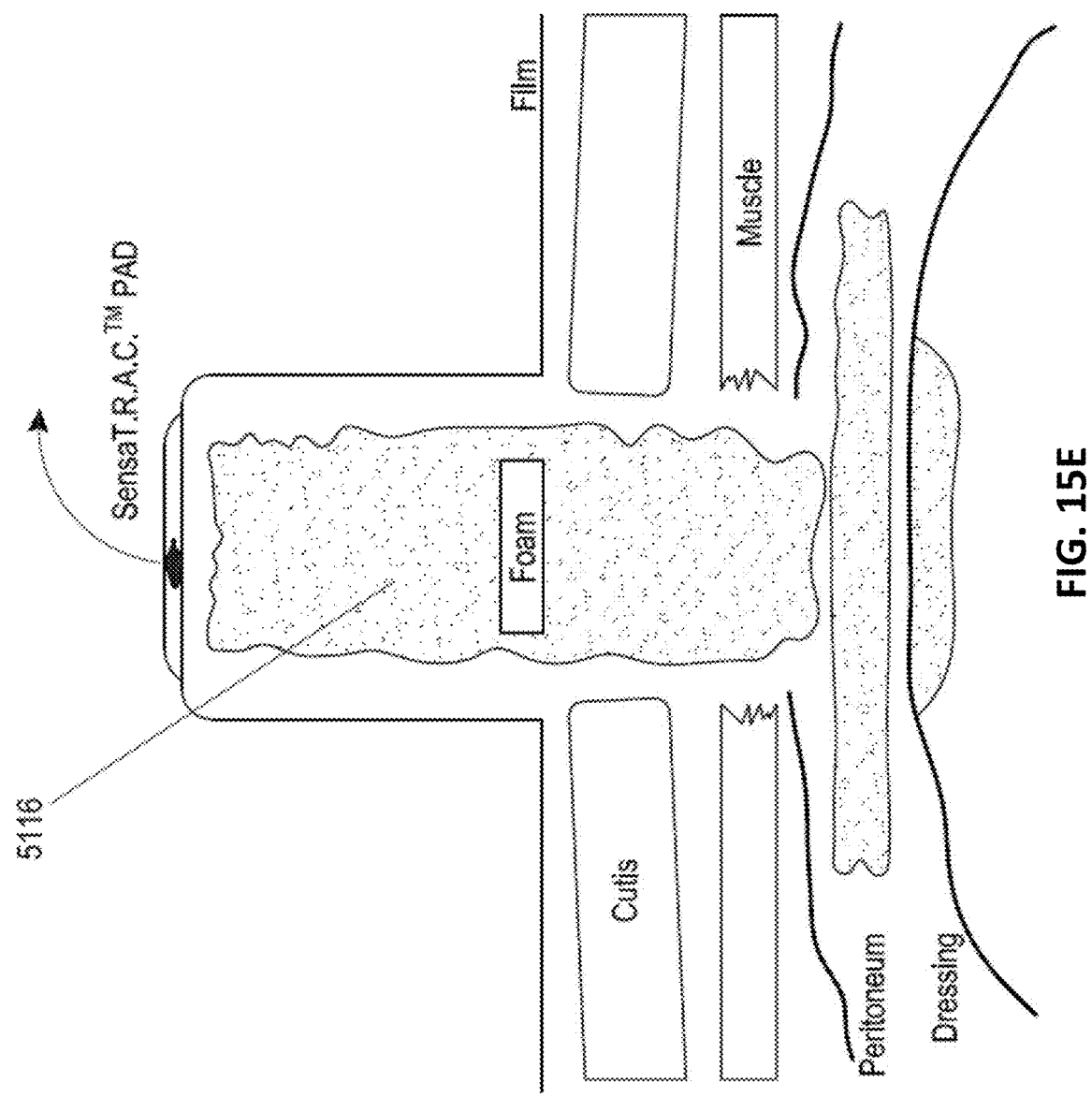

FIGS. 15A-E are photographs and a drawing of a prior art or alternative method for closing a wound, with some similarities to the methods of FIGS. 7-14G. Here, foam is placed under the muscle and fascia, followed by foam extending vertically out of the wound and folded over. Such a method may provide enhanced closure of the dermis but possibly not at the fascia level. In alternative embodiments, such a configuration may be combined with a stabilizing structure such as those disclosed herein this section and elsewhere in the specification, by providing a folded over foam layer 5116 that bulges out of the wound. FIG. 15E is a cross-sectional drawing of the prior art or alternative method.

Further details regarding the wound closure devices, stabilizing structures, related apparatuses and methods of use that may be combined with or incorporated into any of the embodiments described herein are found elsewhere throughout this specification and in International Application No. PCT/US2013/050698, filed Jul. 16, 2013, published as WO 2014/014922 A1, the entirety of which is hereby incorporated by reference.

The Stabilizing Structures of FIGS. 16-19D

Figure 16:
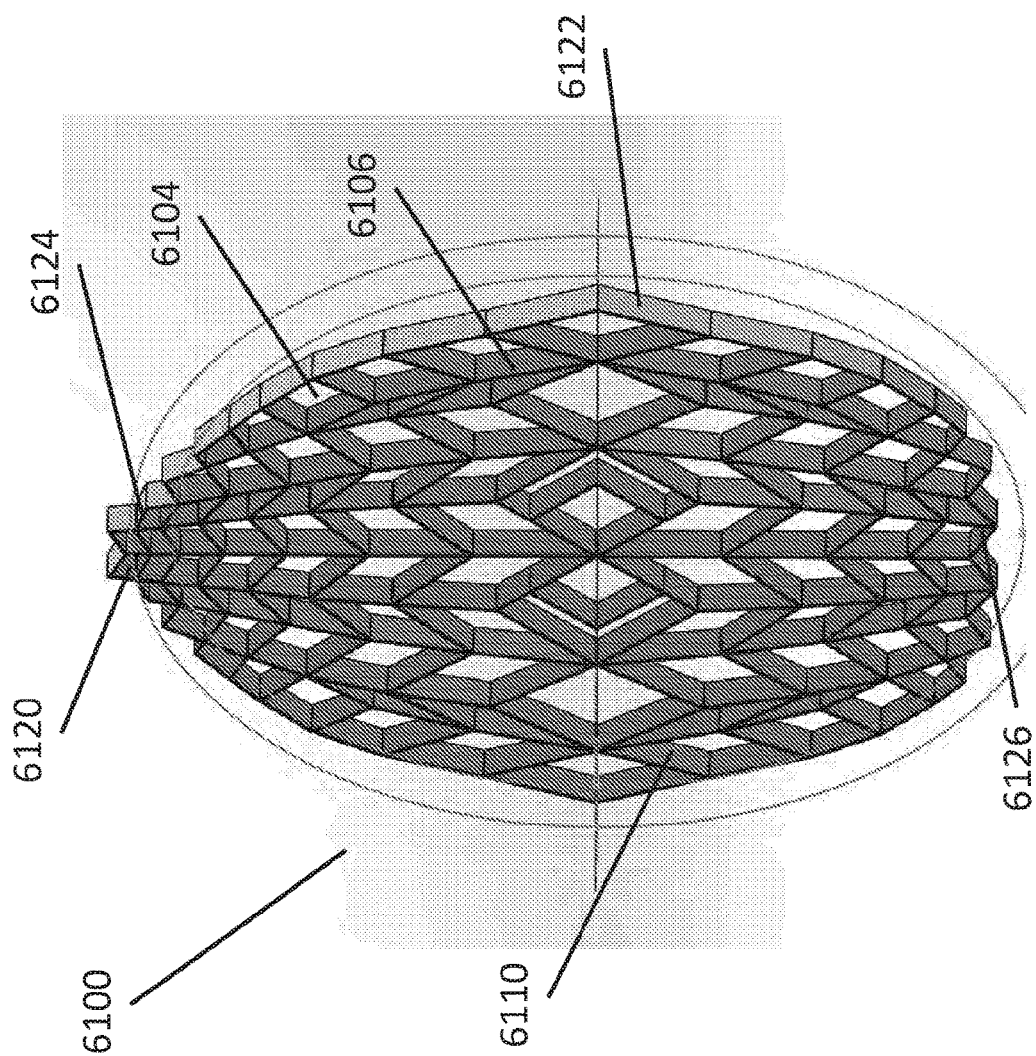
FIG. 16 illustrates an embodiment of a stabilizing structure.

FIG. 16 is a drawing of an embodiment of a stabilizing structure 6100, similar to the stabilizing structures of FIGS. 2A-3E. Stabilizing structure 6100 may be constructed via any means described herein this section or elsewhere in the specification, such as via 3D printing and via the calculation method described in FIGS. 3A-3E. Further, stabilizing structure 6100 may be constructed from any material described herein this section or elsewhere in this specification such as the materials described in relation to FIGS. 2A-3E. Similar to the stabilizing structures of FIGS. 2A-3E, stabilizing structure 6100 comprises a plurality of elongate strips 6106 arranged in parallel or semi-parallel, whose longitudinal length can be aligned with the longitudinal axis of a wound. In embodiments, the elongate strips 6106 may also be arranged in a non-parallel fashion. The various cells within this stabilizing structure 6100 may have a variety of shapes and sizes. As was described in greater detail above, the length and shape of the elongate strips 6106, intervening members 6110, and cells 6104 may be designed so as to facilitate greater closure of the stabilizing structure.

In embodiments, the stabilizing structure of FIG. 16 differs from the stabilizing structures of FIGS. 2A-3E, due to the inclusion of an extended section 6120. Extended section 6120 comprises one or more additional cells that extend outward along the longitudinal axis of the stabilizing structure 6100. Extended section 6120 may allow the stabilizing structure to better fit within a long incisional wound. Further, the addition of extended section 6120 may serve to prevent pinching of the surrounding tissue during collapse of the stabilizing structure 6100. Extended section may comprise about 6 additional cell, 12 additional cells, 16 additional cells, 20 additional cells, 30 additional cells, or more than 30 additional cells.

As depicted in FIG. 16, extended section 6120 may include additional rows having progressively fewer cells across its width. For example, extended section 6120 may comprise a row of four cells, then a row of two cells, followed by another row of two cells. In some embodiments, a row of six cells precedes the row of four cells. The extended section 6120 extends beyond the outer edge of a virtual ellipse formed by the majority of the perimeter of the stabilizing structure along the longitudinal axis of the stabilizing structure. In certain embodiments, the extended section may extend from both ends of the stabilizing structure along the longitudinal axis. The extended section 6120 in some embodiments provides a stepped outer perimeter to the outer wall of the stabilizing structure at the longitudinal edges of the stabilizing structure, in contrast to the continuous outer perimeter along the sides of the stabilizing structure 6122.

Absent the extended section 6120, the stabilizing structure comprises non-stepped side walls along substantially the entire length of the oval. However, with the extended section, the additional rows may provide a stepped outer perimeter 6124 based on the additional rows, in contrast to the flattened oval end of the stabilizing structure 6126. Further embodiments of the extended section will be described in more detail below in relation to FIGS. 17A-17E.

FIGS. 17A-17E are drawings and pictures of embodiments of stabilizing structure 6200, similar to the stabilizing structures of FIGS. 2A-3E and FIG. 16. Much like the stabilizing structures disclosed elsewhere in the specification, stabilizing structure 6200 comprises elongate strips 6206, cells 6204, and intervening members 6210. Stabilizing structure 6200 further comprises extended sections 6220 at both ends of the longitudinal axis of the stabilizing structure. As described above in relation to FIG. 16, extended sections 6220 may allow the stabilizing structure to better fit within the contours of a wound. Further, extended sections 6220 may prevent pinching of the surrounding tissue after collapse of the stabilizing structure. As described above, extended section may comprise multiple cells.

The stabilizing structures of FIGS. 17A-17E and any of stabilizing structure disclosed herein this section or elsewhere in the specification may be produced in a variety of sizes. The possible size and shape of an actual wound may vary dramatically in size and shape, thus suitable stabilizing structures may also be prepared in a variety of sizes. For example, the length of an un-collapsed stabilizing structure may be approximately at least 25 mm, 50 mm, 75 mm, 100 mm, 125 mm, 150 mm, 175 mm, 200 mm, 250 mm, 300 mm, 350 mm, 400 mm, 450 mm, 500 mm, 750 mm, or greater than 750 mm. In certain embodiments, the width of an un-collapsed stabilizing structure may be at least 10 mm, 15 mm, 25 mm, 35 mm, 50 mm, 75 mm, 100 mm, 125 mm, 150 mm, 175 mm, 200 mm, 250 mm, 300 mm, 350 mm, 400 mm, 450 mm, 500 mm or greater than 500 mm.

Figure 17A:
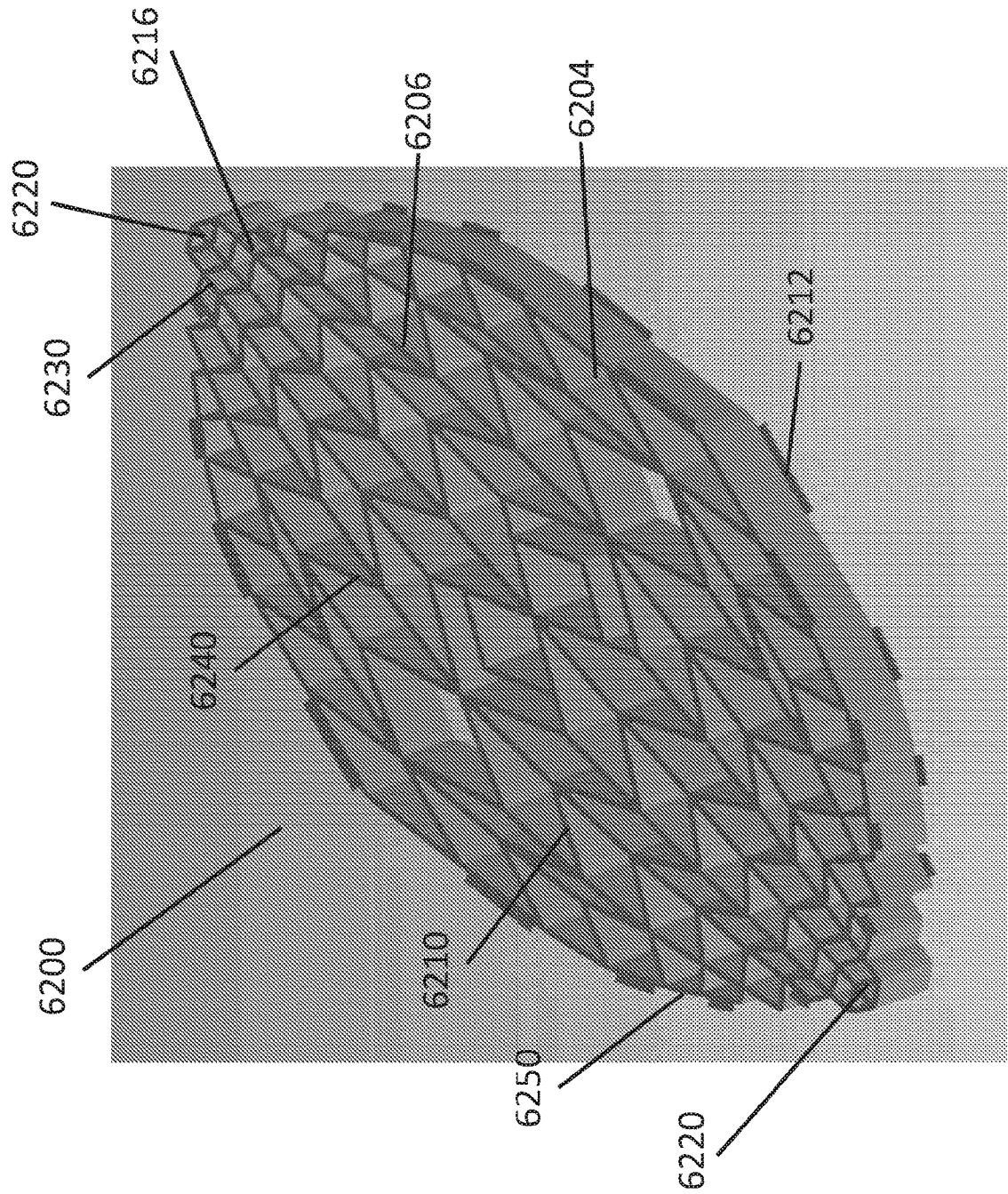
FIGS. 17A-E are drawings and photographs of an embodiment of a stabilizing structure.
Figure 17B:
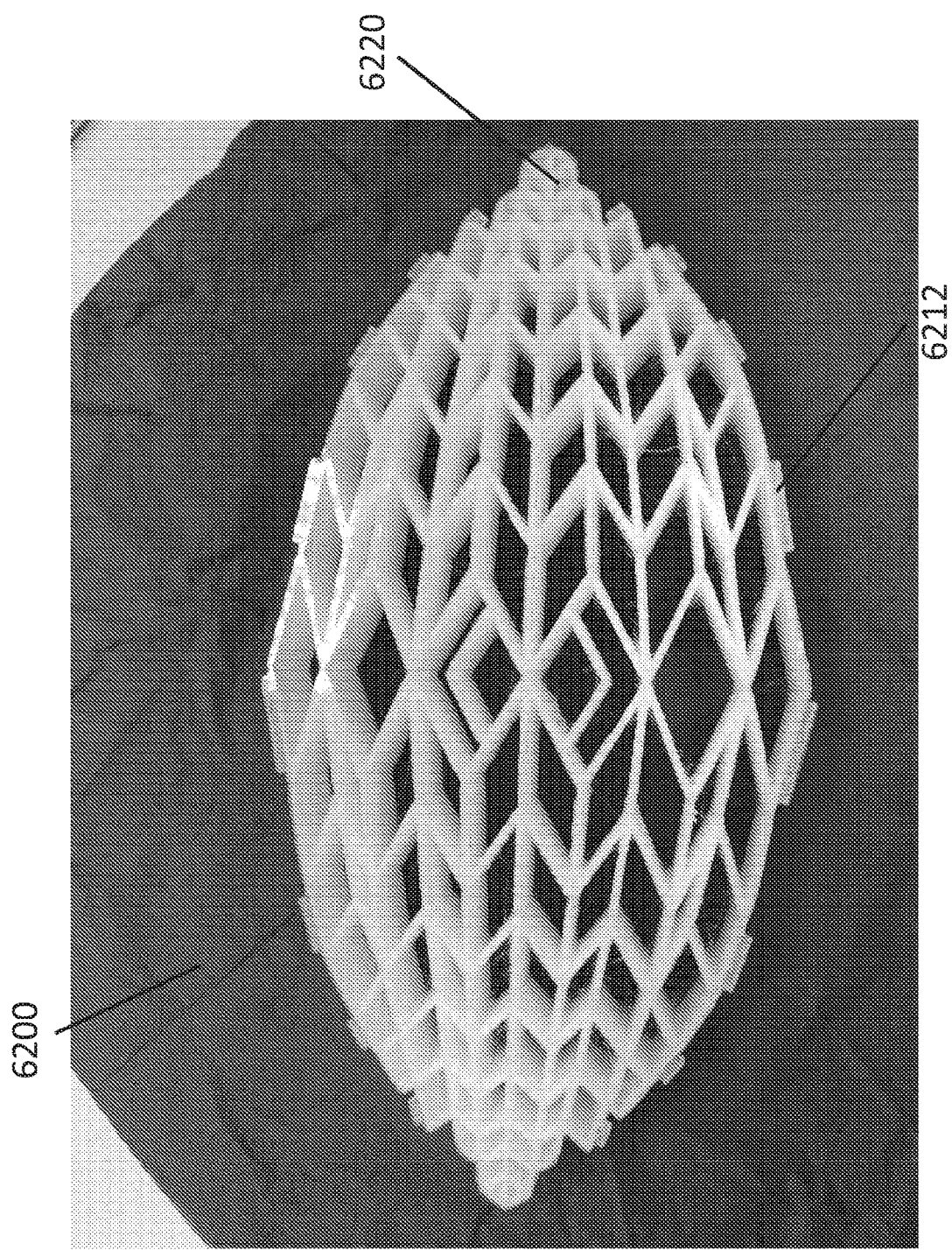
Figure 17C:
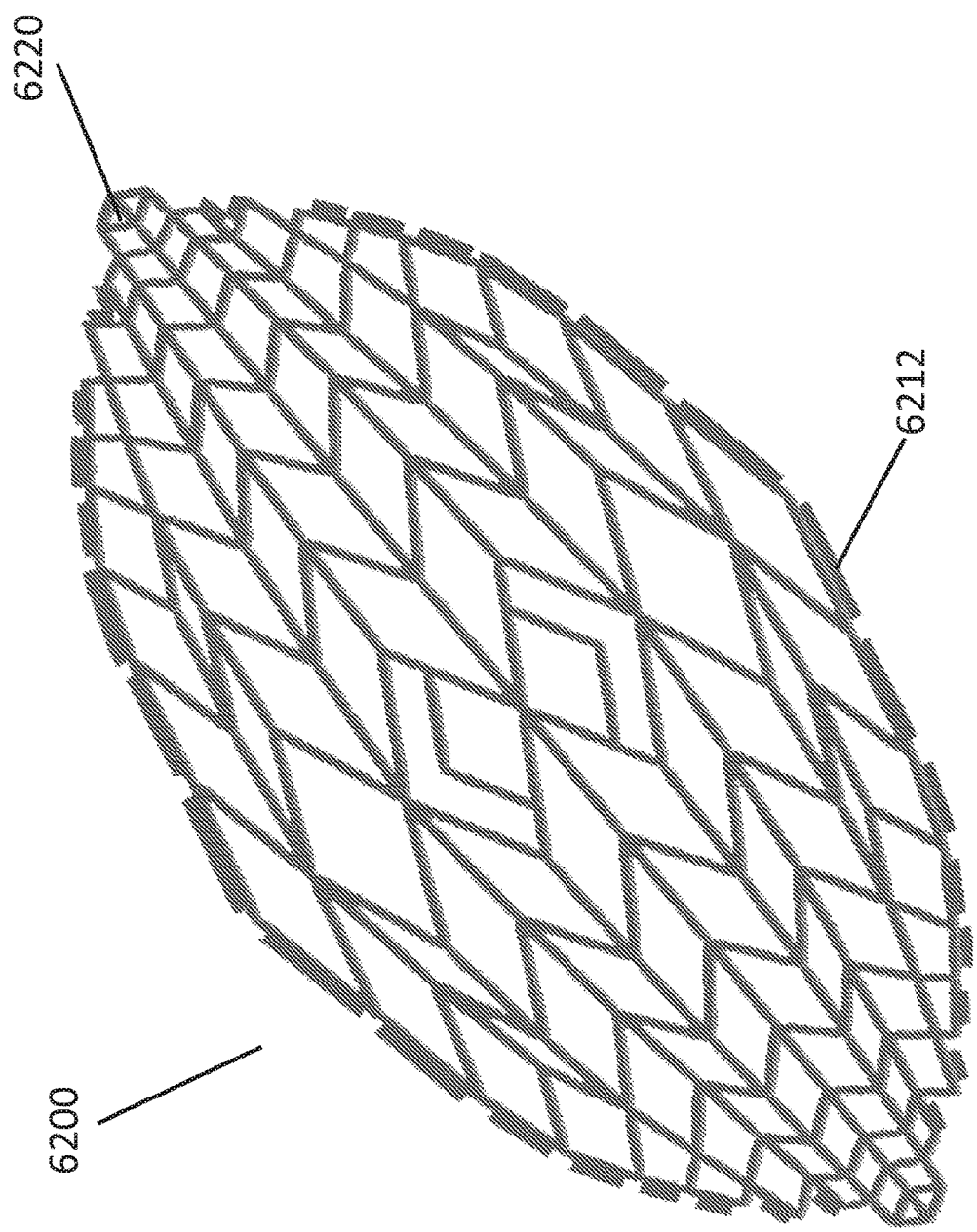
Figure 17D:
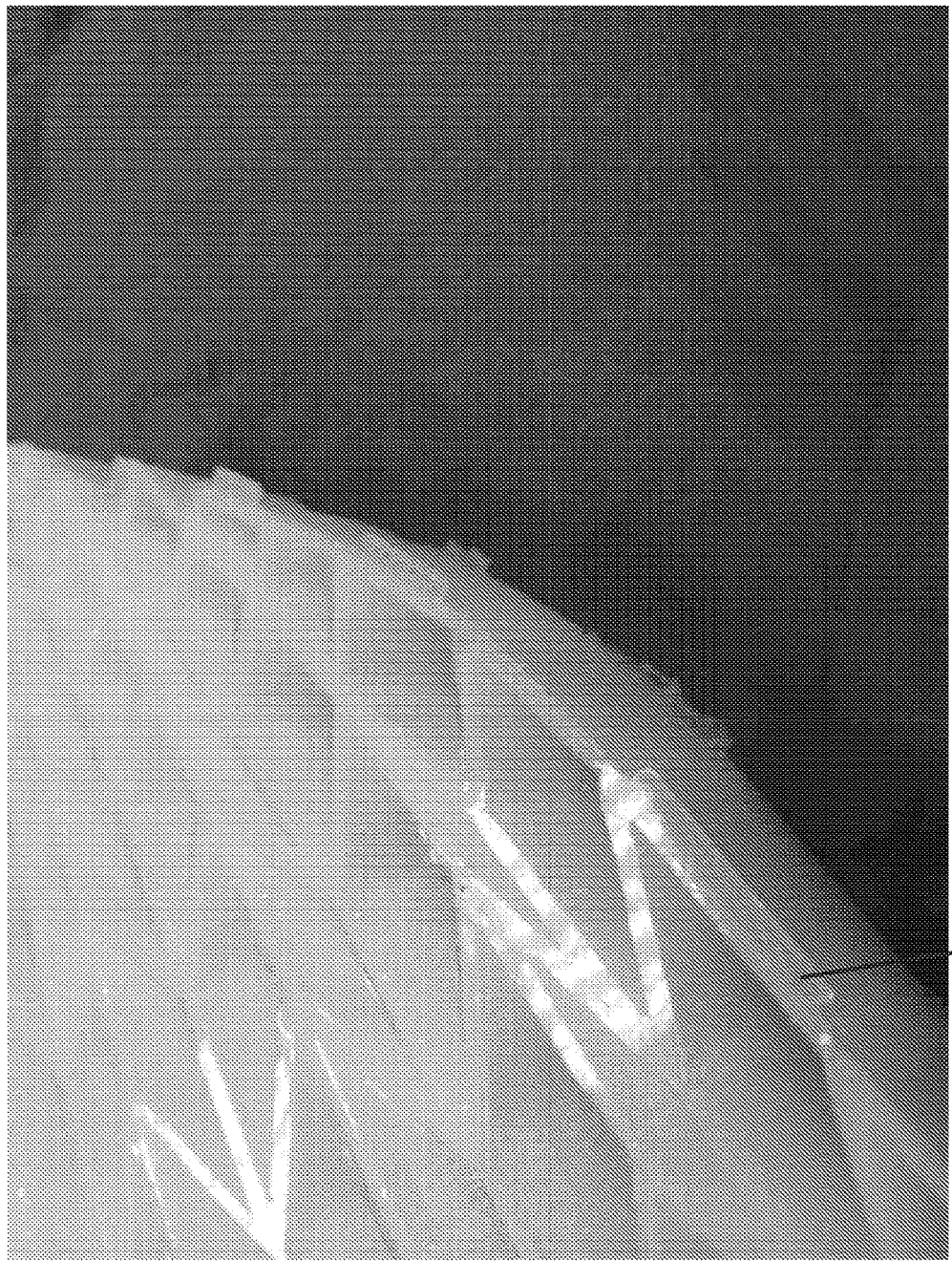
Figure 17E:
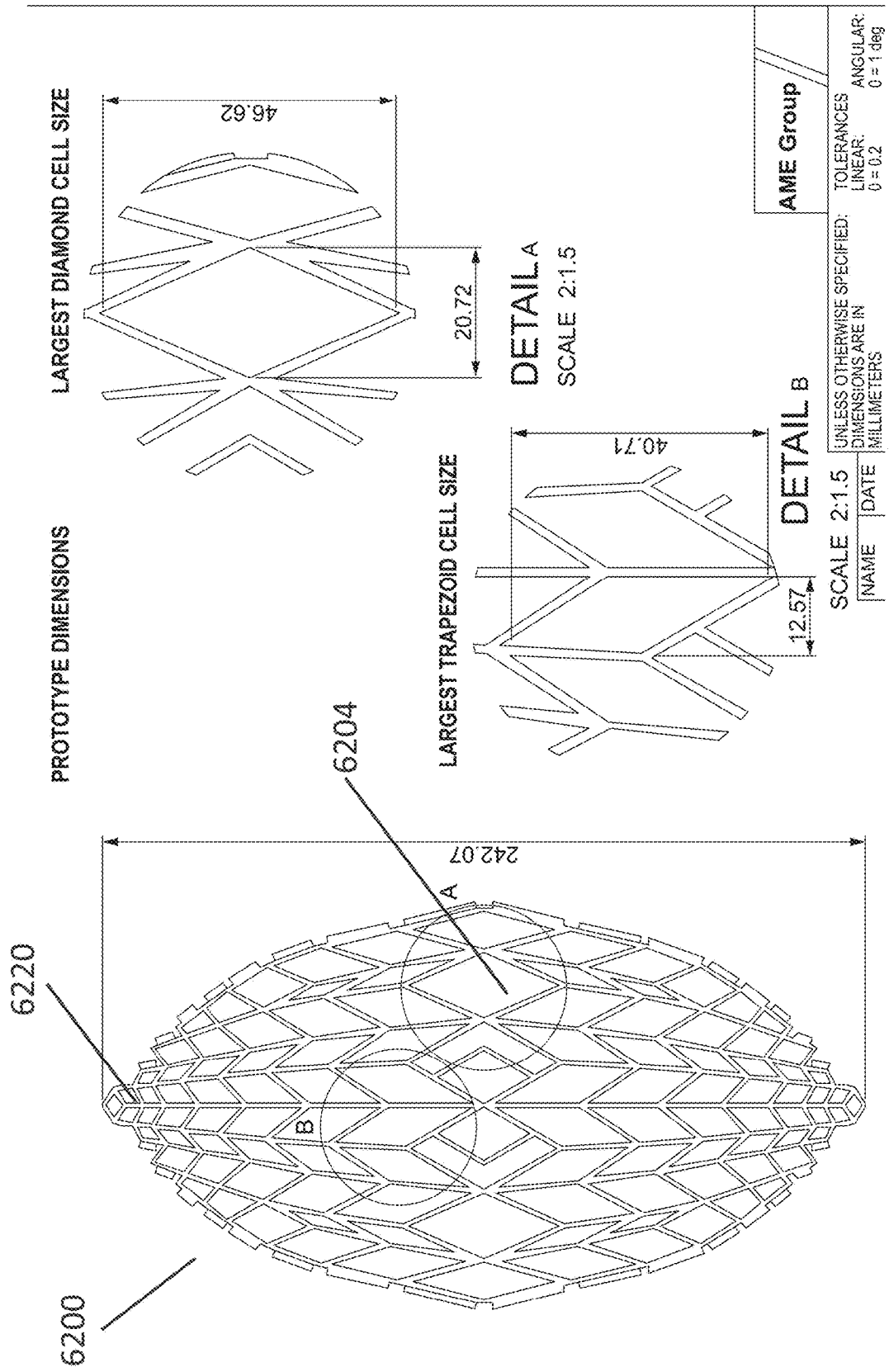

As depicted in FIG. 17E, in some embodiments the un-collapsed stabilizing structure may have a length of approximately 242 mm. However, the stabilizing structure may be of any size disclosed herein this section or elsewhere in the specification. The cells 6204 of the stabilizing structure may be of a variety of sizes, for example the width of a cell 6204 may be approximately at least 5 mm, 10 mm, 15 mm, 20 mm, 25 mm, 30 mm, 50 mm, or more than 50 mm. For example, the length of a cell may be approximately at least 5 mm, 10 mm, 15 mm, 20 mm, 25 mm, 30 mm, 50 mm, or more than 50 mm.

In some embodiments, extended sections 6220 may comprise a first row of four cells, followed by a row of two cells, followed by another row of two cells. The row of four cells may be preceded by a row of six cells. However, in further embodiments, the extended section may comprise various numbers of cells per row and different numbers of rows. For example, extended section may comprise 1 row, 2 rows, 3 rows, 4 rows, 5 rows, 6 rows, or more than 6 rows. In embodiments, the rows may comprise 1 cell, 2 cells, 3 cells, 4 cells, 5 cells, 6 cells, 8 cells, 10 cells, 16 cells, or more than 16 cells.

Returning to FIG. 17A, in certain embodiments, the extended section may comprise a series of cells 6104 comprising walls that are semi-parallel 6230 to the longitudinal axis of the stabilizing structure. These cell walls contrast with cell walls elsewhere in the stabilizing structure which comprise walls that run at an angle 6240 to the longitudinal axis of the stabilizing structure 6200.

In embodiments of the stabilizing structure comprising extended sections 6220, elongate members 6206 closest to the central longitudinal axis of the stabilizing structure extend further along the longitudinal axis than embodiments of the stabilizing structure that do not comprise an extended section. For example, the innermost elongate strips are the longest strips, while the next innermost strips are the second longest and so on. The presence of the extended sections causes the stabilizing structure when viewed from above to appear to be more eye-shaped rather than more oval-shaped.

As depicted in FIG. 17A-C, in embodiments, the stabilizing structure 6200 may be oculiform. An oculiform shape may appear to be shaped like a human eye, with curved upper and lower edges converging to points at either longitudinal pole in the corners of the eye. Here, the outer walls curve inward 6250 to converge at the extended sections 6220. This shape is in contrast to a more diamond shape (not shown) where the outer walls would converge in a straight line to extended section 6220. However, in some embodiments, the stabilizing structure may be in the form of a diamond, rather than an oculiform.

Stabilizing structure 6200 further comprises tabs 6212 extended outward from the outer wall of the stabilizing structure 6200. Such tabs may extend outward from the top or the bottom of the stabilizing structure or both. The tabs may extend out from all outer cells of the stabilizing structure as depicted by FIG. 17C or the tabs may alternate as depicted in FIG. 17A. FIG. 17D is a photograph of a close up view of a tab 6212. The tabs may be constructed from any material described herein this section or elsewhere in the specification, such as those materials used for construction of the stabilizing structures. In certain embodiments, the tabs may be 3D printed as part of the stabilizing structure.

The tabs 6212 may further comprise an anchoring layer, such as those described above in relation to FIGS. 4-6B. This anchoring layer may be used to adhere the tabs to a layer of foam. In embodiments, the tabs may be coated in a suitable adhesive, allowing the tabs to be adhered to a layer of foam. The attachment of foam to the upper and lower layers of the stabilizing structure will be described in greater detail below in relation to FIG. 20A-22E. The tabs may further serve to extend outward above or below tissues surrounding the stabilizing structure or around other structures such as foam, wrapped around the perimeter of the stabilizing structure.

The stabilizing structures of FIGS. 17A-17E may be provided in a variety of sizes such as those described above in relation to FIGS. 2A-3E. As described above, it may be advantageous in a clinical setting to minimize adjustments to the size of the stabilizing structure, therefore a kit may be provided that includes stabilizing structures of various sizes that may be fit to a wound of the appropriate size. For example, the kit may comprise only two sizes of matrices, a large size and a small size. The larger size stabilizing structure may be at least about 1.25×, 1.5×, 1.75×, 2×, 2.5×, 3×, 4×, 5×, 6× or greater than 6 times the size of the smaller stabilizing structure.

Figure 18A:
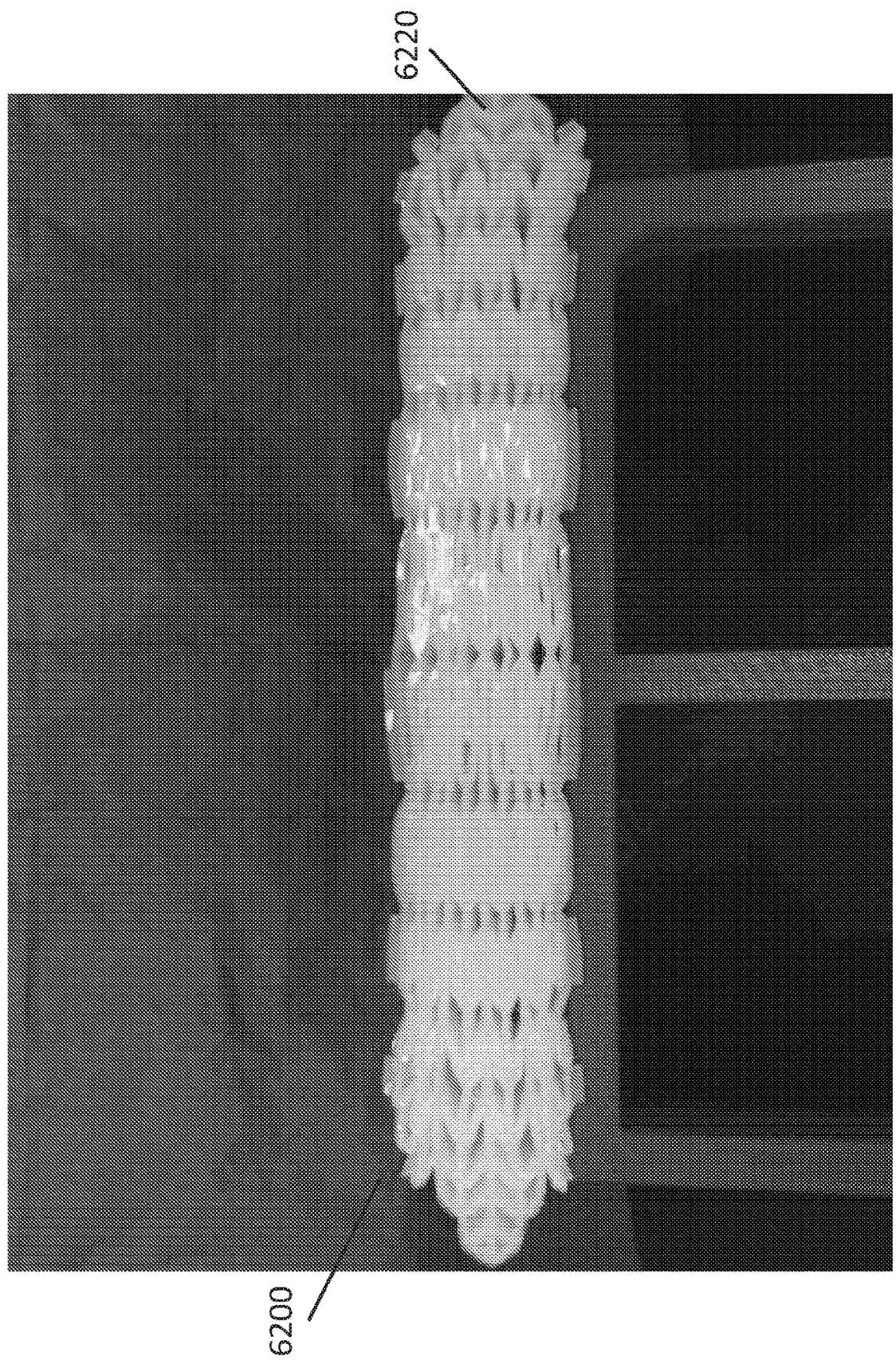
FIGS. 18A-D illustrate an embodiment of a collapsed stabilizing structure.
Figure 18B:
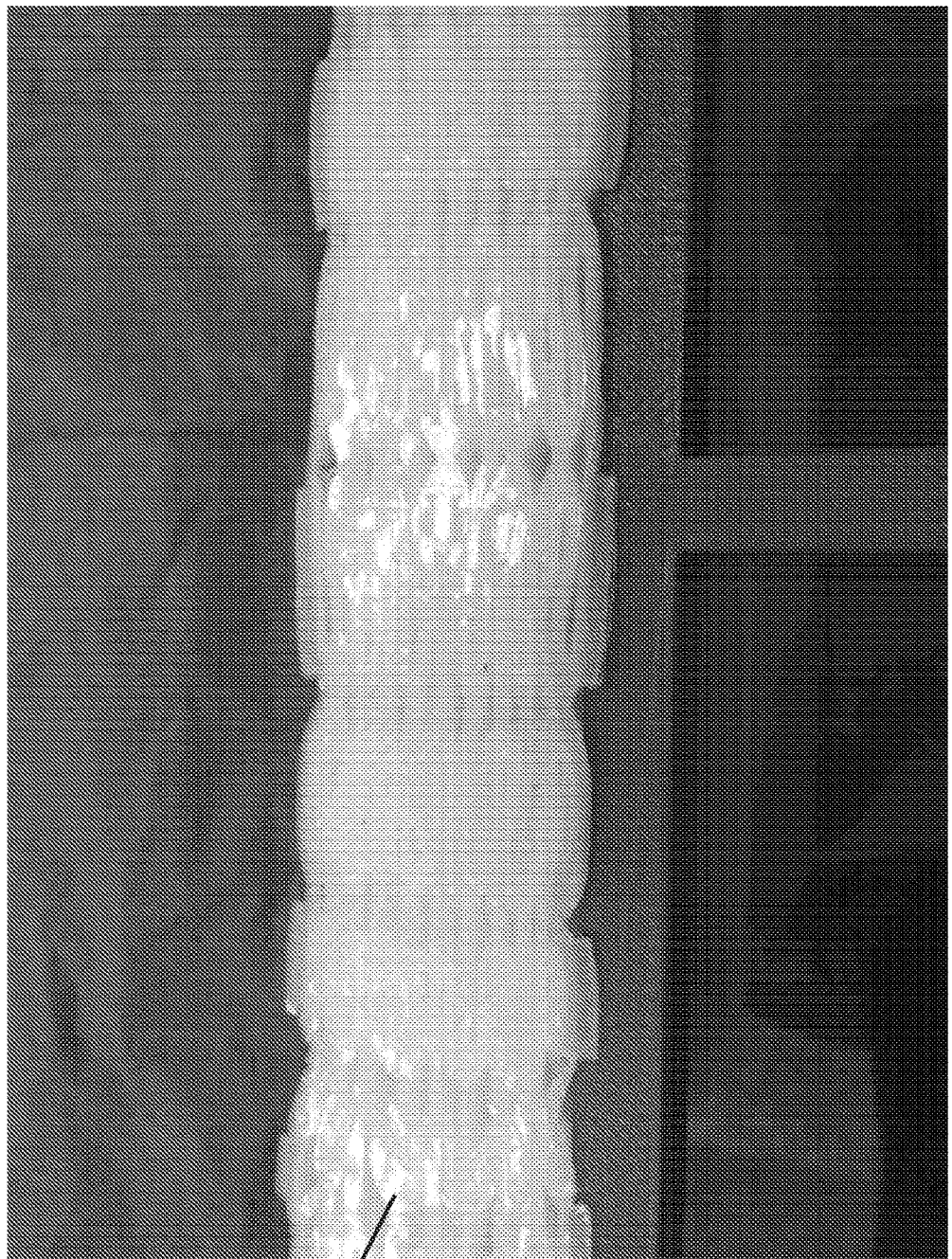
Figure 18C:
Figure 18D:

FIGS. 18A-D are photographs of multiple views of the stabilizing structure 6200 of FIG. 17B, in a collapsed state. During collapse, the length and height of the stabilizing structure remain approximately the same while the width decreases dramatically. As described above, the stabilizing structure may collapse in such a manner when subjected to negative pressure, thereby facilitating closure of the wound. As shown in FIG. 18A, in some embodiments, the extended sections 6220 may avoid collapse, however as shown in FIGS. 18C-D, in embodiments the extended section will collapse along with the remainder of the stabilizing structure.

Figure 19A:
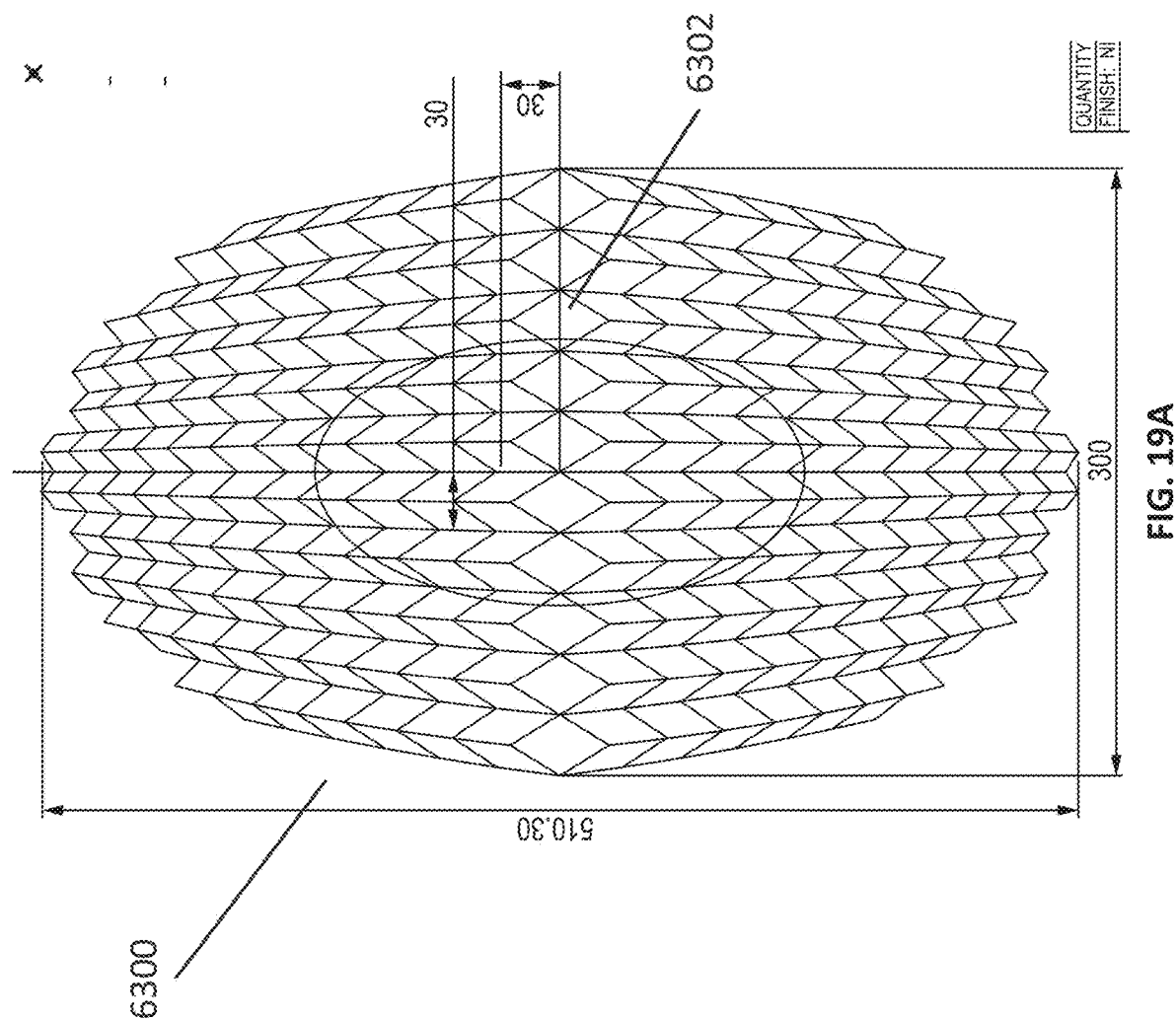
FIGS. 19A-B illustrate embodiments of stabilizing structures.
Figure 19B:
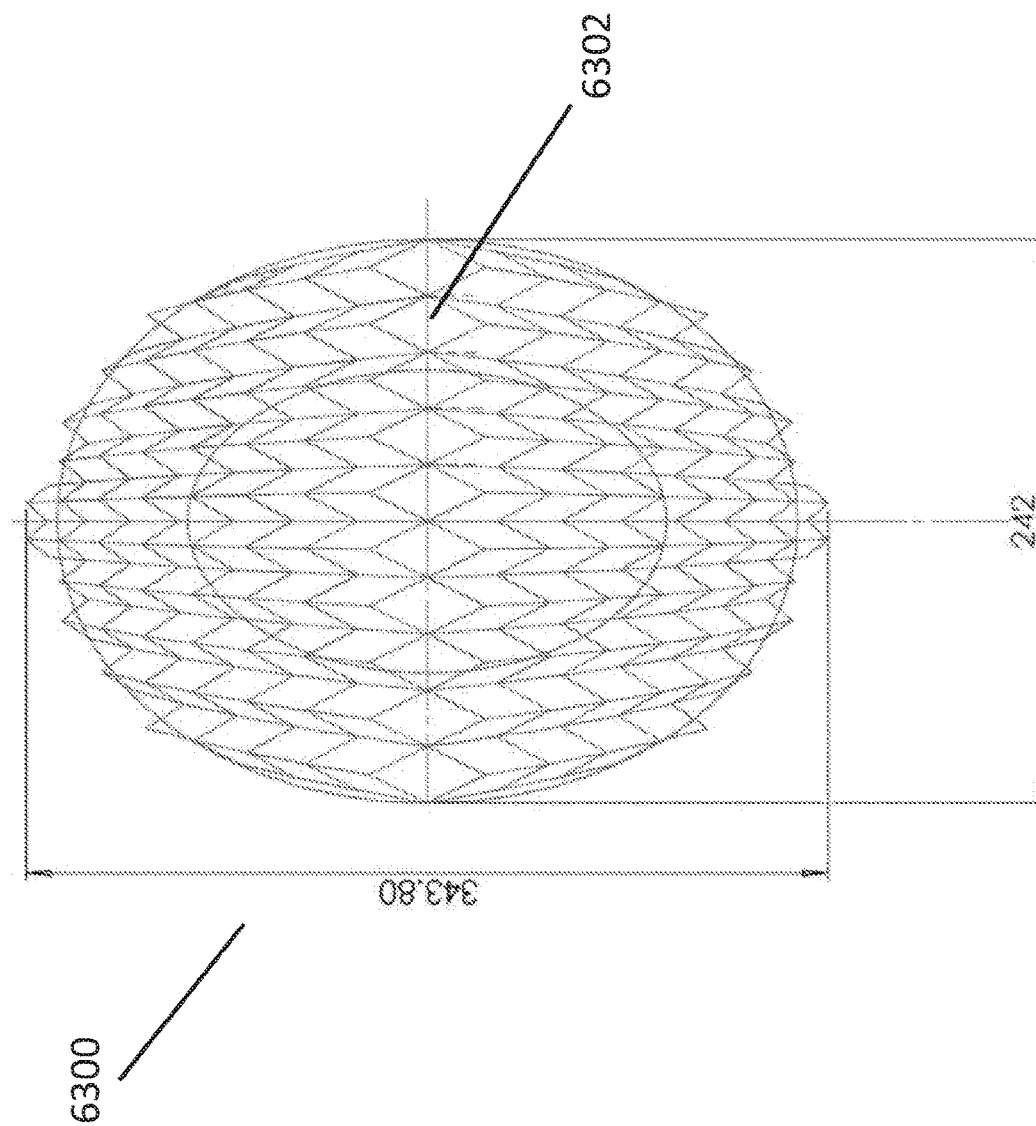

FIGS. 19A-B depict further embodiments of stabilizing structures 6300, similar to the stabilizing structures disclosed herein this section or elsewhere in the specification. The pattern of the stabilizing structures of FIGS. 19A-B comprises a series of cells symmetrically oriented around a mirror line 6302 along the minor axis of the stabilizing structure. In embodiments, the stabilizing structure of FIG. 19A has an un-collapsed width of 300 mm and a length of approximately 510 mm, while the stabilizing structure of FIG. 19B may have an un-collapsed width of 242 mm and length of 343 mm. The largest cells of the stabilizing structure of FIG. 19B may have a width of 30 mm. However, it will be understood by one of skill in the art that the stabilizing structures of FIGS. 19A-B may comprise any size and shape disclosed herein this section or elsewhere in the specification.

The Stabilizing Structures and Foam Layers of FIGS. 20A-22E

FIGS. 20A-22E are drawings and photographs of foam layers in combination with stabilizing structures such as those described above in relation to FIGS. 2A-3E and 16-19B. The foam layers described below may include any type of foam described herein this section or elsewhere in the specification. Possible foams may include open-celled and/or reticulated foams made from a polymer. Suitable foams include foams composed of, for example, polyurethane, silicone, hydrophobic materials, hydrophilic materials, open-celled materials, close-celled materials, mixed open and close-celled materials, reticulated materials, polyester, silicone, and/or polyvinyl alcohol. In embodiments, the foam layers described herein may include materials that change their properties over time. For example, a particular foam may be rigid initially but become more flexible when wet and/or lose rigidity over time due to degradation of the material.

The foam layers described in this section or elsewhere in the specification may have a variety of suitable thicknesses. For example, a foam layer may have a thickness of at least about 1 mm, 3 mm, 5 mm, 10 mm, 15 mm, 20 mm, 25 mm, 30 mm, 35 mm, 40 mm, 45 mm, 50 mm, or more than 50 mm thick. Single layers of foam may be laid atop one another to create a greater total thickness of foam, for example, a 15 mm thick layer of foam may be laid atop a 10 mm layer of foam to create a 25 mm total thickness of foam.

In certain embodiments, any of the foam layers described herein this section or elsewhere in the specification, may be pre-attached to an organ protection layer such as described above. For example, the lowest layer of foam, closest to the underlying organs, may be attached to an organ protection layer before placement within the wound, thereby saving the clinician the step of first placing an organ protection layer within the wound. In certain embodiments, the organ protection layer may be pre-attached to the underside of a stabilizing structure such as those described herein this section or elsewhere in the specification. In embodiments, the organ protection layer may be attached to the top of the bottom-most foam layer placed in the wound, thereby positioning the organ protection layer between the stabilizing structure and the bottom-most layer of foam. The organ protection layer may completely encase the bottommost layer of foam or stabilizing structure. The presence of a bottom layer of foam and/or organ protection layer may serve to protect the underlying bowel from damage due to direct interaction with the stabilizing structure.

FIGS. 20A-D are drawings and photographs of embodiments of a wound closure device 6350 comprising a stabilizing structure 6302 (similar to the stabilizing structures described above in relation to FIGS. 2A-3E and 16A-19D), a top porous foam layer 6352, and a bottom porous foam layer 6354. As will be described in greater detail below, top and bottom porous layers 6352 and 6354 may be shaped in any desired manner to conform to the shape of stabilizing structure 6302. In embodiments, the top and bottom layers of foam may be attached to the stabilizing structure 6302 before placement in the wound. Pre-attachment of the foam layers advantageously reduces the number of steps that need to be completed by the clinician As described elsewhere in the specification, stabilizing structure 6302 may comprise tabs 6304. These tabs advantageously provide a larger surface area for attachment of the foam layers to the stabilizing structure. Without the tabs, adhesive would necessarily need to be applied to the narrow upper edges of the stabilizing structure, potentially creating a weak or non-existent attachment. As described above, the tabs may be located on the top and bottom edges of the stabilizing structure. In embodiments, rather than adhesive, the tabs may be covered in anchors, such as those described above in relation to FIGS. 4-6B. The anchors act much like the adhesive, allowing the foam layers to be attached to the stabilizing structure prior to placement in the wound. The stabilizing structure may be pre-attached to the bottom layer of foam, top layer, or both. In certain embodiments, the adhesive may be applied to the central longitudinal elongate member of the stabilizing structure rather than to the tabs or other location. By applying adhesive only to the central elongate member, the stabilizing structure may collapse without resistance from the foam.

FIGS. 20A-D show embodiments of wound closure devices where the bottom foam is larger than the top foam, either by width, length, or both. Here, the foam extends outward from the stabilizing structure to create a lip, thereby allowing the lip of foam to extend above or below the surrounding tissue layers such as the fascia. The lip may serve to maintain the stabilizing structure in place by providing a downward force to resist the upward force applied by the expanding underlying viscera. In certain embodiments, the lip may need to be folded during placement within the wound bed so as to allow the closure device to be properly positioned. Thereafter the lip may unfold and extend into the surrounding tissues to aid in securing the device and applying negative pressure to the surrounding tissues.

In certain embodiments, the wound closure device of 6350 may be dome-shaped. In certain embodiments, the stabilizing structure may be dome shaped and/or the bottom and/or the top layer of foam may be dome shaped. The stabilizing structure may be shaped such that the upper surface is concave while the bottom surface is convex. In some embodiments the upper surface of the stabilizing structure is convex while the lower surface is concave. Any of the layers of foam (the top, bottom, middle or further layers of foam) may comprise an upper surface that is concave and a bottom surface that is convex. In some embodiments, any of the layers of foam (the top, bottom, middle or further layers of foam) may comprise an upper surface that is convex and a bottom surface that is concave.

The top layer may be sized to the top of the stabilizing structure, thereby facilitating closure of the wound to the size of the collapsed stabilizing structure. The lip extending outward from the matrix may be rounded so as to provide a better fit within the wound. In contrast, in the embodiment of FIG. 20E, the bottom layer may be smaller than the top layer. The top layer may advantageously prevent drawing of the drape down into the stabilizing structure or between the stabilizing structure and the edges of the wound.

Figure 20A:
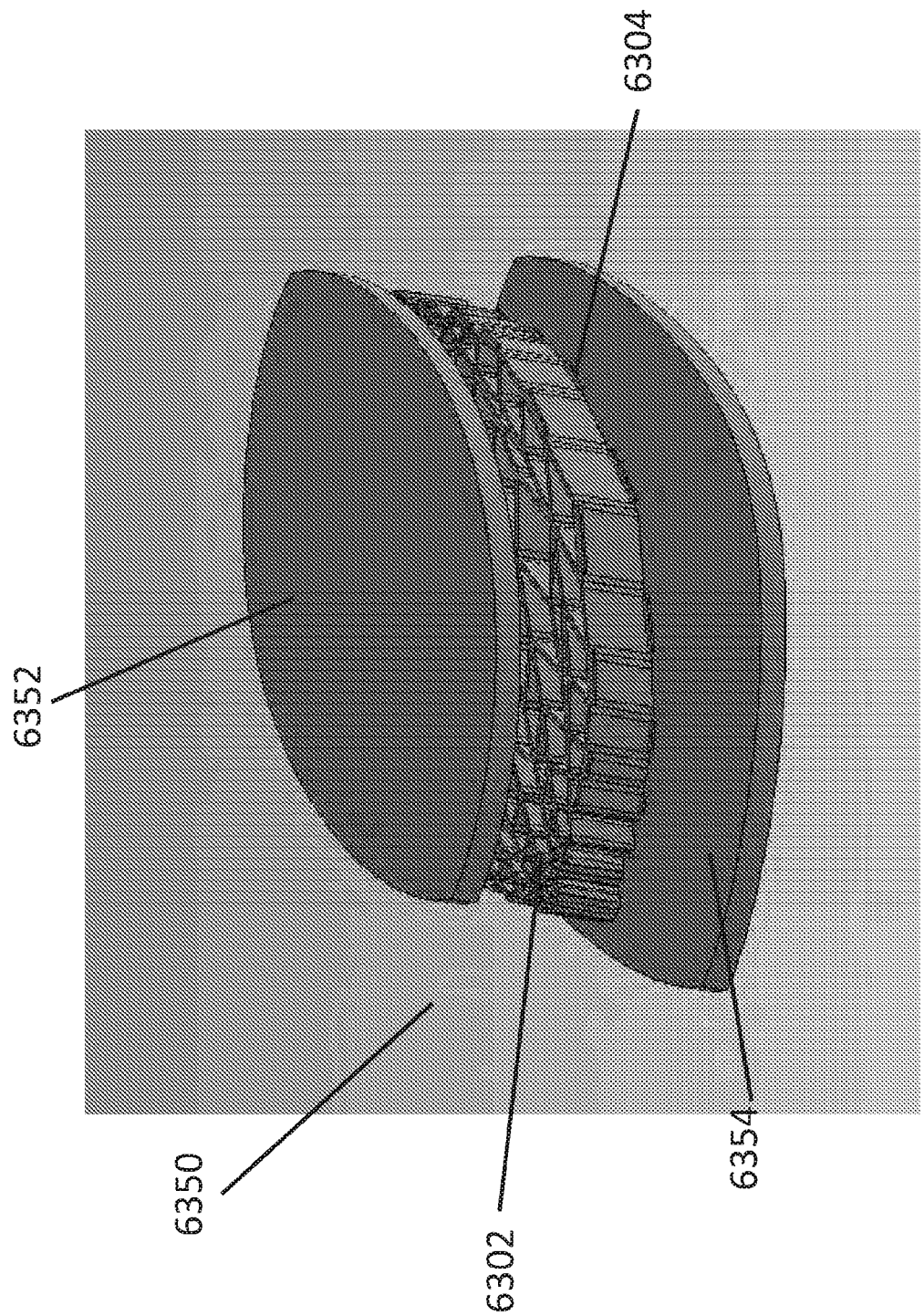
FIGS. 20A-G illustrate embodiments of stabilizing structures and foam layers.
Figure 20B:
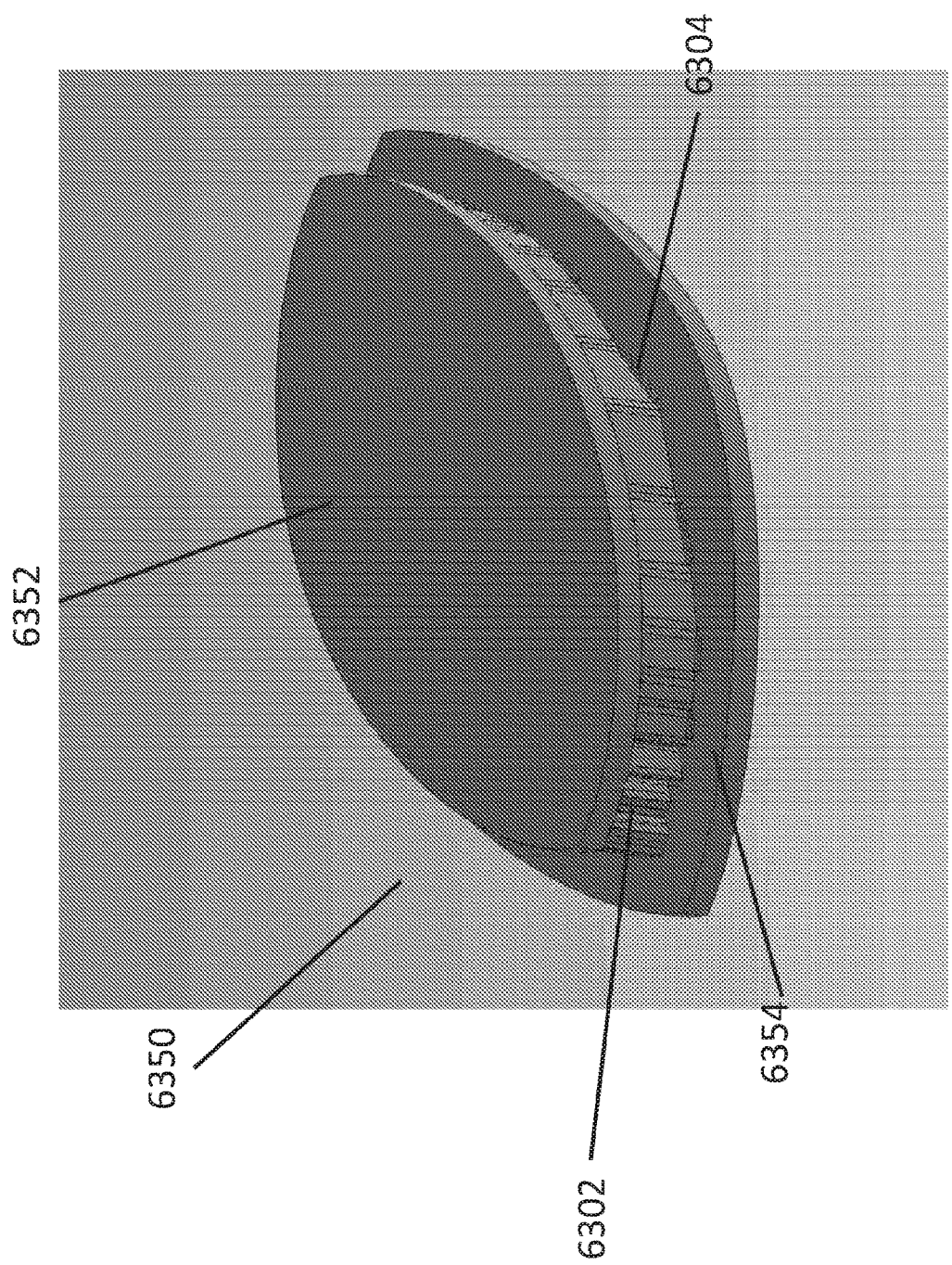
Figure 20C:
Figure 20D:

In certain embodiments, the foam layers may be of any thickness disclosed herein this section or elsewhere in the specification. The bottom layer of foam 6354 may be approximately 15 mm thick or approximately 10 mm thick. For example, the bottom foam 6354 of FIG. 20D is thicker than the bottom foam of FIG. 20C.

Figure 20E:
Figure 20F:
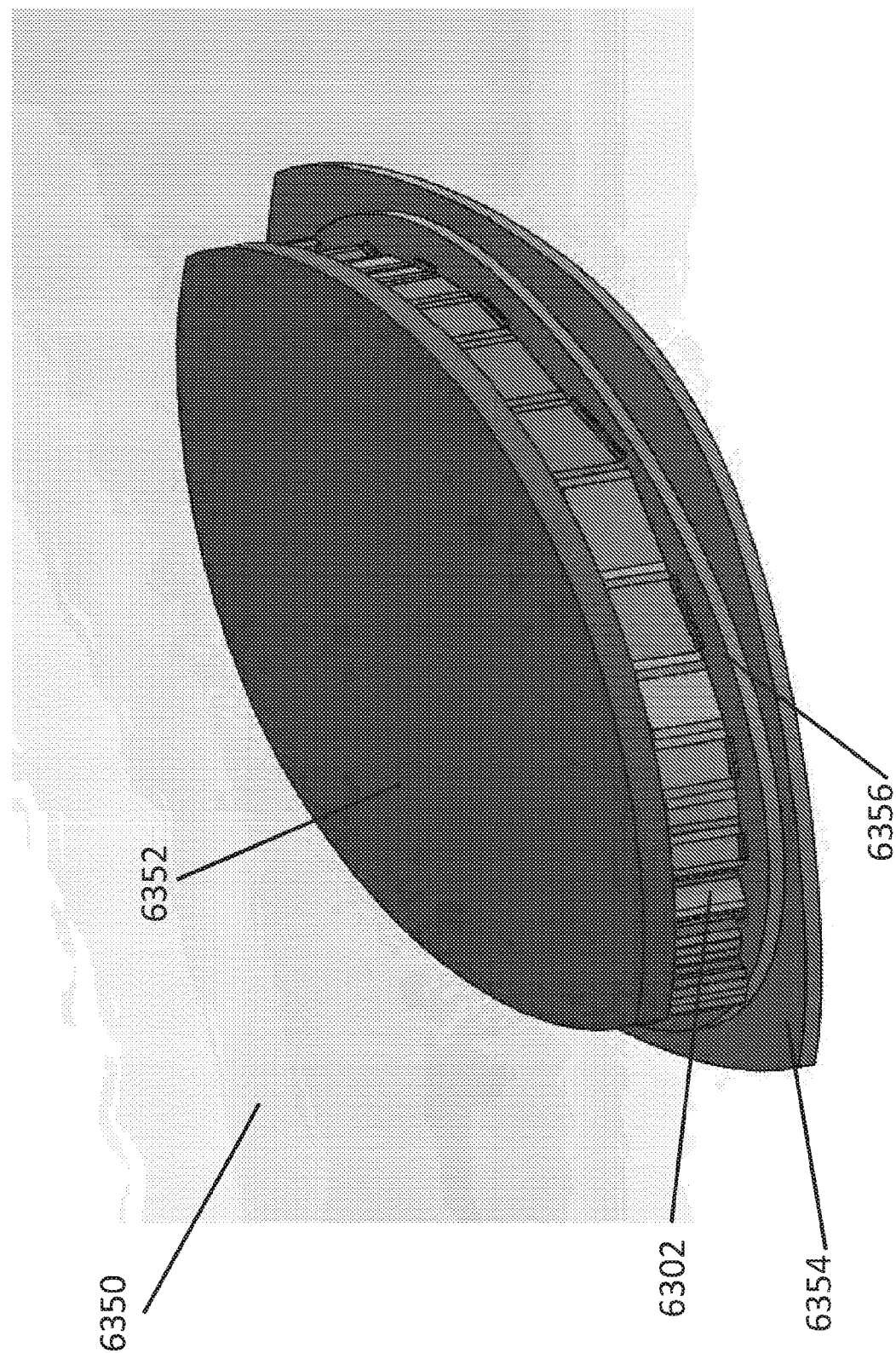
Figure 20G:
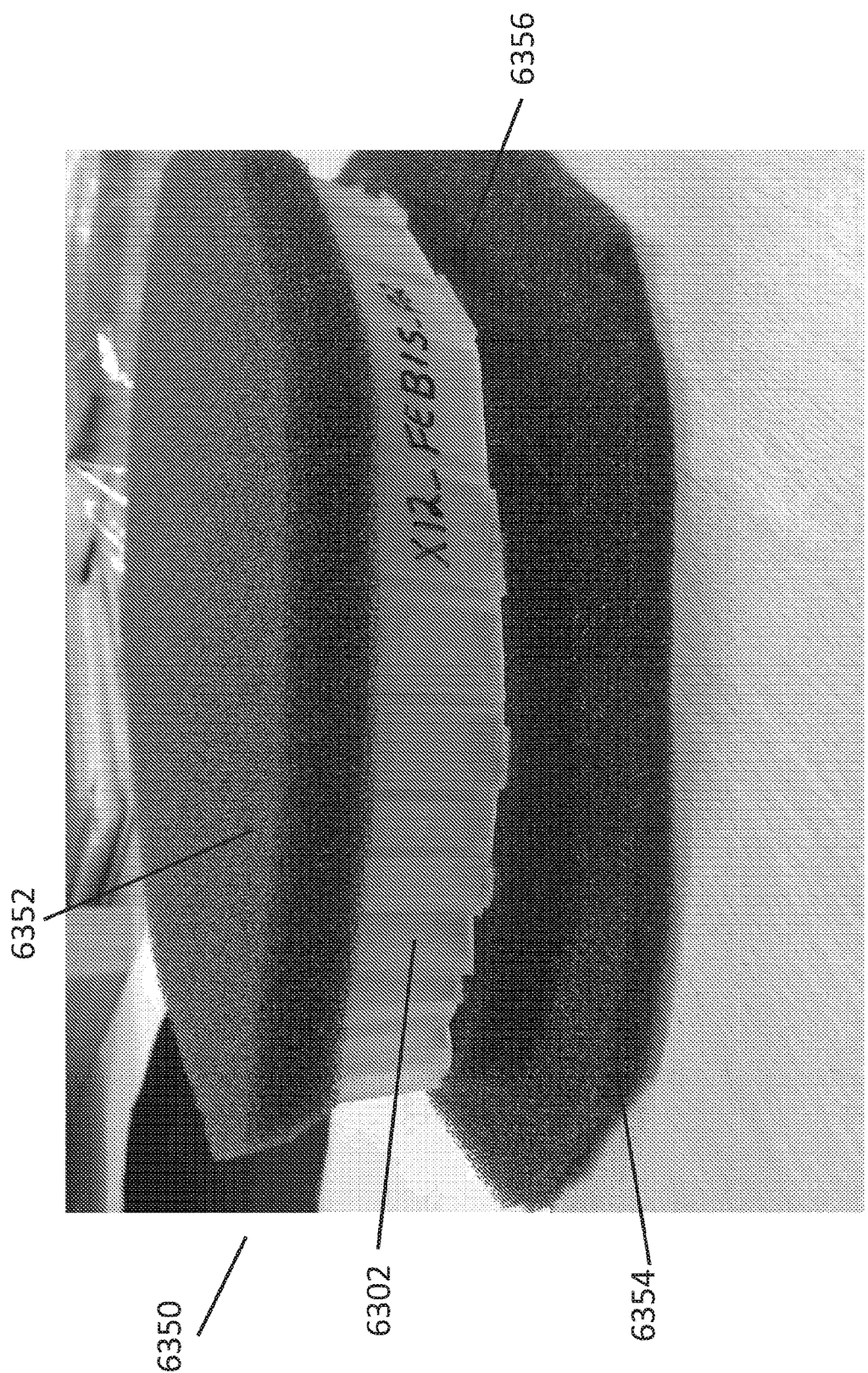

FIGS. 20F-20G depict an embodiment of a wound closure device involving a total of 3 layers of foam. Here, wound closure device 6350 comprises stabilizing structure 6302, top layer of foam 6352, bottom layer of foam 6354, and middle layer of foam 6356. The stabilizing structure may be pre-attached to the middle layer of foam, top layer of foam, or both. Further, the bottom layer of foam may be pre-attached to the middle layer of foam, or may be placed into the wound separately. In some embodiments, the top layer is 15 or 10 mm thick, the middle layer is 15 mm thick, and the bottom layer is 10 mm thick. Foam layers may be attached by any suitable means, such as via adhesive or anchors. As depicted in FIG. 20E, the bottommost layer of foam may comprise a lip that extends outward from the wound closure device into the surrounding tissue. As described above, such a lip may secure the device in place. The bottom layer of foam may be wider and/or longer than the middle and/or top layers of foam. In certain embodiments, in addition to the foam on the top and bottom of the stabilizing structure, foam may be attached to the entire outer perimeter of the stabilizing structure. Foam may be attached to the perimeter of the stabilizing structure via any suitable means, such as by adhesive or anchoring layer. Once foam has been applied to the perimeter of the stabilizing structure, the stabilizing structure will no longer be visible if there are also top and bottom layers of foam.

In embodiments of the foam layers of FIGS. 20A-20F, the layers of foam may comprise any type of suitable foam material described herein this section or elsewhere in the specification. For example, the foam may comprise "black foam" such as polyurethane and/or "white foam" comprising polyvinyl alcohol (PVA). In embodiments involving PVA foam, thinner foam layers may be needed as compared to other types of foam, because PVA foam is often more resilient and dense than other types of foam. Further, once PVA foam becomes wet it may also aid with lateral slip. In some embodiments, the foam layers may be combined with other fillers such as gauze, or other mesh/net products such as those on Fry and Kossel.

Figure 21:
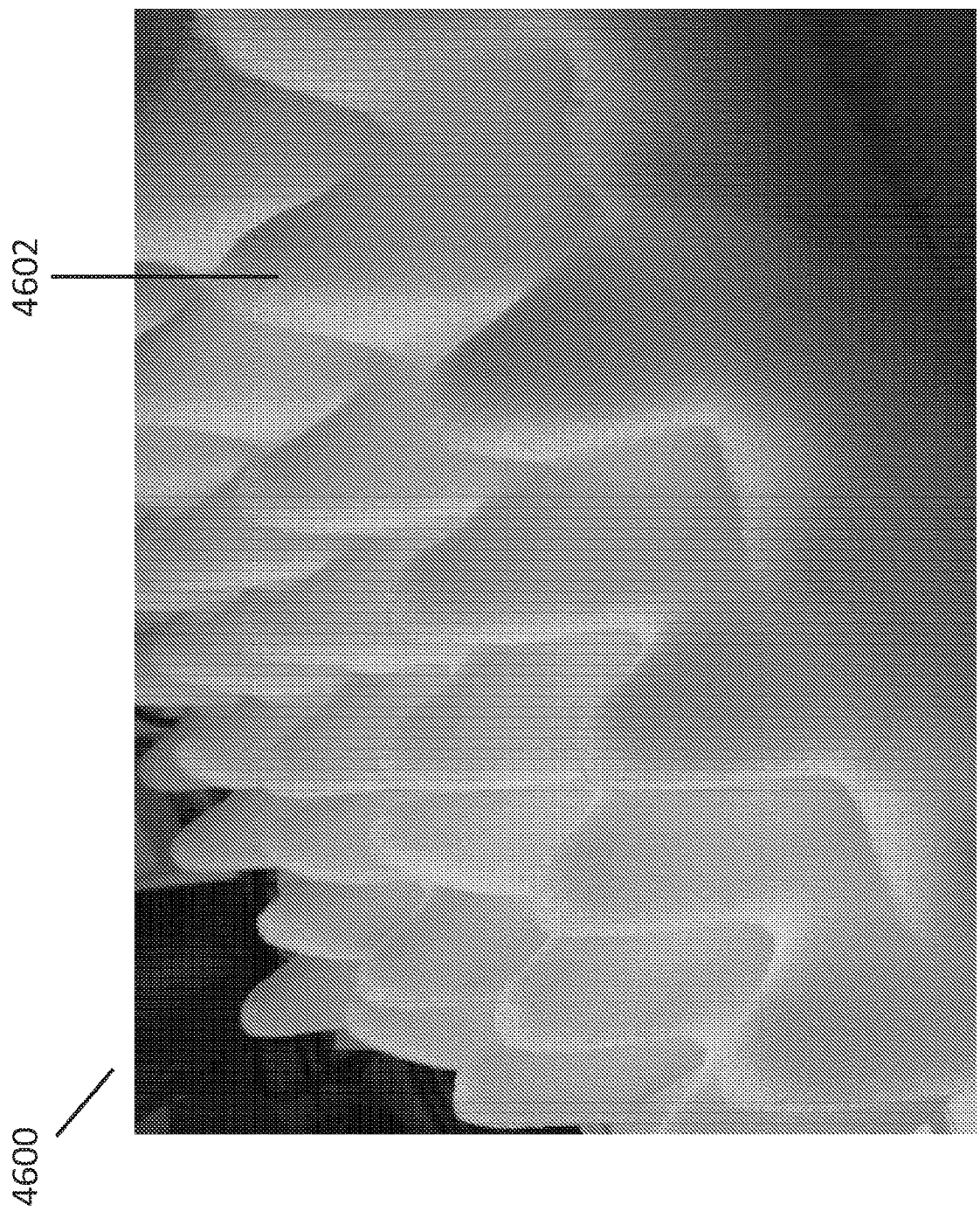
FIG. 21 illustrates an embodiment of a foam layer with fingers.

FIG. 21 is a photograph of an embodiment of a foam layer 4600 that may be used in combination with any of the stabilizing structures or wound closure devices described in this section or elsewhere in this specification. The foam layer of 4600 may be used in place of any foam layer described herein this section or elsewhere in the specification. As described in this section and elsewhere in the specification, the foam layer 4600 may be located above or below the stabilizing structure or wound closure device. In some embodiments, the foam layer 4600 is located both above and below the stabilizing structure or wound closure device. The foam layer 4600 can surround the perimeter of the stabilizing structure or wound closure device or completely surround the entirety of the stabilizing structure or wound closure device. The foam layer 4600 can be constructed from absorbent materials, materials configured to distribute fluid, or both.

The foam layer 4600 further comprises fingers 4602 that can extend from the foam layer into the stabilizing structure or closure device. For example, the fingers 4602 may extend into and around the gaps or cells depicted in the stabilizing structures described herein this section or elsewhere in the specification. The fingers 4602 may also extend around the outside of the perimeter of the stabilizing structure. In some embodiments, the fingers 4602 from one foam layer 4600 may extend through the interior or around the outside of the stabilizing structure to meet the fingers 4602 from a second foam layer 4600. Thus, one foam layer will be facing finger-side up, while a second foam layer may be facing finger-side down.

In some embodiments, the foam layer 4600 can have perforations or pre-cuts to allow portions of the foam layer 4600 to be easily torn away to shape the foam for a particular wound. In some embodiments, the fingers 4602 can extend at least about 1 mm from the surface of the foam layer, at least about 3 mm from the surface of the foam layer, at least about 5 mm from the surface of the foam layer, at least about 7.5 mm from the surface of the foam layer, at least about 10 mm from the surface of the foam layer, at least about 12.5 mm from the surface of the foam layer, at least about 25 mm from the surface of the foam layer, at least about 17.5 mm from the surface of the foam layer, at least about 20 mm from the surface of the foam layer, at least about 25 mm from the surface of the foam layer, or more than 25 mm.

In certain embodiments, the fingers 4602 can be varied so as to control the collapse of the stabilizing structure. For example, when a finger is extended into a particular cell of the stabilizing structure, the finger will prevent collapse of that particular cell. Therefore, a larger number of foam fingers extending into the stabilizing structure will reduce collapse more than a lesser number of foam fingers. For example, the fingers may extend into at least about: 10%, 20%, 30%, 50%, 75% or even 100% of the cells of the stabilizing structure, thereby further limiting collapse of the stabilizing structure.

FIGS. 22A-22E depict foams suitable for printing instructions. When placing a wound closure device such as those described herein this section or elsewhere in the specification, it may be difficult for the clinician to determine the proper orientation of the foam layer or other components of the wound closure device. Therefore, printing of symbols on the foam may make it easier for the clinician to properly orient the foam layer. Although not shown, any of the symbols or printing disclosed herein this section or elsewhere in the specification may be applied to different structures of the wound closure device, such as the stabilizing structure.

Figure 22A:
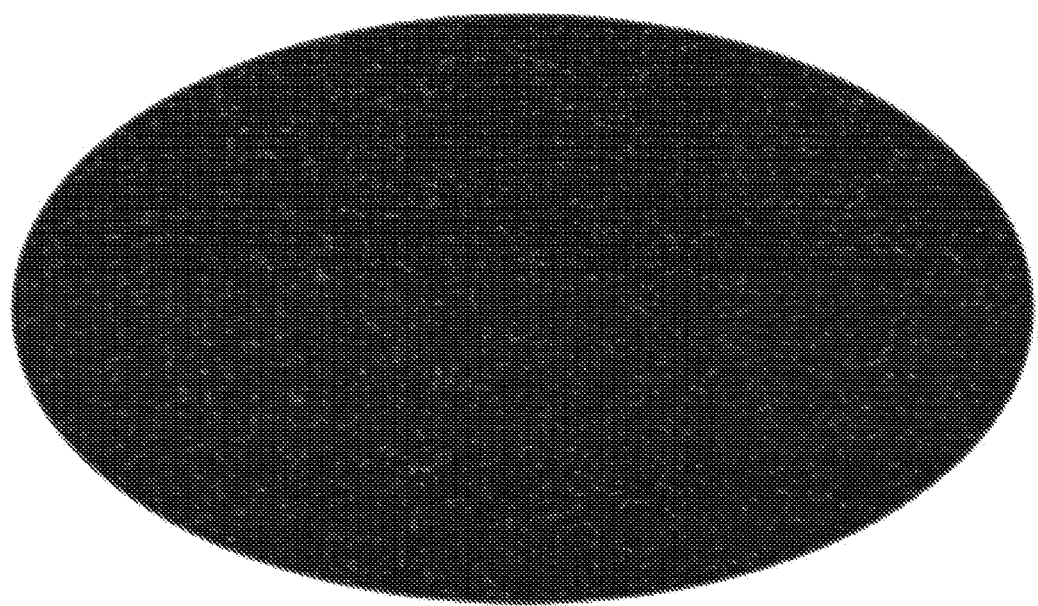
Figure 22C:
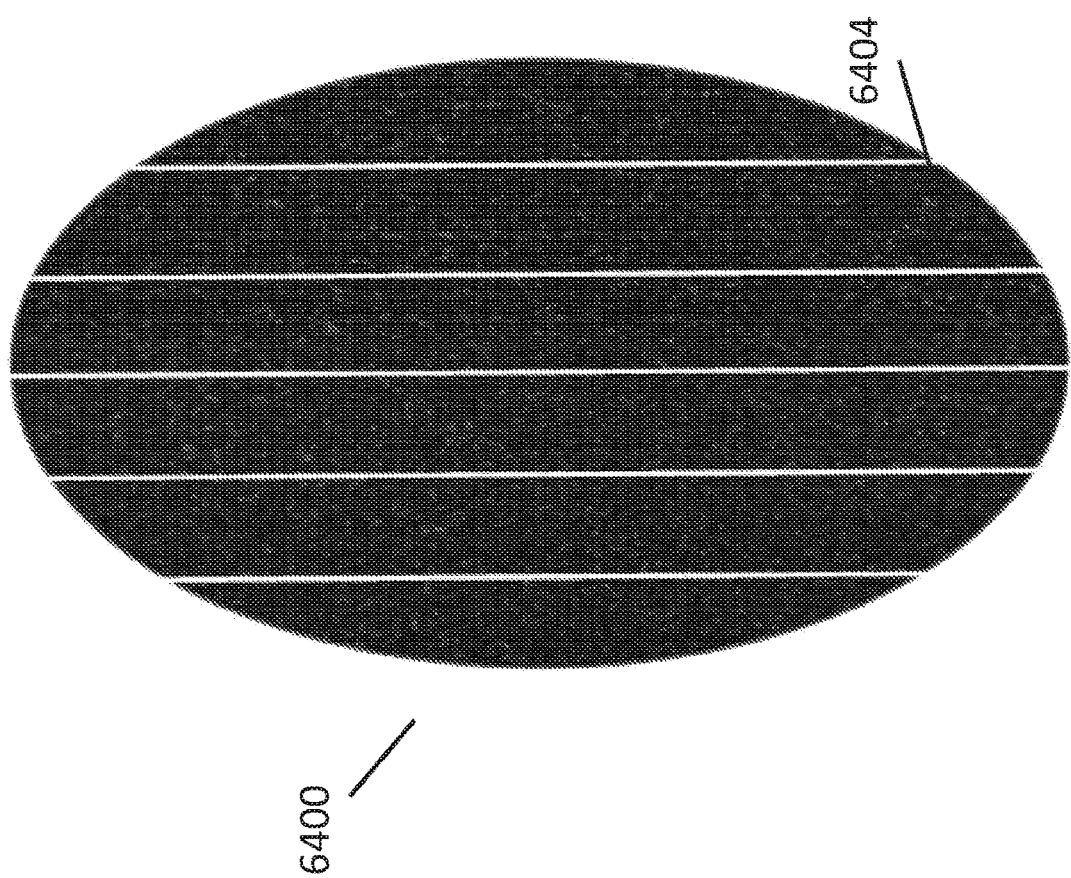
Figure 22D:
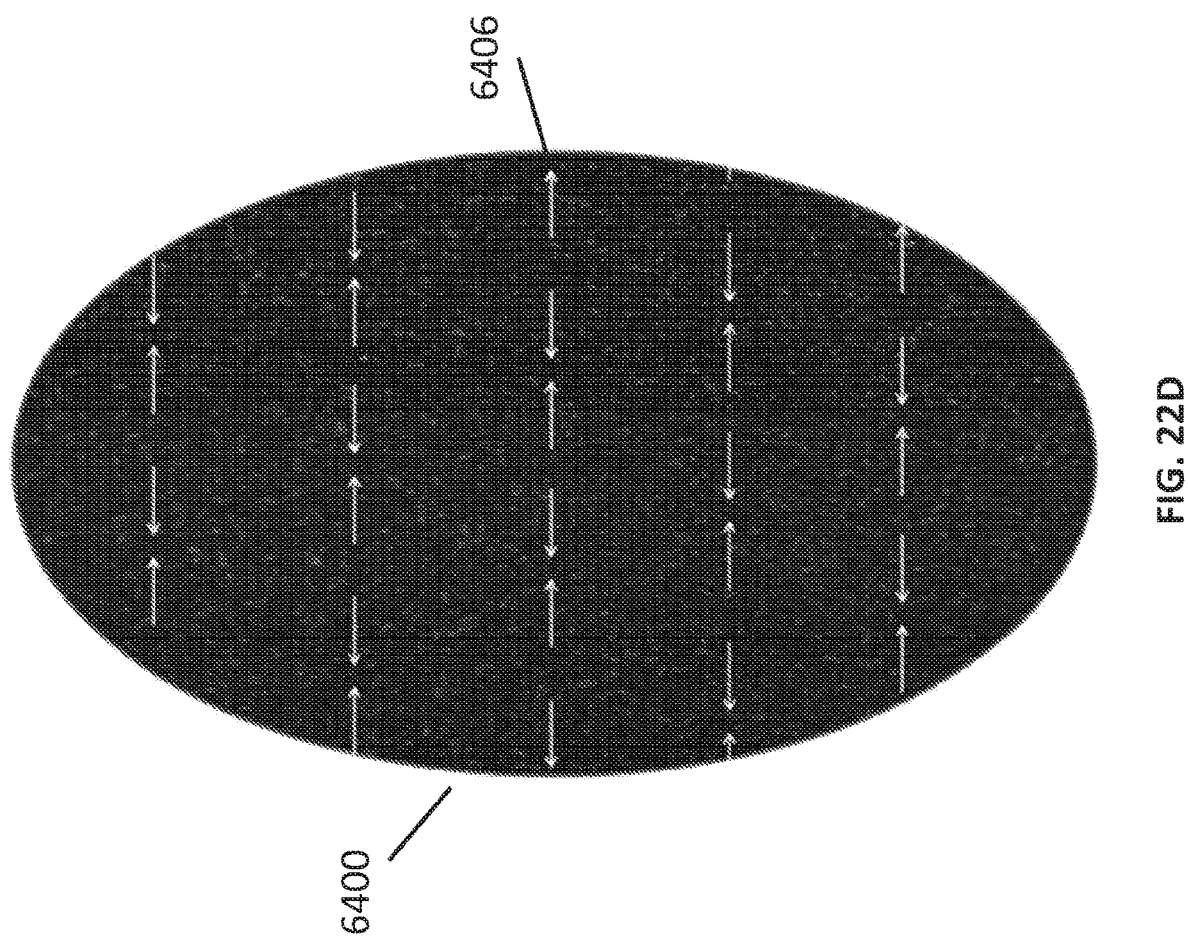
Figure 22E:
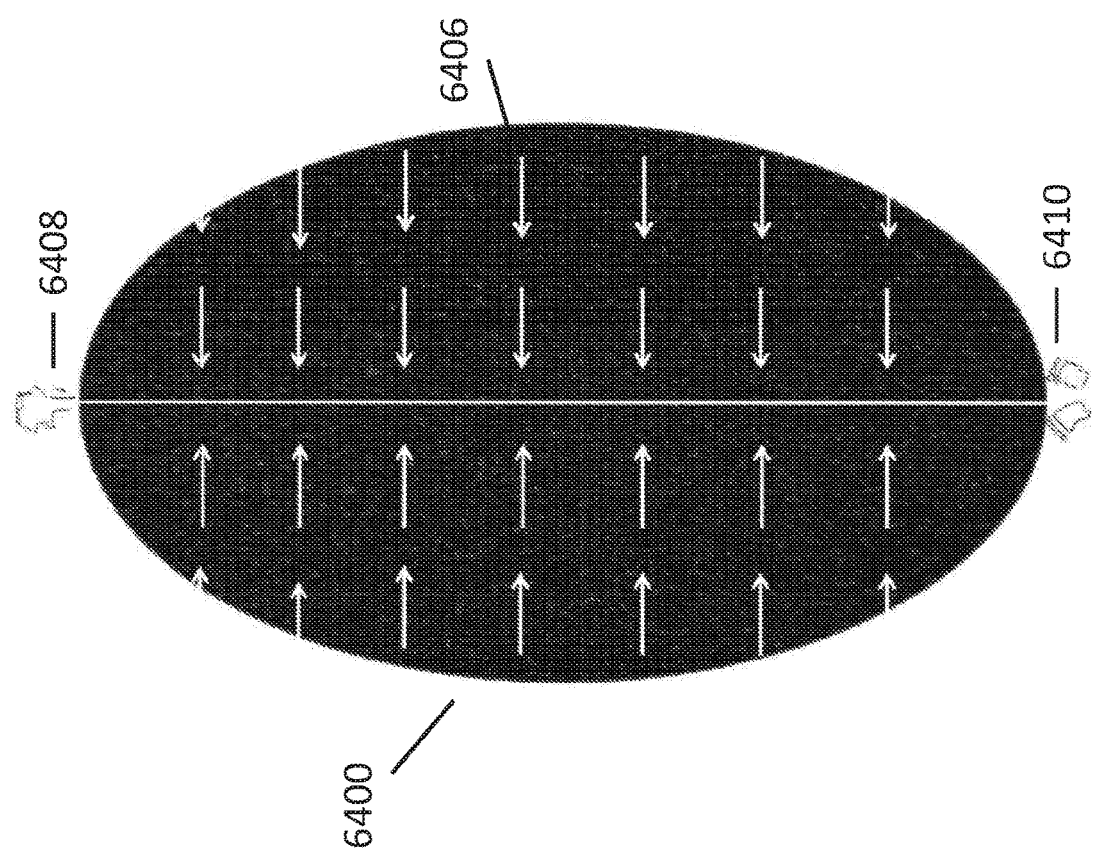

FIG. 22A depicts a simple unlabeled oval of foam 6400, such a layer provides little guidance for the proper orientation of the foam in the wound other than the general shape of the foam. FIG. 22B depicts an embodiment of a foam layer comprising horizontal stripes 6402. These horizontal stripes may be aligned along the shorter axis of a wound, thereby providing for ease of placement of the foam oval 6400. Similarly, FIG. 22C depicts an oval foam layer comprising longitudinal stripes 6404 which may be aligned with the longitudinal axis of the wound. FIG. 22D is similar to FIG. 22B, in that the horizontal arrows 6404 indicate alignment with the horizontal axis of the wound. Lastly, FIG. 22E combines the longitudinal stripes 6404 with the horizontal arrows 6404, but further includes "head" 6408 and "feet" 6410 symbols to direct the clinician to orient the head towards the head of the patient and the feet towards the feet of the patient.

In certain embodiments, foam layers similar to the foam layers of FIGS. 22B-E may include printing on one or both sides of the foam layer to indicate to the clinician which side of the foam or wound closure device is the top and which side is the bottom. Printing that precisely delineates the top, bottom, and orientation of the device may prevent a clinician from placing the wound closure device in a wound upside down or rotated in the wrong direction.

Figure 23B:
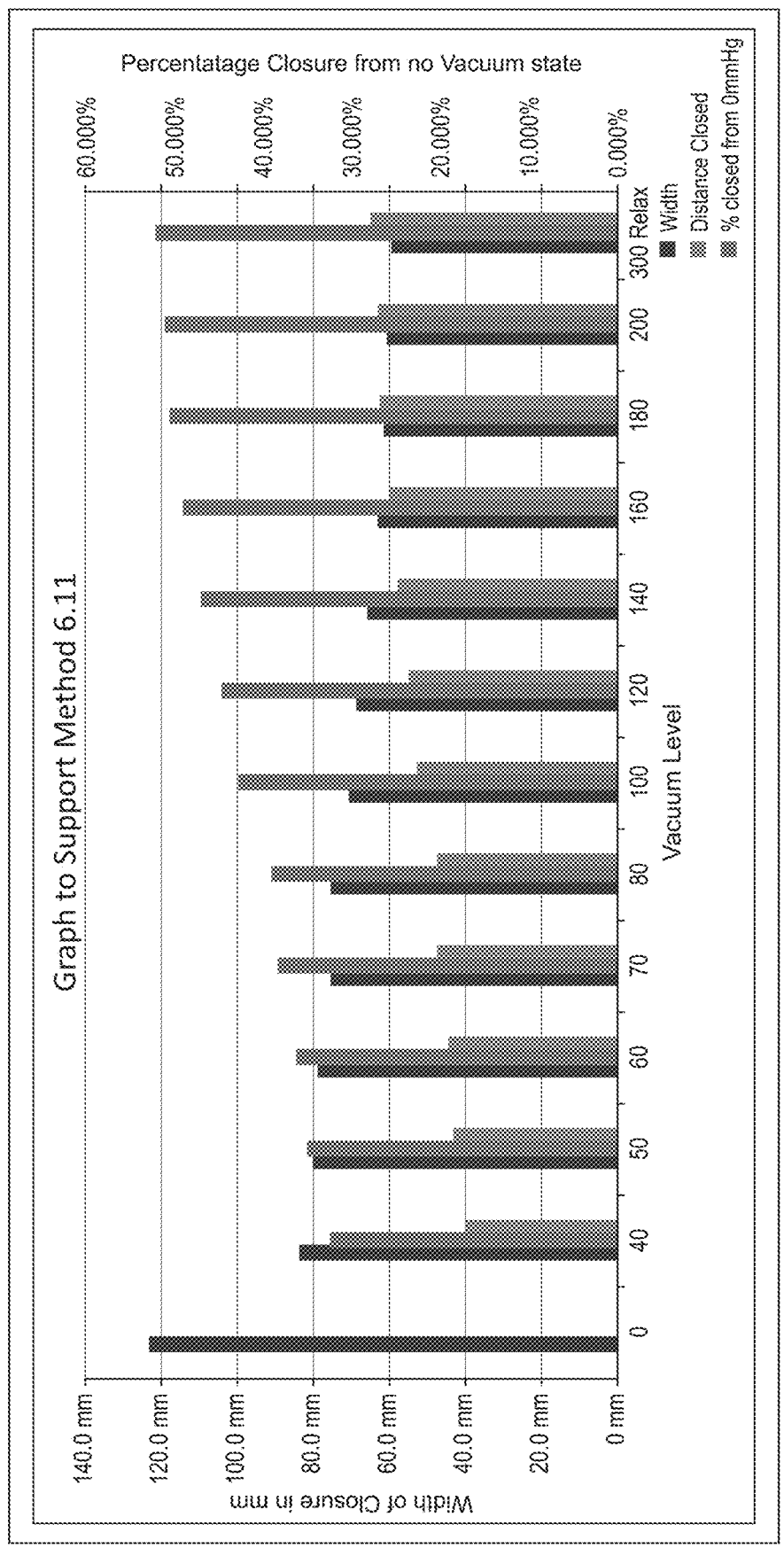

FIG. 23A is a data table that tracks the collapse (as measured by a decrease in width) of an embodiment of a wound closure device incorporating stabilizing structures similar to the structures of FIGS. 2A-3E and 16-20F, while the device is subjected to increasing levels of vacuum. Here, foam was attached to the top and the bottom of a stabilizing structure, similar to the embodiments of FIGS. 20A-20F and entire device was placed within an animal model. The vacuum was increased from 40 mm Hg to 200 mm Hg. The pre vacuum width of the device was 123.4 mm, which decreased to 83.4 mm under vacuum. FIG. 23B displays the experimental data of FIG. 23A in the form of a bar graph.

Various sensors may be placed within any of the stabilizing structures or foam layers described herein this section or elsewhere in the specification. For example, a pH, temperature, pressure sensor, or any other suitable sensor may be embedded within the stabilizing structure and/or within a foam layer. Such embodiments will advantageously allow a clinician to skip the step of removing a sensor within the wound bed, as the sensor simply be removed upon removal of the stabilizing structure or foam.

Stabilizing Structures of FIGS. 24A-29

FIGS. 24A-29 are drawings and photographs of various embodiments of a stabilizing structure 6500. Unless otherwise noted, reference numerals in FIGS. 24A-29 refer to components that are the same as or generally similar to the components in the preceding figures. It will be understood that the stabilizing structures shown in FIGS. 24A-29 can be used with any of the embodiments described and/or contemplated herein. It will also be understood that any of the embodiments described and/or contemplated herein can be modified to be used with the stabilizing structures shown in FIGS. 24A-29.

As used in this section or elsewhere in this specification, the x direction, when referring to the stabilizing structure, generally refers to a direction or plane generally parallel to the skin surrounding the wound. The y direction, when referring to the stabilizing structure, generally refers to a direction or plane generally parallel to the skin surrounding the wound and extending perpendicular to the x direction. The z direction, when referring to the stabilizing structure, generally refers to a direction or plane extending perpendicular to the x direction and the y direction. The term "width," when referring to a stabilizing structure, generally refers to a dimension of the stabilizing structure taken in the x direction along which the stabilizing structure is longest. The term "length," when referring to a stabilizing structure, generally refers to a dimension of the stabilizing structure taken in the y direction along which the stabilizing structure is longest. The term "height," when referring to a stabilizing structure, generally refers to a dimension of the stabilizing structure taken in the z direction along which the stabilizing structure is longest. The terms "width," "length," and "height" may also be used to describe the cells within the stabilizing structures and wound closure devices described throughout this specification. When describing these structures or devices, these terms should not be construed to require that the structures or devices necessarily be placed into a wound in a certain orientation, though in certain embodiments, it may be preferable to do so.

As described above, all stabilizing structures described herein this section or elsewhere in the specification may be fashioned to accommodate any size of wound. In some embodiments the stabilizing structures may be sized to better accommodate the needs of the clinical environment. In certain embodiments, the height of the un-collapsed stabilizing structure 6500 may be at least 1 mm, 5 mm, 10 mm, 15 mm, 20 mm, 25 mm, 30 mm, 35 mm, or greater than 35 mm. For example, the height of the un-collapsed stabilizing structure 6500 may be between 25 mm and 30 mm.

Stabilizing structure 6500 may be constructed via any means described herein this section or elsewhere in the specification. The stabilizing structure 6500 may also be comprised of any materials described in this section or elsewhere in this specification. For example, the stabilizing structure 6500 may comprise polyurethane. Additionally, the stabilizing structure 6500 may be constructed via various means and/or comprised of various materials to alter the material properties throughout different portions of the stabilizing structure 6500. In some embodiments, the material may be selected based on the material's Young's modulus to optimize stiffness of the stabilizing structure 6500 and influence closure of the stabilizing structure 6500. For example, the Young's modulus may affect cell 6504 size and/or the width of the stabilizing structure 6500 upon application of negative pressure to the stabilizing structure 6500. A higher Young's modulus may generally result in less closure of the stabilizing structure 6500 and larger cell 6504 size at a given negative pressure. Additionally, material selection may take into account the affect aging and some methods of sterilization may have on the Young's modulus of the stabilizing structure 6500. As such, in some embodiments, the stabilizing structure 6500 may comprise a material with a Young's modulus that will provide sufficient stiffness in the y and z directions, while maintaining sufficient support to keep cells 6504 open for fluid management upon the application of negative pressure to the stabilizing structure 6500. In certain embodiments, the Young's modulus of the stabilizing structure 6500 may be at least 0.5 MPa, 1 MPa, 2 MPA, 3 MPa, 4 MPa, 5 MPa, 6 MPa, 7 MPa, 8 MPa, 9 MPa, 10 MPa, 11 MPa, 12 MPa, 13 MPa, 14 MPa, 15 MPa, 16 MPa. 17 MPa, 18 MPa, 19 MPa, 20 MPa, 21 MPa, 22 MPa, or greater than 22 MPa depending on the material and curing protocol selected for the stabilizing structure 6500. Additionally, the stabilizing structure 6500 may be constructed via various means and/or comprised of various materials to alter the Young's modulus throughout different portions of the stabilizing structure 6500.

In some embodiments, the material may also be selected based on the material's Shore hardness to optimize stiffness of the stabilizing structure 6500 and influence closure of the stabilizing structure 6500. In certain embodiments, the Shore hardness of the stabilizing structure 6500 may be at least 40 Shore, 50 Shore, 60 Shore, 70 Shore, 80 Shore, 90 Shore, or greater than 90 Shore depending on the material selected for the stabilizing structure 6500. Additionally, the stabilizing structure 6500 may be comprised of various materials to alter the Shore hardness throughout different portions of the stabilizing structure 6500.

Figure 24A:
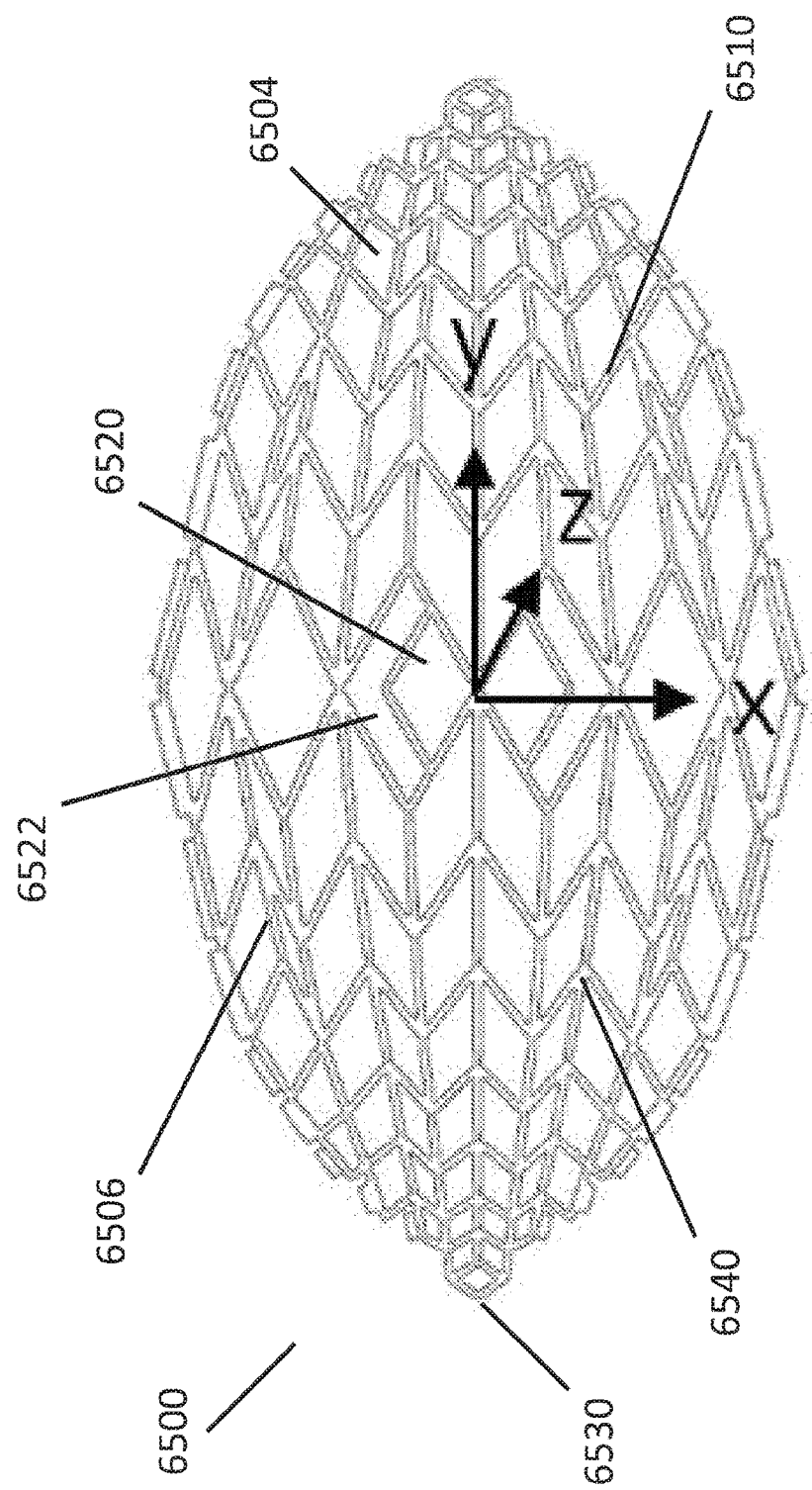
FIGS. 24A-24C illustrate an embodiment of a stabilizing structure.
Figure 24B:
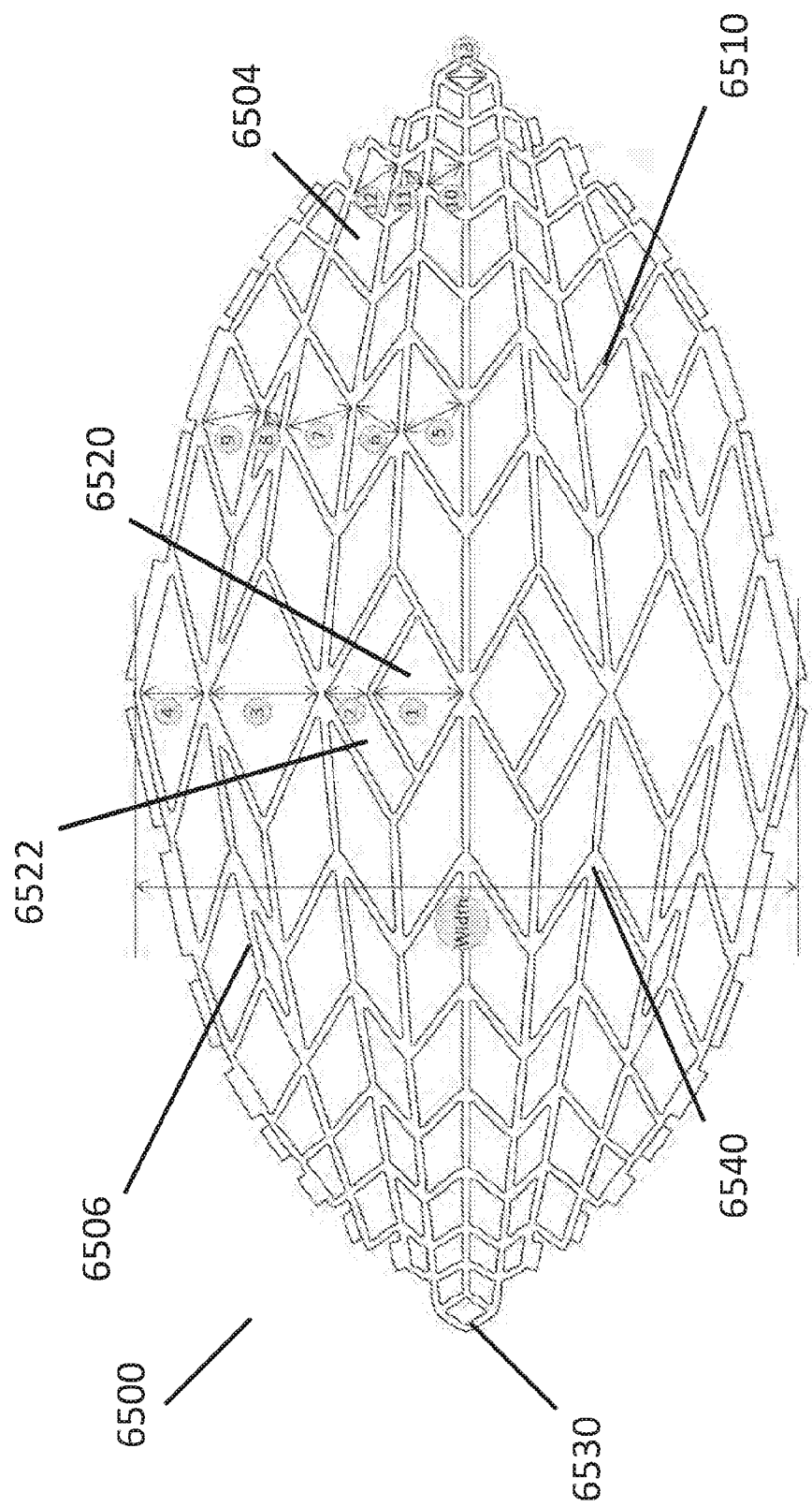
Figure 24C:
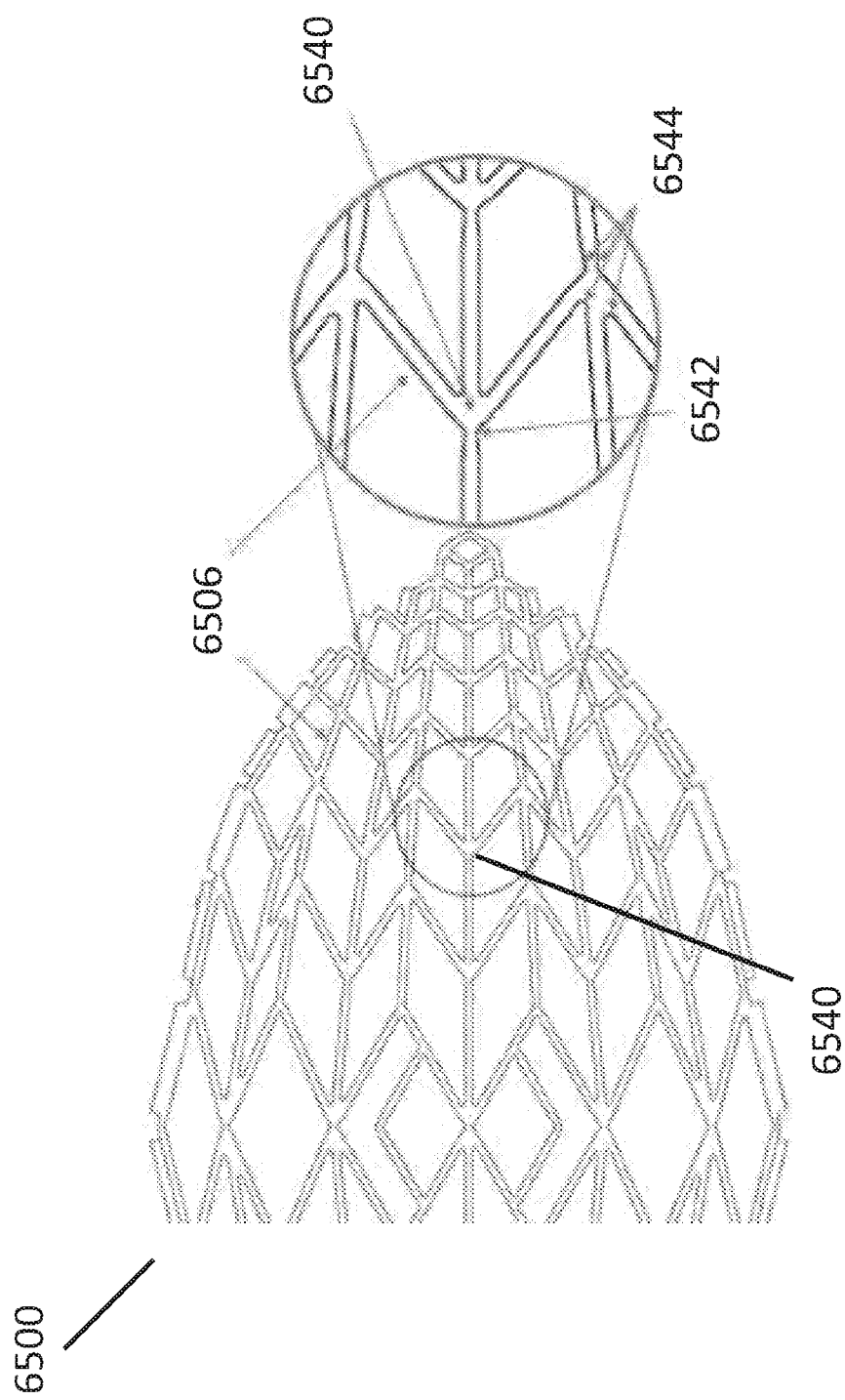

FIGS. 24A-24C are drawings of an embodiment of a stabilizing structure 6500 form a top view comprising a plurality of elongate strips or walls 6506 arranged in parallel or semi-parallel, whose longitudinal length can be aligned with the longitudinal axis of a wound. In some embodiments, the elongate strips or walls 6506 may also be arranged in a non-parallel fashion. The various cells 6504 defined by stabilizing structure 6500 may have a variety of shapes and sizes. As will be described in greater detail below, the length and shape of the elongate strips or walls 6506, intervening members or walls 6510, and cells 6504 may be designed and varied throughout the stabilizing structure 6500 so as to facilitate greater closure of the stabilizing structure 6500.

The stabilizing structure 6500 may comprise a plurality of adjacent rows of cells 6504 parallel to a central transverse axis and centered along a longitudinal axis of the stabilizing structure 6500. The rows and cells may be designed in a manner to facilitate closure of the stabilizing structure 6500 upon the application of negative pressure. In some embodiments, cells 6504 of the central row may have the greatest length compared to cells 6504 of the outer rows and extends across the width of the stabilizing structure 6500. The central row may be adjacent to smaller rows, with the remaining rows getting progressively smaller row-by-row along the longitudinal axis towards the longitudinal ends 6530.

In some embodiments, the rows comprise diamond-shaped cells 6504 with various sizes. The central row may comprise smaller diamond-shaped cells 6520 within larger diamond-like shaped cells 6522. This design may provide greater overall closure of the stabilizing device 6500 to provide for maximum closure of the wound. The smaller diamond-like shapes 6520 located within larger diamonds 6522 can also spread the load over a greater area reducing the chance of damage to the tissue structures below the matrix. The central row may further comprise additional diamond-shaped cells 6504.

The remaining rows may contain diamond-shaped cells 6504 of varying sizes. Cell 6504 width may be measured across the shorter of the two diagonals for each cell 6054, as shown in FIG. 24B. The cell 6504 length may then refer to the longer of the two diagonals for each cell 6054. In some embodiments, each row may comprise cells 6504 of alternating widths. For example, the central-most cell 6504 may have the largest width, shown as length 5 in FIG. 24B. The adjacent cell 6504 in the row may have a smaller length 6, with the following cell 6504 having a width 7 larger than the previous cell 6054 width 6. In this manner, cells within the same row may alternate between smaller and larger widths. In certain embodiments, the stabilizing structure 6500 may further contain cell size variations between cells located throughout different portions of the stabilizing structure 6500.

While the embodiments described herein in this section or elsewhere in this specification refer to diamond-shaped cells 6504, it will be understood that the location, shape, and relative sizes of the cells 6504 can be modified for any suitable embodiment and that their relative proportions can differ in various embodiments.

The wall thickness of the elongate strips or walls 6506 and/or intervening members or walls 6510 may be varied to affect the width of the stabilizing structure 6500 or individual cell 6504 sizes upon application of negative pressure. In some embodiments, the wall thickness may be increased to increase stiffness and bulk of the stabilizing structure 6500, thus resulting in a larger width of the stabilizing structure 6500 during closure. In certain embodiments, the wall thickness of the elongate strips or walls 6506 and/or intervening members or walls 6510 may be at least 0.5 mm, 1 mm, 1.5 mm, 2 mm, 2.5 mm, or greater than 2.5 mm. For example, the wall thickness may be between 1.5 mm and 2 mm. Additionally, the stabilizing structure 6500 may comprise elongate strips or walls 6506 and/or intervening members or walls 6510 of various wall thickness to alter the collapse the stabilizing structure 6500 upon application of negative pressure to the wound when the stabilizing structure 6500 is inserted into the wound, thus facilitating closure of the stabilizing structure 6500 during collapse. In certain embodiments, the stabilizing structure 6500 may further contain wall thickness variations between walls located throughout different portions of the stabilizing structure 6500.

The stabilizing structure 6500 of FIGS. 24A-26 may differ from the stabilizing structures of FIGS. 2A-3E and 16-19D, due to the inclusion of nodes 6540. Nodes 6540 comprise an intersection of two or more elongate strips or walls 6506 and/or intervening members or walls 6510. In some embodiments, as shown in FIGS. 24C-26, nodes 6540 may further comprise a hinge 6542 that arises from variable wall thickness of the elongate strips or walls 6506 and/or intervening members or walls 6510. The walls may taper inwardly at each end to create the hinge 6542 at the node 6540. The hinge 6542 may allow the stabilizing structure 6500 to increase rotation between one or more walls at the node 6540 upon application of negative pressure to the wound when the stabilizing structure 6500 is inserted into the wound, thus facilitating closure of the stabilizing structure 6500 during collapse. FIGS. 25-27 further illustrate various embodiments of the stabilizing structure 6500, 6600; wall 6506, 6606 thickness; and node 6540, 6640. For example, both FIGS. 25-26 illustrate a stabilizing structure 6500 having a node 6540 comprising a hinge 6542; however, as compared in to FIG. 25, the stabilizing structure 6500 shown in FIG. 26 has an increased wall 6506 thickness along the entire wall length. In alternative embodiments, as shown in FIG. 27, the stabilizing structure 6500 may have walls of singular thickness and, thus, may not include a hinge 6542 at the node 6640.

The nodes 6540 may further have various internal radii 6544 to affect the width of the stabilizing structure 6500 or individual cell 6504 sizes upon application of negative pressure. In some embodiments, the internal radii 6544 may be increased to increase the stiffness of the stabilizing structure 6500 by also increasing the wall thickness and wall stiffness, thus permitting less wall bending close to the node 6540 during collapse. This may also result in a larger width of the stabilizing structure 6500 during closure. Additionally, the increased internal radius 6544 further increases the size of fluid channels forming at the corner of the cells 6504 during collapse. In certain embodiments, the internal radii 6544 of the un-collapsed cells 6504 may be at least 0.1 mm, 0.2 mm, 0.3 mm, 0.4 mm, 0.5 mm, 0.6 mm, 0.7 mm, 0.8 mm, 0.9 mm, 1.0 mm, 1.1 mm, 1.2 mm, 1.3 mm, 1.4 mm, 1.5 mm, or greater than 1.5 mm. For example, the internal radii 6544 of the un-collapsed cells 6504 may be between 0.55 mm and 1.0 mm. In certain embodiments, the stabilizing structure 6500 may further contain internal radii variations between cells located throughout different portions of the stabilizing structure 6500.

Figure 28A:
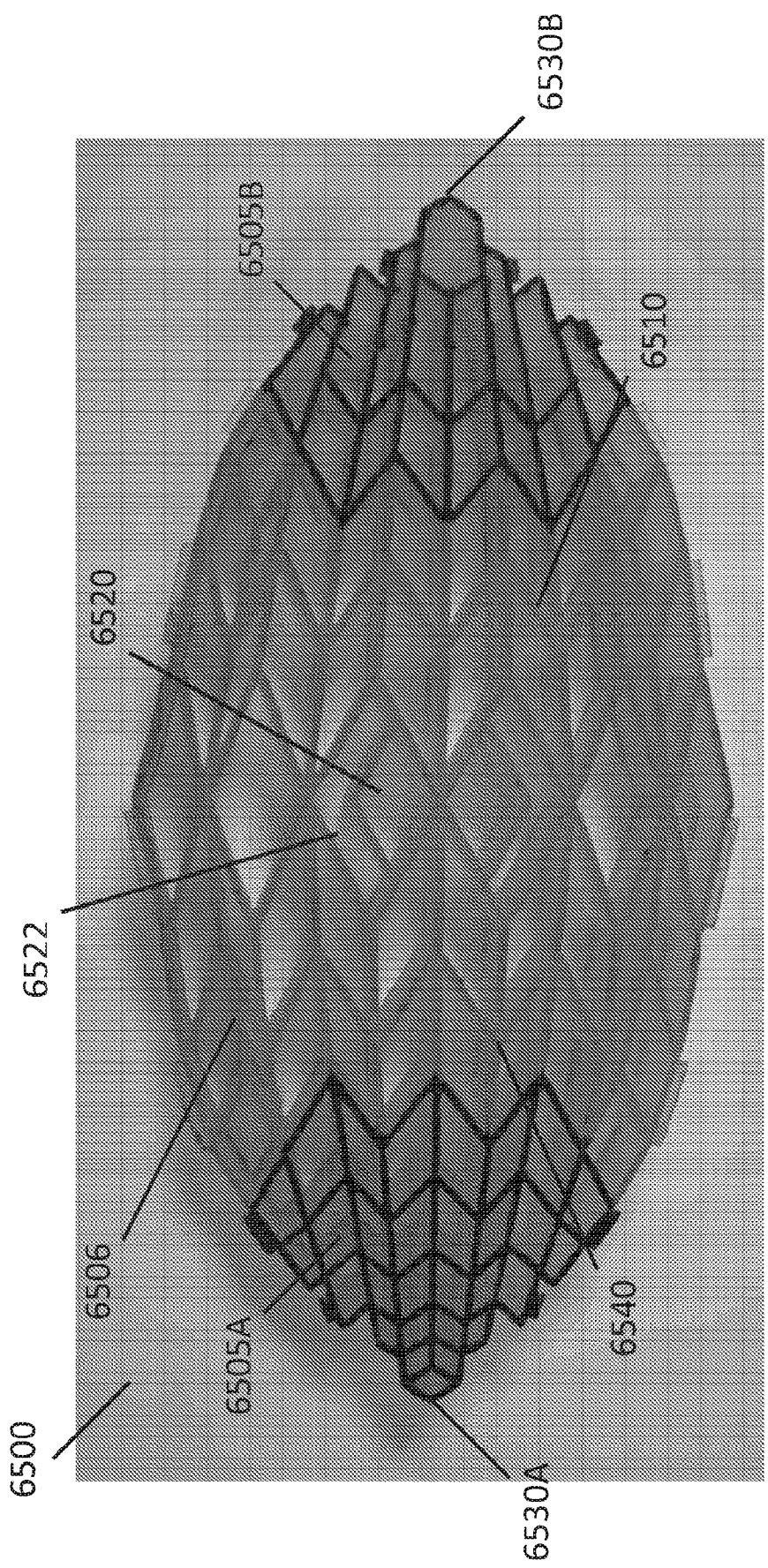
FIGS. 28A-28E are photographs of another embodiment of a stabilizing structure subject to negative pressure.
Figure 28B:
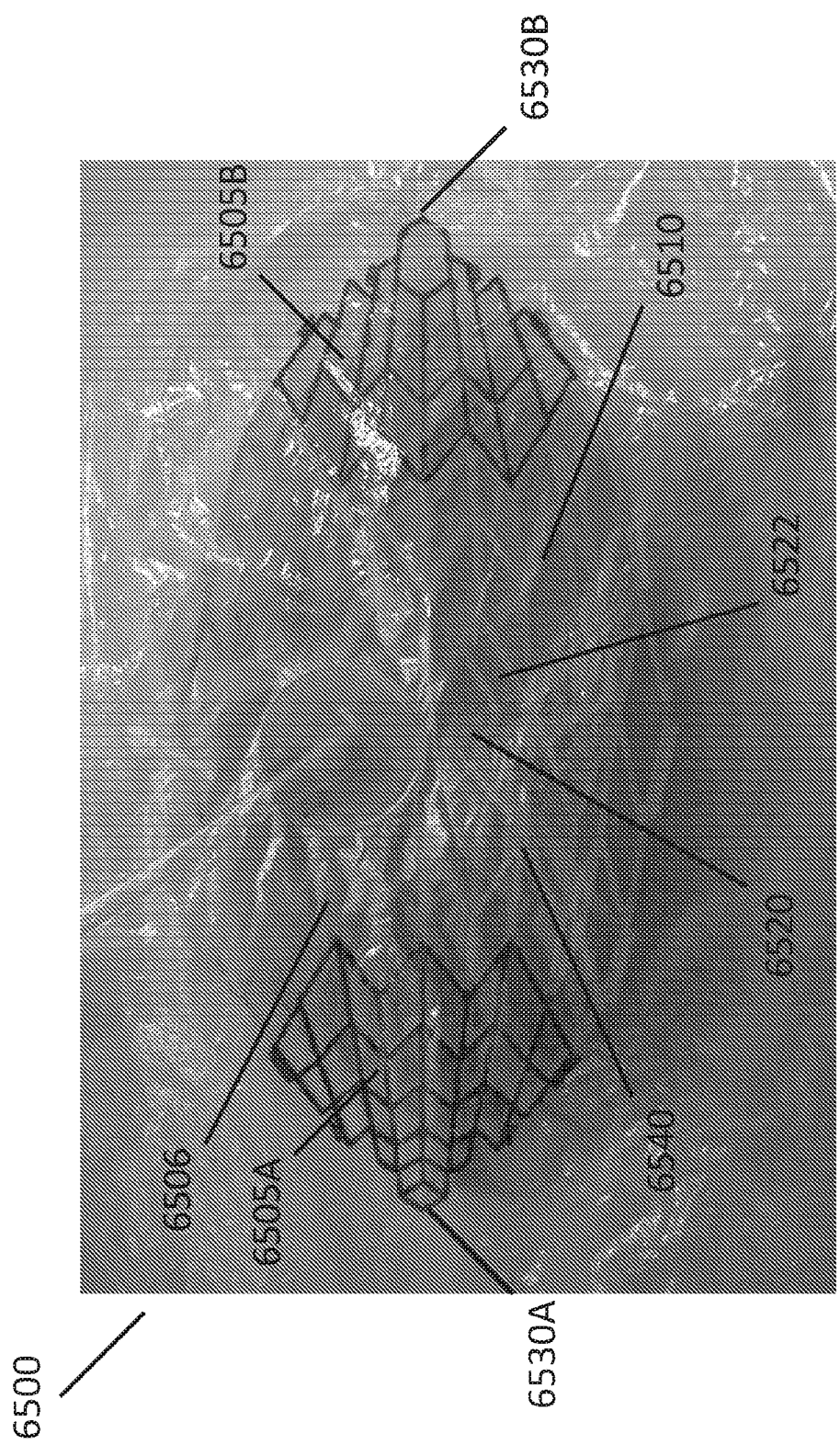
Figure 28C:
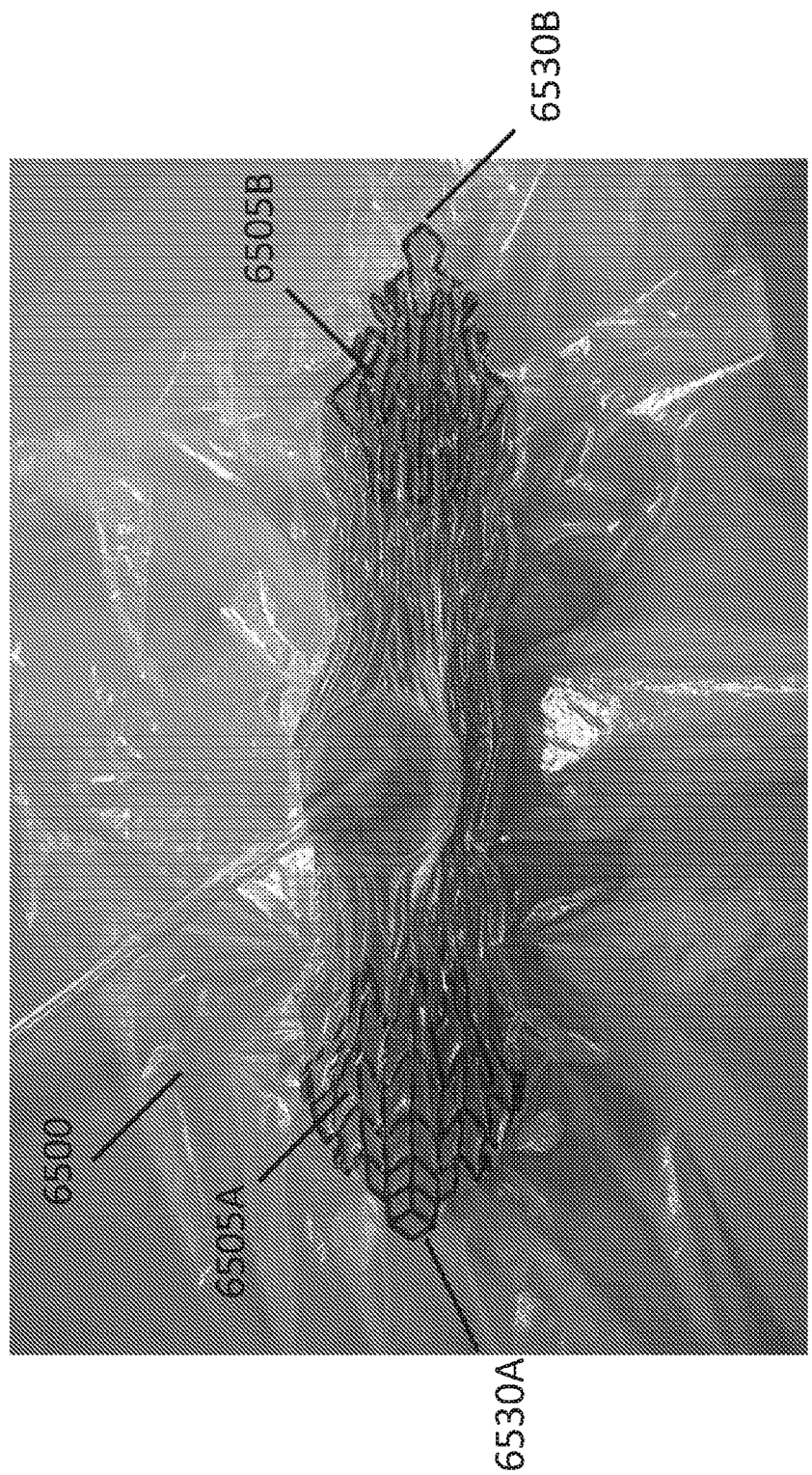
Figure 28D:
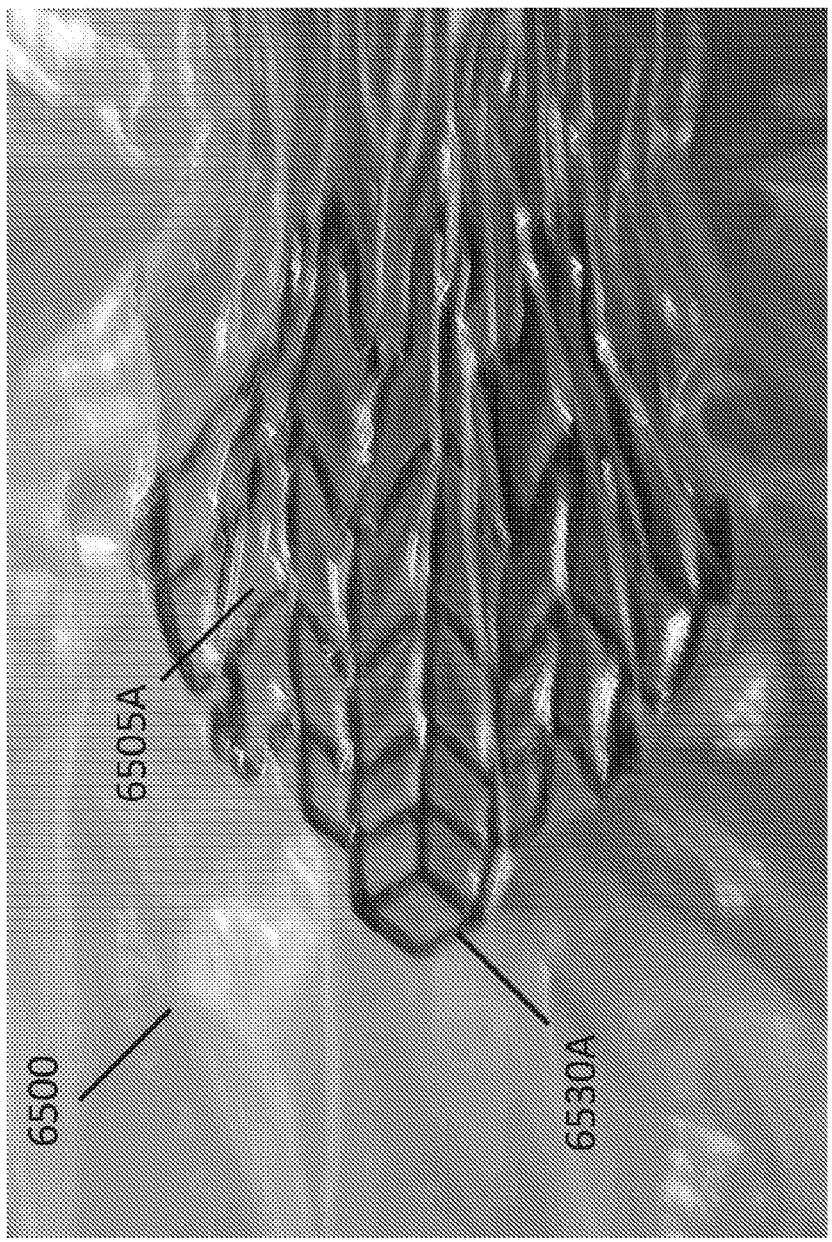
Figure 28E:
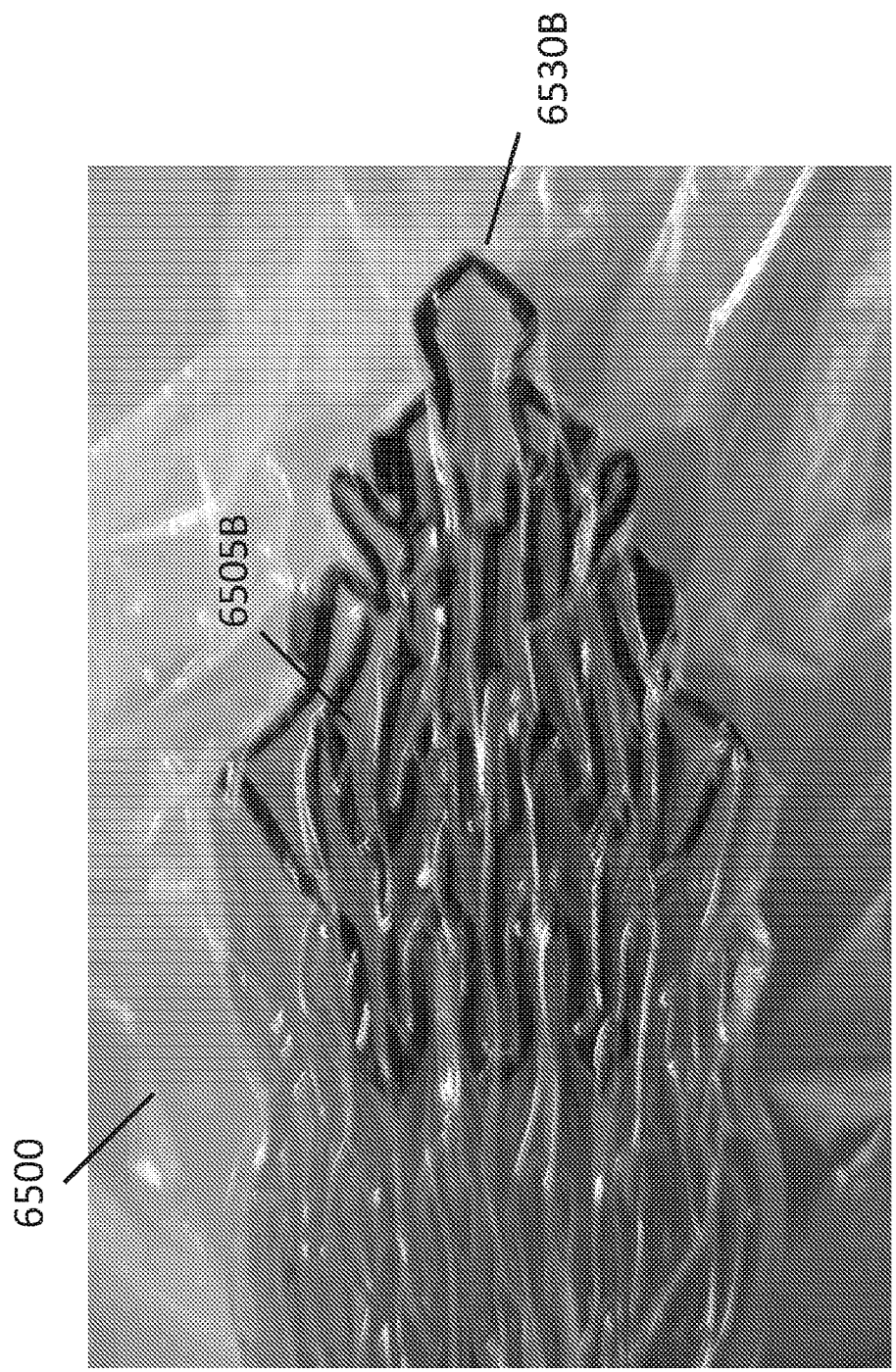

In addition to the cell 6504 arrangement within the stabilizing structure 6500 described above, the length and shape of the cell 6504 sizes of the stabilizing structure 6500 may be further designed to increase closure of the stabilizing structure 6500 upon application of negative pressure. In some embodiments, the stabilizing structure 6500 may further contain size variations between cells located within a center portion and cells located within the longitudinal end portions 6530 of the stabilizing structure 6500. Cells may be sized and configured to promote uniform collapse of the stabilizing structure within both longitudinal end portions and a central portion between the longitudinal end portions. FIGS. 28A-28B are photographs of an embodiment of the stabilizing structure 6500, similar to stabilizing structure of FIGS. 2A-3E, 16D-19, and 24A-24C. Much like the stabilizing structures disclosed elsewhere in the specification, the stabilizing structure 6500, comprises elongate strips or walls 6056, cells 6504, and intervening members or walls 6510. In some embodiments, the stabilizing structure 6500 may further comprise two longitudinal end portions 6530A, 6530B with variations in cell sizes to further facilitate closure of the stabilizing structure 6500. For example, as shown in FIGS. 28A-28E, the second and third to the last rows from the longitudinal right end have several intervening members or walls 6510 removed to increase the size and width of cells 6505B, in relation to cells 6505A. The increased cell 6504 size may be designed to facilitate closure of the stabilizing structure 6500. FIGS. 28C-28E are photographs of multiple views of the stabilizing structure 6500 of FIGS. 28A-28B, in a collapsed state. During collapse, the length and height of the stabilizing structure remained the same while the width decreases significantly. Additionally, as shown in FIG. 28C, increasing the cell sizes 6504B results in increased collapse of the longitudinal end portion 6530B of the stabilizing structure 6500 so that the width of the longitudinal end portion is about the same as the width at the central transverse axis upon application of negative pressure. FIGS. 28D-28E provide a zoomed-in views of the two longitudinal end portions 6530A, 6530B. While FIGS. 28A-28E show the stabilizing structure 6500 as having only a right longitudinal end portion 6530B comprising increased cell 6505B sizes, it is understood that the longitudinal end portion 6530A, longitudinal end portion 6530B, or a combination of both longitudinal end portions 6530A, 6530B may have increased cell 6505B sizes to facilitate closure of the stabilizing structure 6500 upon application of negative pressure. Additionally, it is contemplated that any combination of walls 6506 or walls 6510 may be removed to obtain the desired cell 6504 sizes and closure of the stabilizing structure 6500.

Figure 29:
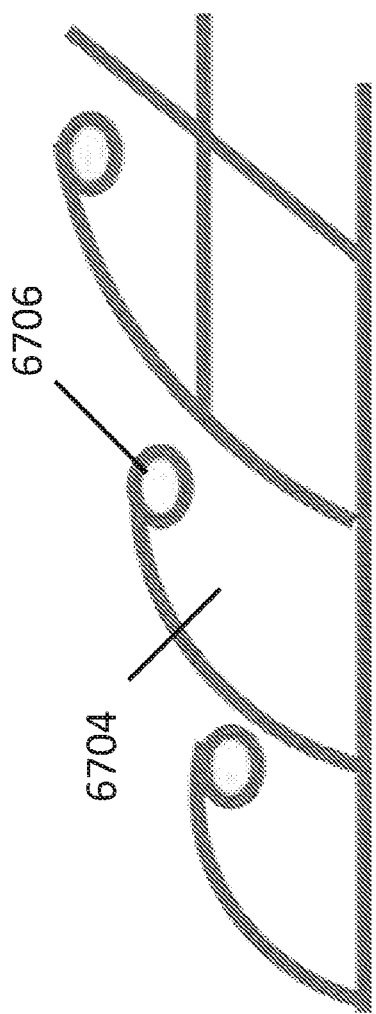
FIG. 29 illustrates another embodiment of a wall pattern for a stabilizing structure.

It may be desired to design the longitudinal edges or other outer portions of the stabilizing structure 6500 to increase collapse of the longitudinal edge portions 6530. In certain embodiments, the stabilizing structure 6500 may comprise open cells near or at the longitudinal end portions 6530 and/or outer walls of the stabilizing structure 6500. For example, as illustrated in FIG. 29, the open cells 6704 may have walls terminating prior to connecting to the adjacent cell. The terminating end 6706 of the open cell 6704 may curve towards a central transverse axis. In some embodiments, the terminating end 6706 may comprise a various types of ends. For example, in certain embodiments, the terminating end 6706 may comprise a rounded end or an angled end. The open cells 6706 may alter the collapse the stabilizing structure 6500 upon application of negative pressure to the wound when the stabilizing structure 6500 is inserted into the wound, thus facilitating closure of the stabilizing structure 6500 during collapse. The design may lower stiffness at the stabilizing structure 6500 edges, thus increasing the collapse of the stabilizing structure 6500 upon application of negative pressure.

The stabilizing structure 6500 may be designed to collapse in any manner described in this section or elsewhere in this specification with or without the application of negative pressure. For example, the stabilizing structure 6500 may collapse in a progressive manner with increasing negative pressure. In some embodiments, particular cells 6504 may collapse before other cells 6504. For example, the cells 6504 adjacent to the outer edges of the stabilizing structure 6500 and/or cells 6504 farther away from the central longitudinal axis of the stabilizing structure 6500 may collapse before the cells 6504 adjacent to the inner portion of the stabilizing structure 6500 and/or cells 6504 closer to the central longitudinal axis of the stabilizing structure 6500. The cells 6504 within the central rows of the stabilizing structure 6500 may collapse before cells 6504 located on the longitudinal end portions 6530. Additionally, the stabilizing structure 6500 and all stabilizing structures and wound closure devices described in this section or elsewhere in this specification may collapse on a variety of timescales in a dynamic fashion. In certain embodiments, various cells 6504 may be designed to collapse at a faster rate than other cells 6504.

Figure 30:
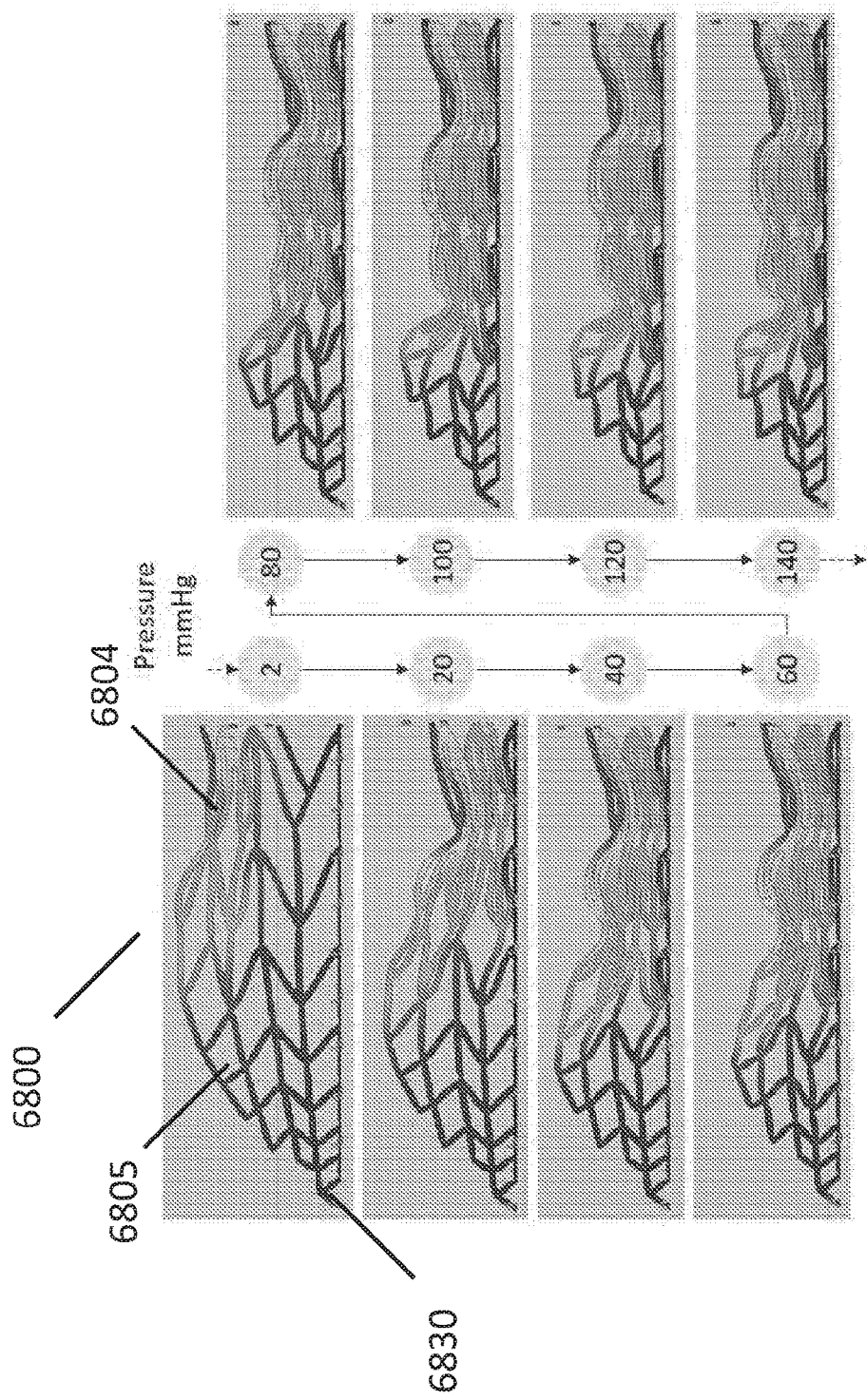
FIG. 30 illustrates an embodiment of a method of treating a wound with an embodiment of a stabilizing structure.

A method for treating a wound with a stabilizing structure may include inserting into a wound a stabilizing structure as described herein this section and elsewhere in the specification, overlaying the stabilizing structure with a wound cover, and applying negative pressure to cause the cells of the stabilizing structure to collapse. In certain embodiments, the stabilizing structure 6800 may be designed to collapse in a progressive manner with increasing negative pressure. For example, in some embodiments, as illustrated in FIG. 30, particular cells 6804 may collapse before other cells 6805. The cells 6804 within the central rows of the stabilizing structure 6800 may collapse before cells 6805 located on the longitudinal end portions 6830. Alternatively, in some embodiments, the stabilizing structure may be designed to permit the longitudinal end portions to collapse evenly or uniformly with the remainder of the stabilizing structure. FIGS. 28A-28E are photographs depicting an embodiment of methods for the treatment of a wound that utilize a wound closure device comprising a stabilizing structure having size variations between cells located within a center portion and cells located within the longitudinal end portions 6530 of the stabilizing structure 6500. FIG. 28A depicts an embodiment of the stabilizing structure 6500 with cell size variations. FIG. 28B depicts the stabilizing structure placed within a translucent sealable bag to view the closure of the stabilizing structure. FIG. 28C depicts the stabilizing structure 6500 within the translucent sealable bag following the application of negative pressure. FIG. 28E depicts an embodiment of the stabilizing structure 6500 in which the cells 6505B have been modified to cause the cells 6505B in the longitudinal end portion 6530B to collapse evenly with the cells of the central portion of the stabilizing structure 6500. FIG. 28E may be contrasted with FIG. 28D that depicts an embodiment of longitudinal end portion 6530A of the stabilizing structure 6500 without intervening members or walls 6510 removed, thereby maintaining the size and width of cells 6505A. As such, the cells 6505A in the longitudinal end portion 6530A do not collapse evenly or uniformly with the cells in the central portion or the cells 6505B in the longitudinal end portion 6530B of the stabilizing structure 6500, as depicted in FIGS. 28C and 28E.

Although this disclosure describes certain embodiments, it will be understood by those skilled in the art that many aspects of the methods and devices shown and described in the present disclosure may be differently combined and/or modified to form still further embodiments or acceptable examples. All such modifications and variations are intended to be included herein within the scope of this disclosure. Indeed, a wide variety of designs and approaches are possible and are within the scope of this disclosure. No feature, structure, or step disclosed herein is essential or indispensable. Moreover, while illustrative embodiments have been described herein, the scope of any and all embodiments having equivalent elements, modifications, omissions, combinations (e.g., of aspects across various embodiments), substitutions, adaptations and/or alterations as would be appreciated by those in the art based on the present disclosure. While certain embodiments have been described, these embodiments have been presented by way of example only, and are not intended to limit the scope of protection.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, 0.1 degree, or otherwise.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. An apparatus for treating a wound with negative pressure wound therapy, the apparatus comprising:
 a stabilizing structure for insertion into a wound, the stabilizing structure comprising:
  a length corresponding to a y-direction and extending along a central longitudinal axis of the stabilizing structure between a first end and a second end of the stabilizing structure;
  a width corresponding to an x-direction, the width being transverse to the length and extending along a central transverse axis of the stabilizing structure between a first side and a second side of the stabilizing structure;
a height corresponding to a z-direction, the height being transverse to the length and the width and extending between a top surface and a bottom surface of the stabilizing structure, wherein the length and width are each greater than the height; and
a plurality of cells being provided side-by-side in a horizontal plane parallel to the x-direction and the y-direction, each cell of the plurality of cells having:
a top end,
a bottom end, and
an opening extending through the top end and the bottom end in the z-direction;
wherein the stabilizing structure is configured such that, upon application of negative pressure to the wound when the stabilizing structure is inserted into the wound, the stabilizing structure collapses more in the horizontal plane than in the z-direction and collapses more in the x-direction than in the y-direction;
wherein one or more cells of the plurality of cells located farther away from the central transverse axis of the stabilizing structure are sized and configured to cause one or both longitudinal end portions of the stabilizing structure to collapse uniformly with a central portion of the stabilizing structure located between the longitudinal end portions upon application of negative pressure;
wherein the stabilizing structure has cells of varying size; and
wherein the stabilizing structure comprises one or more open cells, and wherein each open cell comprises at least one wall that terminates prior to connecting to an adjacent cell such that each open cell comprises a second opening extending through a cross-sectional perimeter of the open cell along the horizontal plane.

2. The apparatus of claim 1, wherein the stabilizing structure has an oculiform shape.

3. The apparatus of claim 1, wherein the stabilizing structure has walls of varying thickness.

4. The apparatus of claim 1, wherein the stabilizing structure has cells of varying internal radius.

5. The apparatus of claim 1, wherein the stabilizing structure has walls of varying stiffness or hardness.

6. The apparatus of claim 1, wherein cells located closer to the central transverse axis of the stabilizing structure are larger than cells located farther away from the central transverse axis of the stabilizing structure.

7. The apparatus of claim 1, wherein cells located closer to the central longitudinal axis of the stabilizing structure are larger than cells located farther away from the central longitudinal axis of the stabilizing structure.

8. The apparatus of claim 1, wherein a majority of the cells are diamond-shaped.

9. The apparatus of claim 1, wherein the stabilizing structure is symmetrical about its central longitudinal axis.

10. The apparatus of claim 1, wherein the stabilizing structure is symmetrical about its central transverse axis.

11. The apparatus of claim 1, wherein at least some of the cells relatively closer to a longitudinal end of the stabilizing structure are larger than cells relatively closer to the central longitudinal axis.

12. The apparatus of claim 1, wherein the one or more open cells are located closer to a longitudinal end of the stabilizing structure than the central transverse axis.

13. The apparatus of claim 12, wherein the cells of the stabilizing structure are sized and configured so that one or both longitudinal end portions of the stabilizing structure collapse to have about an end width equal to a central width at the central transverse axis upon application of negative pressure.

14. The apparatus of claim 1, wherein each opening comprises an opening length corresponding to the y-direction and an opening width corresponding to the x-direction, and wherein the opening length is greater than the opening width.

15. An apparatus for treating a wound with negative pressure wound therapy, the apparatus comprising:
a stabilizing structure for insertion into a wound, the stabilizing structure comprising:
a length corresponding to a y-direction and extending along a central longitudinal axis of the stabilizing structure between a first end and a second end of the stabilizing structure;
a width corresponding to an x-direction, the width being transverse to the length and extending along a central transverse axis of the stabilizing structure between a first side and a second side of the stabilizing structure;
a height corresponding to a z-direction, the height being transverse to the length and the width and extending between a top surface and a bottom surface of the stabilizing structure, wherein the length and width are each greater than the height; and
a plurality of cells being provided side-by-side in a horizontal plane parallel to the x-direction and the y-direction, each cell of the plurality of the cells comprising:
a top end;
a bottom end;
one or more sidewalls extending between the top end and the bottom end; and
an opening extending through the top end and the bottom end in the z-direction, the opening being at least partially defined by the one or more sidewalls;
wherein one or more cells of the plurality of cells are an open cell comprising a second opening extending through or between the one or more sidewalls of the open cell such that the second opening separates the one or more sidewalls from an adjacent sidewall,
wherein the stabilizing structure is configured such that, upon application of negative pressure to the wound when the stabilizing structure is inserted into the wound, the stabilizing structure collapses more in the horizontal plane than in the z-direction and collapses more in the x-direction than in the y-direction;
wherein the stabilizing structure has cells of varying size; and
wherein each open cell further comprises at least one sidewall that terminates prior to connecting to an adjacent cell.

16. The apparatus of claim 15, wherein the stabilizing structure comprises a plurality of open cells.

17. The apparatus of claim 15, wherein one or more open cells are located closer to a longitudinal end of the stabilizing structure than to the central transverse axis.

18. The apparatus of claim 15, wherein the second opening extends through the one or more sidewalls defining the open cell.

19. The apparatus of claim 15, wherein the second opening extends between the one or more sidewalls defining the open cell, and wherein at least one of the one or more sidewalls are located along an outer edge of the stabilizing structure.

20. The apparatus of claim 1, wherein the plurality of cells are arranged within the stabilizing structure symmetrically about the central longitudinal axis and the central transverse axis.

21. The apparatus of claim 1, wherein the stabilizing structure comprises:
- at least one outer cell of the plurality of cells being positioned on the central longitudinal axis and being bisected by the central longitudinal axis; and
- at least one pair of inner cells of the plurality of cells being positioned between the at least one outer cell and the central transverse axis, the at least one pair of inner cells being spaced away from the central longitudinal axis, the at least one pair of inner cells being symmetrically disposed relative to the central longitudinal axis such that a first cell of the pair of inner cells is positioned on one side of the central longitudinal axis and a second cell of the pair of inner cells is positioned on an opposite side of the central longitudinal axis.

22. The apparatus of claim 21, wherein one or more walls of the stabilizing structure separate the first cell and the second cell and are positioned on the central longitudinal axis.

23. The apparatus of claim 15, wherein the open cells are configured to cause one or both longitudinal end portions of the stabilizing structure to collapse uniformly with a central portion of the stabilizing structure between the longitudinal end portions upon application of negative pressure.

* * * * *